United States Patent
Ishihara et al.

(10) Patent No.: US 12,268,709 B2
(45) Date of Patent: Apr. 8, 2025

(54) NITROGENOUS GAS SUSTAINED RELEASING AGENT AND NITROGENOUS GAS SUSTAINED RELEASER COMPOSED OF THE SAME AS WELL AS NITROGENOUS GAS SUSTAINED RELEASING METHOD, RESPIRATORY EQUIPMENT, PACKAGE, AND SUSTAINED RELEASING APPARATUS USING THE SUSTAINED RELEASER

(71) Applicant: NATIONAL INSTITUTE FOR MATERIALS SCIENCE, Tsukuba (JP)

(72) Inventors: Shinsuke Ishihara, Tsukuba (JP); Nobuo Iyi, Tsukuba (JP)

(73) Assignee: NATIONAL INSTITUTE FOR MATERIALS SCIENCE, Tsukuba (JP)

( * ) Notice: Subject to any disclaimer, the term of this patent is extended or adjusted under 35 U.S.C. 154(b) by 725 days.

(21) Appl. No.: 17/604,387

(22) PCT Filed: Apr. 1, 2020

(86) PCT No.: PCT/JP2020/015001
§ 371 (c)(1),
(2) Date: Oct. 15, 2021

(87) PCT Pub. No.: WO2020/213398
PCT Pub. Date: Oct. 22, 2020

(65) Prior Publication Data
US 2022/0211748 A1    Jul. 7, 2022

(30) Foreign Application Priority Data
Apr. 19, 2019 (JP) ................................ 2019-079709

(51) Int. Cl.
*A61K 33/00* (2006.01)
*A61K 9/00* (2006.01)

(52) U.S. Cl.
CPC ............ *A61K 33/00* (2013.01); *A61K 9/0004* (2013.01)

(58) Field of Classification Search
CPC .............................. A61K 33/00; A61K 9/0004
See application file for complete search history.

(56) References Cited

U.S. PATENT DOCUMENTS

| | | | |
|---|---|---|---|
| 5,485,827 A | 1/1996 | Zapol et al. | |
| 6,046,243 A * | 4/2000 | Wellinghoff | A01N 59/00 424/416 |
| 6,416,599 B1 | 7/2002 | Yoshikawa et al. | |
| 6,656,382 B1 | 12/2003 | Kuhlmann et al. | |

FOREIGN PATENT DOCUMENTS

| | | | |
|---|---|---|---|
| EP | 3822226 A1 | | 5/2021 |
| JP | H10113678 | * | 5/1998 |
| JP | 2006-056829 A | | 3/2006 |
| WO | 98/029361 A1 | | 7/1998 |
| WO | WO 1998029361 | * | 7/1998 |
| WO | 2020/012994 A1 | | 1/2020 |

OTHER PUBLICATIONS

Sasai et al. J. Hazadous Materials 215-216 (2012)311-314.*
Xu et al J. Materials Science; 52; 5908-5916 (2017).*
J. D. Roberts et al., "Inhaled nitric oxide and persistent pulmonary hypertension of the newborn", N. Eng. J. Med., 1997, vol. 336, p. 605-610.
B. Yu et al., "Producing nitric oxide by pulsed electrical discharge in air for portable inhalation therapy", Sci. Transl. Med. 2015, vol. 7, 7,294ra107.
N. Iyi et al., "Effect of KBr on the FTIR Spectra of NO3-LDHs (Layered Double Hydroxides)", Chem. Lett. 2009, vol. 38, 808-809.
N. Iyi et al., "Factors influencing the hydration of layered double hydroxides (LDHs) and the appearance of an intermediate second staging phase", Applied Clay Science 2007, vol. 35, 218-227.
N. Iyi et al., "Efficient decarbonation of carbonate-type layered double hydroxide (CO32-LDH) by ammonium salts in alcohol medium", Applied Clay Science 2012, vol. 65-66, 121-127.
E. D. Bloch et al., "Gradual release of strongly bound nitric oxide from Fe2(NO)2 (dobdc)", J. Am. Chem. Soc., 2015, vol. 137, p. 3466-3469.
Sahoo, P. et al., "Rapid Exchange between Atmospheric CO2 and Carbonate Anion Intercalated within Magnesium Rich Layered Double Hydroxide", ACS Appl Mater Interfaces, 2014, vol. 6, No. 20, p. 18352-18359, abstract.
Yuwan, T. et al., "Zn—Al—NO2 layered double hydroxide as a controlled-release corrosion inhibitor for steel reinforcements", Materials Letters, 2018, vol. 236, pp. 517-520, abstract.
Rodriguez-Rivas, F. et al., "Zn—Al layered double hydroxides as efficient photocatalysts for NOx abatement", Chemical Engineering Journal, 2018, vol. 346, pp. 151-158, abstract.

(Continued)

*Primary Examiner* — Shirley V Gembeh
(74) *Attorney, Agent, or Firm* — IP Business Solutions, LLC

(57) ABSTRACT

The invention provides a nitrogenous gas sustained releasing agent that is capable of sustainably releasing off nitrogenous gases in the air at normal temperature and safe to handle and a nitrogenous gas sustained releaser composed of the same as well as a nitrogenous gas sustained releasing method, respiratory equipment, a package and a nitrogenous gas sustained releasing apparatus using said sustained releaser. The nitrogenous gas sustained releasing agent contains a layered double hydroxide having nitrite ions ($NO_2^-$) and/or nitrate ions ($NO_3^-$) included between layers. The nitrogenous gas sustained releaser composed of the sustained releasing agent is exposed to a gas containing carbon dioxide and water vapor to induce any one or more processes of sustained release of nitrous acid, self-decomposition of nitrous acid, oxidization/reduction of nitrous acid, and reduction of nitrite ions/nitrate ions thereby sustainably releasing off nitrogenous gases.

14 Claims, 17 Drawing Sheets

(56) References Cited

OTHER PUBLICATIONS

Ishihara, S. et al., "Controlled release of H2S and NO gases through CO2-stimulated anion exchange", Nature Communications, Jan. 2020, vol. 11, article No. 453, abstract.
International Search Report issued for the International Application No. PCT/JP2020/015001 on Jun. 23, 2020.
Cao et al., "Multifunctional inhibition based on layered double hydroxides to comprehensively control corrosion of carbon steel in concrete" Corrosion Science 126 (2017) 166-179.
Xu et al., "Chloride removal and corrosion inhibitions of nitrate, nitrite-intercalated Mg—Al layered double hydroxides on steel in saturated calcium hydroxide solution" Applied Clay Science 163 (2018) 129-136.
Supplementary Search Report issued for the counterpart EP application No. 20792052.1 on Mar. 31, 2023.
Berber et al. "A sustained controlled release formulation of soil nitrogen based on nitrate-layered double hydroxide nanoparticle material" J Soils Sediments (2014) 14:60-66.
Office Action issued for the counterpart CN patent application No. 2020800299657 on Feb. 4, 2023.

* cited by examiner

FIG.14
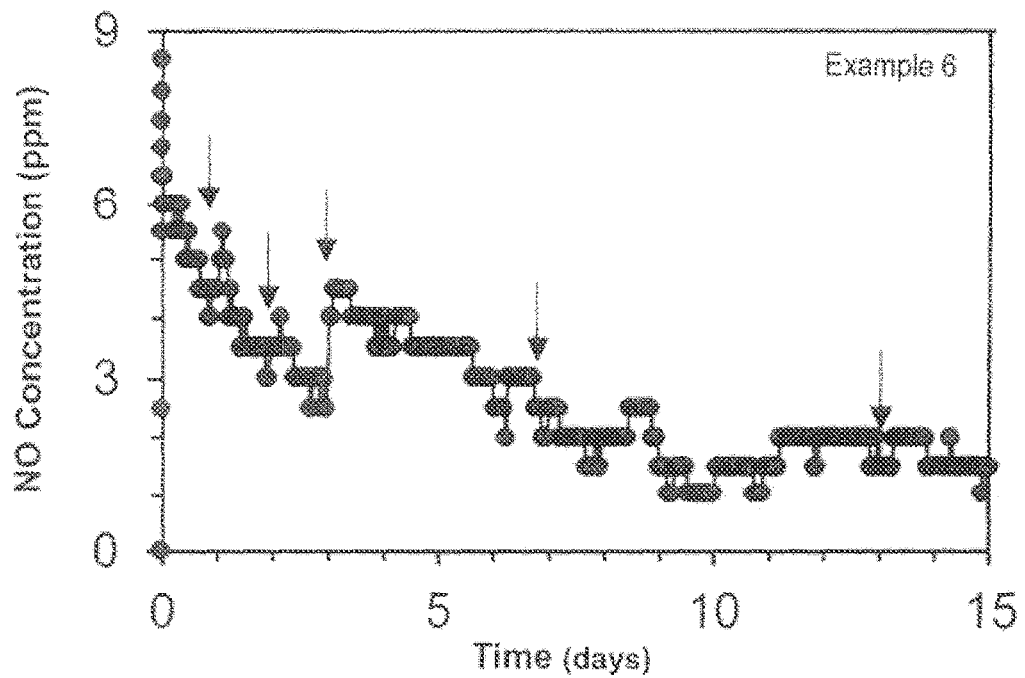
FIG.15(a)
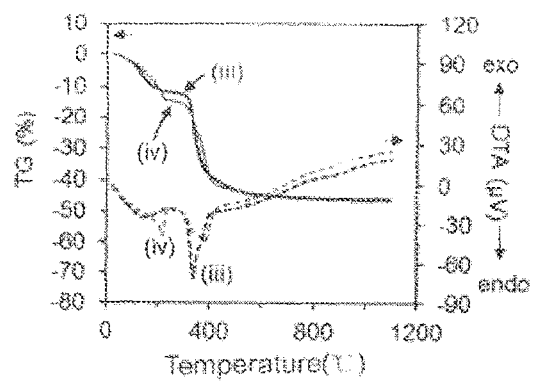
FIG.15(b)
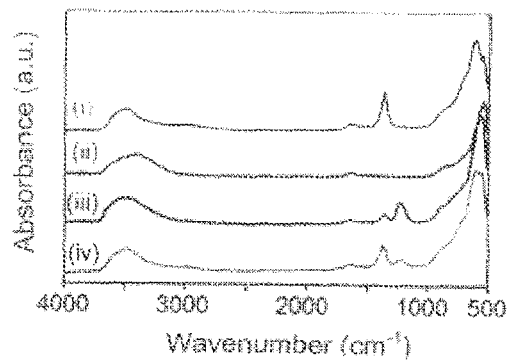
FIG.15(c)
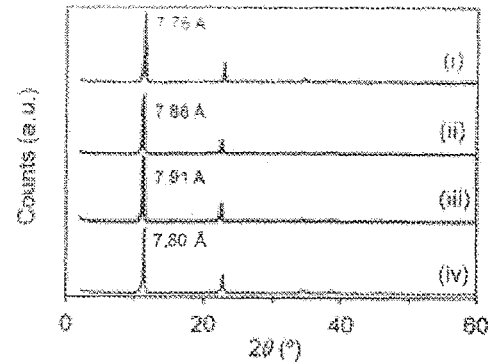
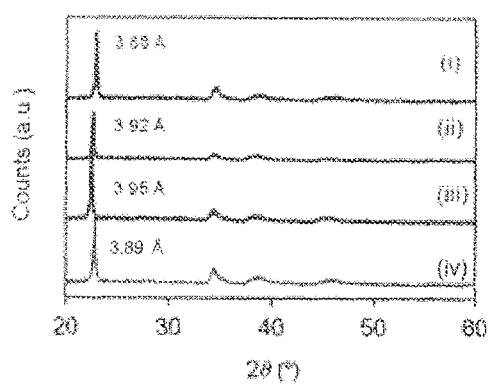

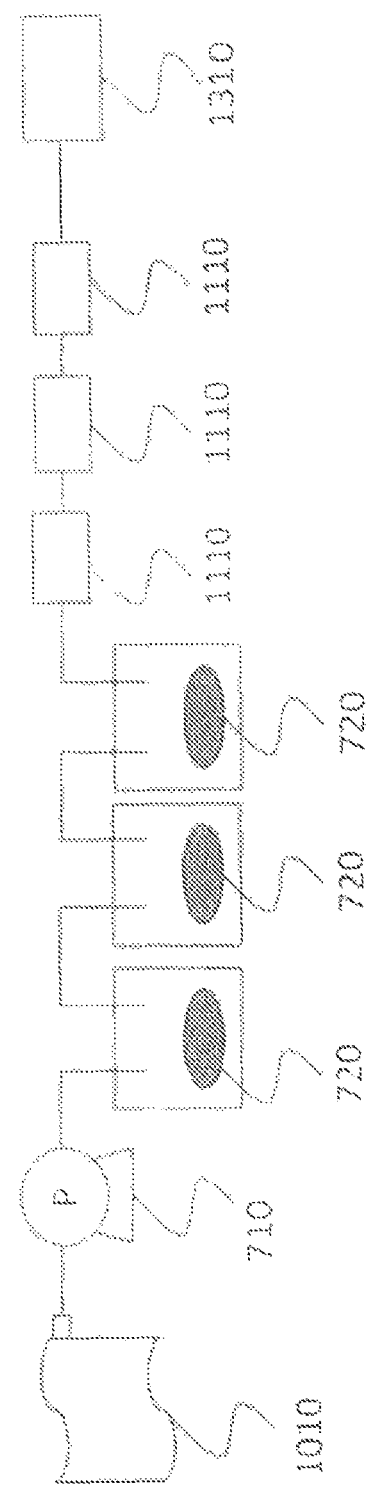

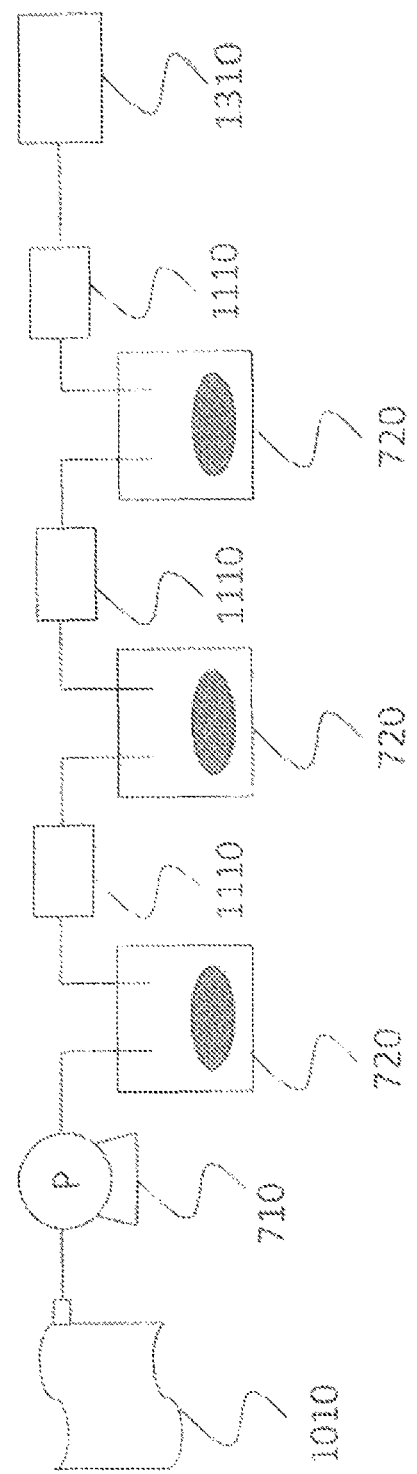

FIG.18
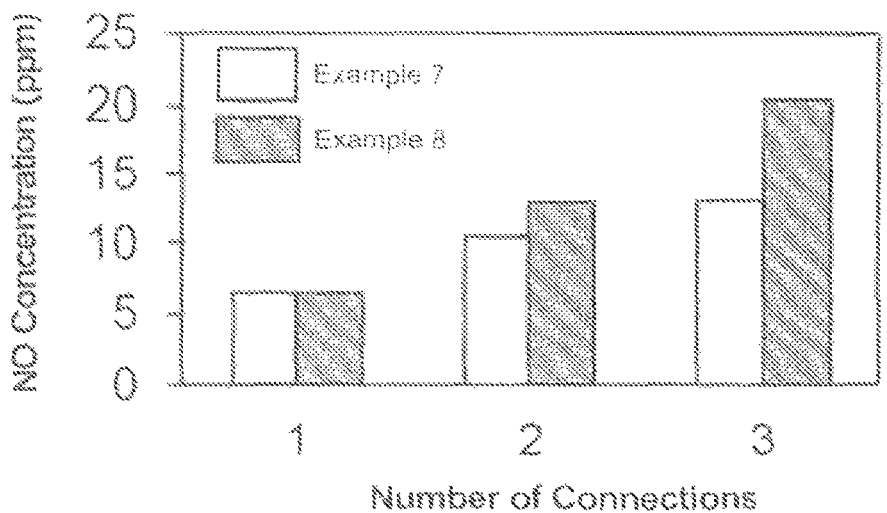
FIG.19
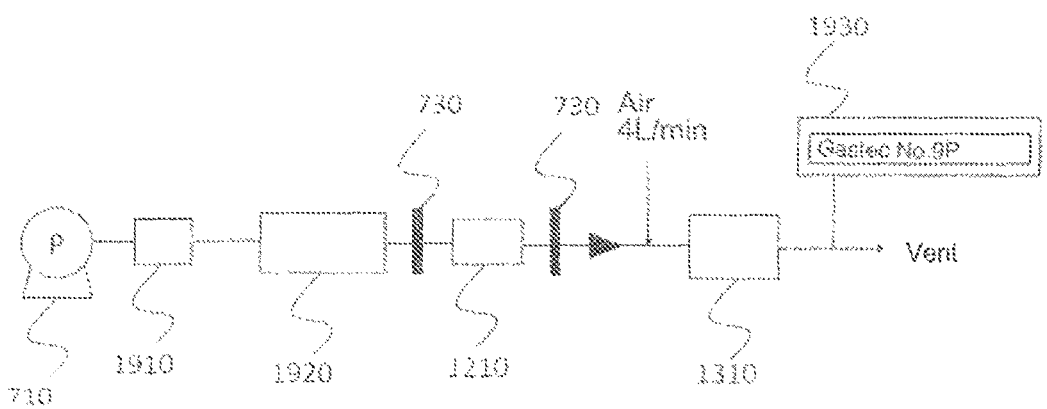
FIG.20
Example 9
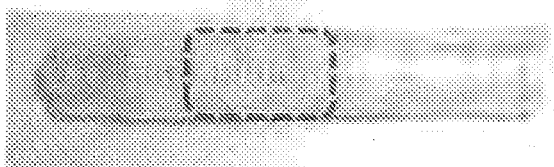
Before use
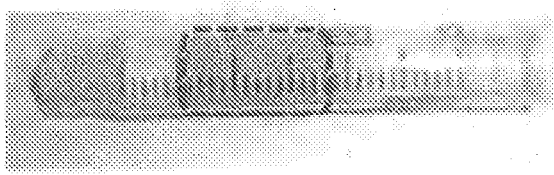
After use FIG.28
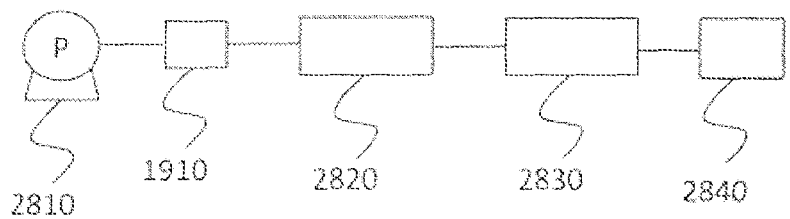
FIG.29(a)                    FIG.29(b)
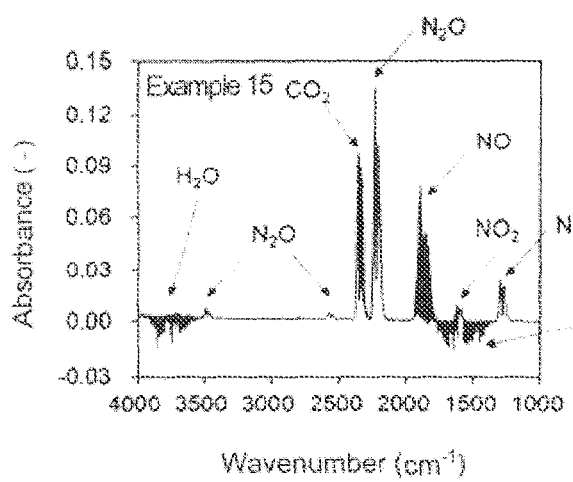    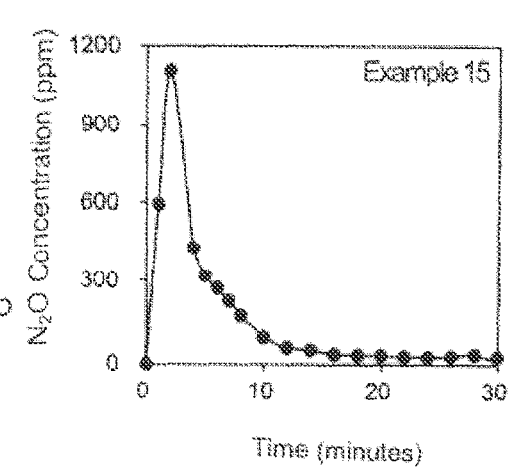
FIG.29(c)
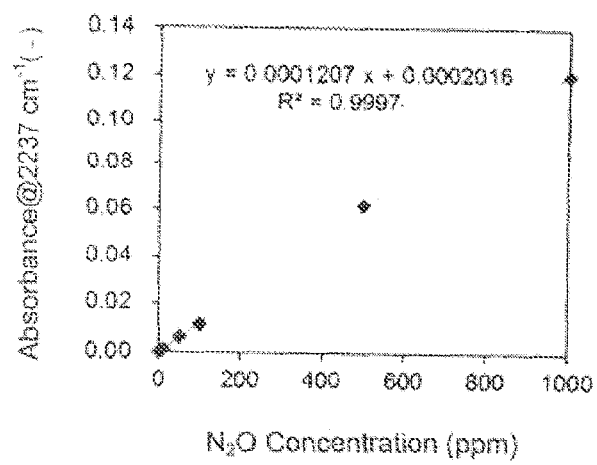

NITROGENOUS GAS SUSTAINED RELEASING AGENT AND NITROGENOUS GAS SUSTAINED RELEASER COMPOSED OF THE SAME AS WELL AS NITROGENOUS GAS SUSTAINED RELEASING METHOD, RESPIRATORY EQUIPMENT, PACKAGE, AND SUSTAINED RELEASING APPARATUS USING THE SUSTAINED RELEASER

TECHNICAL FIELD

The present invention relates to a nitrogenous gas sustained releasing agent comprising a layered double hydroxide, a nitrogenous gas sustained releasing method using the same, and respiratory equipment, package and sustained releasing apparatus using the same.

BACKGROUND ART

In the present disclosure, inorganic molecular species that contain nitrogen atoms and are in a gaseous state at normal temperature and pressure like nitrogen oxide (NOX) such as nitrogen monoxide (NO), nitrogen dioxide ($NO_2$), nitrous oxide ($N_2O$) and dinitrogen trioxide ($N_2O_3$), and oxo-acid vapors of nitrogen such as nitrous acid ($HNO_2$) and nitric acid ($HNO_3$) are generally called the "nitrogenous gas or gases".

As known in the art, a nitrogen oxide is a harmful gaseous component also called the NOx, which is contained in combustion gases generated out of cars, factories or the like, not only giving rise to photochemical smog and acid rain but also inducing respiratory diseases like asthma. The nitrogen oxide includes a variety of chemical species (for example, nitrogen monoxide, nitrogen dioxide, nitrous oxide, dinitrogen trioxide).

In recent years, it has been revealed that among the nitrogen oxides, there is a gas that shows a unique physiological action to a living body upon dosed in slight amounts. For this reason, studies about actions of such a nitrogen oxide on living bodies and tissues are intensively made, and wide applications of the nitrogen oxide to medical treatments are now under investigation. Since nitrogen monoxide (NO) in particular has been found out to have vasodilator action, it has attracted attention about its medical application, and a nitrogen monoxide inhalation method using nitrogen monoxide has been employed for treatment of severe respiratory failure associated with pulmonary hypertension (for instance, neonatal persistent pulmonary hypertension (see Non-Patent Publication 1).

However, nitrogen monoxide is a gas at normal temperature and pressure, so it is often supplied from a pressure bomb in use. In such a usage mode, it would not be easy to deliver and install the gas bomb due to its capacity and weight, and if there is an error in the gas flow rate and concentration control, it then leads to a severe accident. For this reason, the medical application of nitrogen monoxide has been limited to within a well equipped hospital. In general, there are a variety of related laws and regulations in association with handling of high pressure gases, and there are some limitations on its carrying and handling.

In addition, nitrogen atoms are present in various oxidized states; attention should also be paid to the stability of nitrogen oxides. This is particularly true of nitrogen monoxide, because of turning easily into harmful nitrogen dioxide by way of its reaction with oxygen in the air; when it is used in the field, there is the need of using advanced medical equipment to gain careful control and monitoring of the concentrations of nitrogen monoxide and nitrogen dioxide.

In such situations, a drug preparation capable of releasing off nitrogen monoxide is now under development as means for feeding nitrogen monoxide in place of the pressure bomb. Most of such drug preparations are an organic or inorganic solid compound having a working mechanism in which they act directly applied to a living body to cause hydrolysis and oxidization/reduction, generating nitrogen monoxide in the body. A representative example is nitroglycerine, isoamyl nitrite, and sodium nitrite.

Generally speaking, however, nitrogen monoxide generated in the body by way of application of the drug preparation capable of releasing off nitrogen monoxide leads to relaxation of the whole blood vessel in the body, resulting in another problem: a systemic hypotension. When air containing nitrogen monoxide in a concentration of about 1 to 40 ppm is inhaled directly into the lung, on the other hand, it expands the pulmonary blood vessels and reduces the lung blood pressure, after which it is taken up in the blood vessels from the lung for instantaneous linking to blood hemoglobin, ending up with generation of methemoglobin and deactivation. As a result, only the lung blood pressure is selectively reduced down, leading to an improvement in oxygen uptake capacity. A nitrogen monoxide inhalation method making use of this action is selectively and efficiently applied to treatment of severe respiratory failure associated with pulmonary hypertension (for instance, persistent pulmonary hypertension of the newborn).

As another nitrogen monoxide feeding means useable in lieu of the pressure bomb, it has been known to harness reaction of copper with dilute nitric acid, reaction of sodium nitrite with sulfuric acid and iron (II) sulfate or the like. With these means, however, not only is there a safety problem arising from use of high-reactive chemical substances, but also there is another problem: a lack of nitrogen monoxide sustained releasability and difficulty in control of concentration and releasing time. For this reason, nitrogen monoxide feeding means relying upon such methods has attracted no or little attention as a substitute for the pressure bomb.

From long ago, it has also been known to generate nitrogen monoxide using arc discharge without recourse to the aforesaid nitrogen monoxide generation method (see Non-Patent Publication 2). With the nitrogen monoxide generation method by way of arc discharge, however, it is needed to gain precise control of various conditions inclusive of electric current and voltage for the purpose of gaining control of concentration and releasing time; whether or not devices and power sources (batteries, etc.) normally operate must be checked up with regular maintenance. In addition, arc discharge sets off simultaneous creation of impurities more irritable to the body tissue such as nitrogen dioxide and ozone ($O_3$), which must be removed by combined use of chemical substances such as adsorbents.

If some gas feeding means using a solid material capable of releasing off nitrogenous gases in a sustained fashion are developed in place of gas supply relying upon a pressure bomb, chemical reactions using hazard reagents, and arc discharge, it is then expectable to assemble lightweight, compact and simple gas sustained releasing means that would then contribute more to a variety of research fields. In particular, if there is a solid material obtained which is capable of releasing off unstable and difficult-to-handle nitrogen monoxide in a sustained manner, it is then possible to carry out inhalation of nitrogen monoxide both at home and in medically less equipped developing countries, resulting in more contribution to a variety of medical applications. However, there is no report at all about an inorganic solid material that is capable of sustainably releasing off low-concentration nitrogen monoxide at normal temperature in the air and safe to handle. For instance, there has been a proposal put forward of a solid material capable of releasing off nitrogen monoxide by way of a mechanism (ligand exchange) of exchanging nitrogen monoxide with atmospheric water molecules while nitrogen monoxide remains adsorbed onto the unsaturated metal site of a porous material (zeolite or metal-organic-framework) (see Non-Patent Publication 6). However, there would still be a serious safety concern because high-concentration nitrogen monoxide is often released off in the initial releasing stage.

PRIOR ARTS

Non-Patent Publications

Non-Patent Publication 1: J. D. Roberts et al., "Inhaled nitric oxide and persistent pulmonary hypertension of the newborn", N. Eng. J. Med., 1997, Vol. 336, p. 605-610
Non-Patent Publication 2: B. Yu et al., "Producing nitric oxide by pulsed electrical discharge in air for portable inhalation therapy", Sci. Transl. Med. 2015, Vol. 7, 7,294ra107
Non-Patent Publication 3: N. Iyi et al., "Effect of KBr on the FTIR Spectra of $NO_3$-LDHs (Layered Double Hydroxides)", Chem. Lett. 2009, Vol. 38, 808-809
Non-Patent Publication 4: N. Iyi et al., "Factors influencing the hydration of layered double hydroxides (LDHs) and the appearance of an intermediate second staging phase", Applied Clay Science 2007, Vol. 35, 218-227
Non-Patent Publication 5: N. Iyi et al., "Efficient decarbonation of carbonate-type layered double hydroxide ($CO_3^{2-}$ LDH) by ammonium salts in alcohol medium", Applied Clay Science 2012, Vol. 65-66, 121-127 Non-Patent Publication 6: E. D. Bloch et al., "Gradual release of strongly bound nitric oxide from $Fe_2$ $(NO)_2$ (dobdc)", J. Am. Chem. Soc., 2015, Vol. 137, p. 3466-3469

SUMMARY OF THE INVENTION

Subjects of the Invention

Most nitrogenous gases are unstable and difficult to handle; if a solid material capable of releasing off them in a sustained manner, it would be efficiently used in a variety of research fields as a nitrogenous gas feeding means in place of means making use of a pressure bomb or chemical reactions of hazardous reagents. In particular, if there is a solid material obtained which is capable of releasing off unstable and difficult-to-handle nitrogen monoxide in a sustained manner, it is then possible to carry out inhalation of nitrogen monoxide both at home and in medically less equipped developing countries, resulting in more contribution to a variety of medical applications. However, there is no report at all about an inorganic solid material that is capable of sustainably releasing off low-concentration nitrogen monoxide at normal temperature in the air and safe to handle.

Accordingly, it is an object of the invention to provide a nitrogenous gas sustained releasing agent that is capable of sustainably releasing off a nitrogenous gas at normal temperature in the air and safe to handle, and a nitrogenous gas sustained releaser composed of the same as well as a nitrogenous gas sustained releasing method, respiratory equipment, and package, and an apparatus adapted to release off a nitrogenous gas in a sustained manner using the same.

Embodiments of the Invention

The inventors have focused on a layered double hydroxide (LDH) as a solid material capable of sustainably releasing off nitrogenous gases. The inventors have already found a hydrogen sulfide sustained releaser using a layered double hydroxide (LDH) including sulfide ions (e.g., $HS^-$) between layers as an inorganic solid material capable of sustainably releasing off hydrogen sulfide at normal temperature in the air, for which a patent application was filed (Japanese Patent Application No. 2018-132081). In this layered double hydroxide (LDH), the interlayer sulfide ions (e.g., $HS^-$) are subjected to anion exchange with atmospheric water or carbon dioxide to release off a hydrogen sulfide gas in a sustained manner. A specification of the patent application states that by controlling of the composition and synthesis conditions of LDH, the sustained releasing concentration and time can be controlled. If the layered double hydroxide (LDH) can be used for sustainably releasing off nitrogenous gases, the aforesaid problems could likely be solved.

As is the case with nitrogen monoxide, if other nitrogenous gases can be sustainably released off by use of the layered double hydroxide (LDH) in a simple yet safe manner with the concentration and time placed under control, it can then be efficiently used in a variety of research fields as a nitrogenous gas feeding means in place of means using a gas bomb, and chemical reactions of dangerous reagents. In addition, the total amount of gases released out of the layered double hydroxide (LDH) does not exceed beyond the material amount of effective ingredients contained in the layered double hydroxide (LHD) used so that a distinct upper limit can be placed on the total or gross amount of the gases to be released off, making sure much higher safety.

With the following features of the layered double hydroxides (LDHs) in mind, the inventors have focused on a layered double hydroxide (LDH) having a nitrogenous gas providing source included between the layers as a candidate of inorganic solid materials likely to release off nitrogenous gases.

Unlike most of other inorganic layered compounds, the LDH is a rare layered inorganic solid material capable of interlayer inclusion of anions because each layer is positively charged, and it is capable of exchanging interlayer anions, it becomes a host for inorganic or organic anions. Another merit of the LDH is having a lot of material design options because of being capable of varying layer charge density, and varying features such as ion exchangeability and crystal size. For these reasons, the LDH would be considered suitable for interlayer inclusion of anion species of a nitrogenous gas source.

The anion species providing the aforesaid nitrogenous gas source are included in a two-dimensional space having a basal plane spacing of about 1 nm. To allow external molecules or ions of LDH to come in contact with said anion species for interaction, they should essentially diffuse in said two-dimensional space. For this reason, the anion species providing the nitrogenous gas source do not immediately react with the external molecules or ions of LDH; in most cases, the reaction involved proceeds with diffusion as rate determination. Therefore, the LDH would possibly provide a promising material allowing a low-concentration nitrogenous gas to be sustainably released over an extended period of time.

Further, the LDH behaves such that when it is placed in the air with a weak acid conjugate base as the interlayer anion, said conjugate base is protonated into a weak acid molecule and an anion site is substituted by a carbonate ion ($CO_3^{2-}$) in the air under the action of carbonic acid ($H_2CO_3$) generated by reaction of an interlayer carbon dioxide ($CO_2$) with interlayer water ($H_2O$). When said weak acid molecule is volatile, it is released off in the air (Japanese Patent Application No. 2018-132081 specification). In this system, too, it is likely that similar mechanisms work.

Referring here to hydrogen sulfide ($H_2S$) that is released off as reported in Japanese Patent Application No. 2018-132081 specification, however, it is generated by addition of protons ($H^+$) to the associated stable anion species ($HS^-$), and the anion species subjected to interlayer insertion is an anion formed by removing the protons out of the end gas species. Referring to a lot of nitrogenous gases inclusive of nitrogen monoxide, on the other hand, a stable anion species corresponding to the conjugate base is not found because the molecule does not contain any proton to be eliminated. Accordingly, there is a problem in that it would principally be impossible to generate a nitrogenous gas by direct application of the method of Japanese Patent Application No. 2018-132081 specification wherein stable anion species that is a conjugate base of a weak acid to be intercalated between LDH layers.

The present inventors have then made a study of LDHs inclusive of an anion species capable of providing a nitrogenous gas. While nitrate ions ($NO_3^-$) are available as typical anion species, a layered double hydroxide containing the same has widely been known in the art.

However, it has not been reported that the nitrate ion-containing LDH reacts with atmospheric components to release off nitrogenous gases, because it remains stable in the air. The reason would be that the nitrate ions are hardly protonated in terms of equilibrium theory because they are a conjugate base of nitric acid that is a strong acid (pKa=–1.4) and carbonic acid formed out of atmospheric carbon dioxide and water is a weak acid. On the other hand, nitrous acid ($HNO_2$) has an acidity lower than that of nitric acid as can been seen from its pKa of about 3.4. With nitrous acid ions being its conjugate base, the present inventors have come across an idea that they are protonated by carbonic acid to form nitrous acid that can be vaporized and released off in the form of nitrous acid vapor.

For all that, nitrous acid is +3 in terms of the oxidation number of a nitrogen atom whereas nitrogen monoxide is +2; even if it is possible to prepare a material capable of generating nitrous acid vapor, this would not lead directly to the generation of other nitrogenous gases inclusive of nitrogen monoxide. Because nitrous acid is an instable acid, however, if nitrous acid is generated, there is likelihood that nitrogen monoxide may be generated by self-oxidation-reduction reaction. The present inventors have also come across an idea that if an oxidizing or reducing agent is allowed to react with released nitrous acid vapor without recourse to any self-oxidation-reduction reaction, the oxidation number of the nitrogen atom may vary, resulting in the formation of various nitrogenous gases inclusive of nitrogen monoxide.

First of all, the present inventors could have found through a study of an LDH synthesized with an interlayer nitrous acid ion ($NO_2^-$) that nitrous acid vapor can be sustainably released off by contact with the air at normal temperature. The present inventors could have also identified that the sustainably released nitrous acid can form nitrogen monoxide and nitrogen dioxide by way of self-oxidation-reduction reaction, and that the purity of nitrogen monoxide can be made high by removal of nitrous acid vapor and nitrogen dioxide from the post-reaction mixture.

To add to this, the present inventors could have identified that if the sustainably released nitrous acid vapor is allowed to come into contact with a proper oxidizing/reducing agent, it can be converted into just only nitrogen monoxide but also various nitrogenous gases (such as nitrous oxide, nitrogen dioxide and ammonia). More specifically, the present inventors have found that a material capable of reacting with atmospheric carbon dioxide and/or water to sustainably release off nitrous acid vapor is combined with an oxidizing agent or a reducing agent into a composite system thereby obtaining a sustained releasing agent for sustainably releasing off various nitrogenous gases via a two-stage reaction and providing a solution to the aforesaid problems by use of the same, arriving at the present invention.

As reported in the art, on the other hand, the LDH behaves such that when it is mixed with a solid salt, anion exchange reaction makes progress between solid phases so that anions between the LDH layers are released out of the LDH while anions derived from the solid salt are inserted between the LDH layers (see Non-Patent Publication 3). Referring specifically to this, as an LDH including nitrate anions between layers is mixed with KBr, it causes solid-phase anion exchange reaction to make so progress that $Br^-$ is inserted between LDH layers while LDH interlayer nitrate anions are released out of the LDH into the KBr phase. As reported in the art, this solid phase-solid phase anion exchange reaction is accelerated with an increase in the relative humidity in a mixing atmosphere; this may be considered as anion exchange responsive to water vapor.

If the LDH including anion species of the nitrogenous gas releases off said anion species by way of such solid phase-solid phase anion exchange reaction as described above so that said anion species are converted into nitrogenous gases by way of contact with a reaction reagent (e.g., an oxidizing agent and a reducing agent) on the outside of LDH, it is then possible to design an admixture material capable of sustainably releasing off nitrogenous gases by way of contact with a water vapor-containing gas. This admixture material is also expected to gain control of sustained releasing concentration and time by way of regulation of the amount of water vapor contained in the gas to contact with.

Indeed, the present inventors have synthesized an LDH containing nitrite ions and/or nitrate ions between layers and found that as a result of mixing this LDH with a reducing agent containing iron (II) sulfate that is a solid salt for contact with a water vapor-containing gas, various nitrogenous gases inclusive of nitrogen monoxide are generated. The iron (II) sulfate used as a solid salt behaves as a solid salt containing sulfate anions ($SO_4^{2-}$) having high an affinity for LDH while divalent iron ions ($Fe^{2+}$) work as a reducing agent.

The nitrogenous gas sustained releasing agent according to the invention disclosed herein is capable of reacting with carbon dioxide and water vapor contained in the air to release off nitrogenous gases; before use, it is preferably provided as a package wherein it is sealed and enclosed by a packaging or wrapping material for the purpose of blocking its contact with the air. For the purpose of holding back releasing of nitrogenous gases in the package, it is more preferable to keep the package in a voidless state or in a vacuum state by vacuum sealing, or in an inert gas or dry atmosphere. The "voidless state" is a term indicative of a state where the wrapping material is soft and the interior volume of the package is reduced to a half or less than the original volume by vacuum sealing, whereas the "vacuum state" is a term indicative of a state where the wrapping material is hard and the interior pressure of the packaging material is reduced by vacuum sealing to a half or less than the atmospheric pressure.

From the foregoing, the present inventors have arrived at the following inventive embodiments.

A sustained releasing agent capable of sustainably releasing off a nitrogenous gas according to the invention contains a layered double hydroxide having a nitrite ion ($NO_2^-$) and/or a nitrate ion ($NO_3^-$) included between layers, whereby the aforesaid objects are achieved.

The aforesaid nitrogenous gases may be at least one gas selected from the group consisting of a nitrogen monoxide gas (NO), nitrous acid vapor ($HNO_2$), a nitrogen dioxide gas ($NO_2$), a nitrous oxide gas ($N_2O$), and ammonia ($NH_3$) The aforesaid layered double hydroxide may be represented by the following general formula (1):

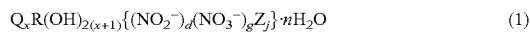

$$Q_x R(OH)_{2(x+1)}\{(NO_2^-)_d(NO_3^-)_g Z_j\} \cdot nH_2O \quad (1)$$

where Q is a divalent metal ion, R is a trivalent metal ion, Z is an anion other than $NO_2^-$ and $NO_3^-$, and each of x, d, g and j is a number that satisfies $1.8 \leq x \leq 4.2$, $0.01 \leq d+g \leq 2.0$ and $0 \leq j \leq 1.0$, and n is a number that changes depending on an environmental humidity.

In the aforesaid general formula (1), the aforesaid Q may be at least one selected from the group consisting of $Mg^{2+}$, $Mn^{2+}$, $Fe^{2+}$, $Co^{2+}$, $Ni^{2+}$, $Cu^{2+}$, $Zn^{2+}$ and $Ca^{2+}$, and the aforesaid R may be at least one selected from the group consisting of $Al^{3+}$, $Ga^{3+}$, $Cr^{3+}$, $Mn^{3+}$, $Fe^{3+}$, $Co^{3+}$ and $Ni^{3+}$.

In the aforesaid general formula (1), the aforesaid Q may be $Mg^{2+}$, and the aforesaid R may be $Al^{3+}$.

A sustained releaser for nitrogenous gases may be composed of the aforesaid sustained releasing agent.

The aforesaid sustained releaser may further contain a solid reducing agent and/or a solid oxidizing agent.

In the aforesaid sustained releaser, the aforesaid releasing agent may be mixed with the aforesaid solid reducing agent or the aforesaid solid oxidizing agent.

The aforesaid solid reducing agent may contain at least a divalent iron ion or a divalent tin ion.

The aforesaid solid reducing agent may be at least one selected from the group consisting of iron (II) sulfate, tin (II) chloride, and zinc.

The aforesaid solid reducing agent or the aforesaid solid oxidizing agent may be mixed with the aforesaid layered double hydroxide in an amount of 10% by mass to 10000% by mass inclusive.

A nitrogenous gas sustained releasing method according to the invention makes use of the nitrogenous gas sustained releaser composed of a sustained releasing agent that contains a layered double hydroxide having a nitrite ion ($NO_2^-$) and/or a nitrate ion ($NO_3^-$) included between layers to sustainably release off a nitrogenous gas, whereby the aforesaid objects are achievable.

A layered double hydroxide having at least a nitrite ion ($NO_2^-$) between layers may be used as the aforesaid layered double hydroxide, and the sustained releasing method may further include a step of bringing a gas containing carbon dioxide and/or water vapor into contact with the aforesaid releaser.

The sustained releasing method may further include a step in which nitrous acid vapor obtained in the aforesaid gas contact step is brought into contact with a solid reducing agent or a solid oxidizing agent.

A mixture of the aforesaid releasing agent with a solid reducing agent or a solid oxidizing agent may be used as the aforesaid sustained releaser, and the sustained releasing method may further include a step of bringing a gas containing at least water vapor into contact with the aforesaid releaser.

The sustained releasing method may further include a step of removing impurities in a gas sustainably released out of the aforesaid releaser using an adsorbent.

The aforesaid adsorbent may contain magnesium hydroxide or calcium hydroxide.

The medical respiratory equipment according to the invention comprises the aforesaid sustained releaser whereby the aforesaid object is achieved.

The package according to the invention includes the aforesaid releaser and a packaging or wrapping material adapted to pack or contain the aforesaid releaser in a sealed manner, whereby the aforesaid object is achievable.

An atmosphere selected from the group consisting of a voidless atmosphere, a vacuum atmosphere, an inert gas atmosphere and a dry atmosphere may be filled in the aforesaid wrapping material.

The apparatus of sustainably releasing off a nitrogenous gas according to the invention comprises an atmospheric gas feeding portion adapted to feed an atmospheric gas and a nitrogenous gas sustained releasing portion adapted to sustainably release off a nitrogenous gas by the atmospheric gas fed from the aforesaid atmospheric gas feeding portion, wherein the aforesaid nitrogenous gas sustained releasing portion comprises a nitrogenous gas releaser composed of a sustained releasing agent containing a layered double hydroxide having a nitrite ion ($NO_2^-$) and/or a nitrate ion ($NO_3^-$) included between layers and being capable of sustainably releasing off nitrogenous gases, whereby the aforesaid object is achieved.

The apparatus disclosed herein may further comprise an impurity removal portion adapted to remove impurities in the aforesaid nitrogenous gases released out of the aforesaid nitrogenous gas sustained releasing portion in a sustained manner.

The aforesaid sustained releaser may further contain a solid reducing agent or a solid oxidizing agent, which may be in admixture with the aforesaid sustained releasing agent.

The aforesaid atmospheric gas feeding portion may be adapted to feed a gas containing at least water vapor.

The aforesaid sustained releaser may further comprise a solid reducing agent or a solid oxidizing agent in the rear stage of the aforesaid sustained releasing agent.

The aforesaid atmospheric gas feeding portion may be applied to feed a gas containing at least water vapor or carbon dioxide.

The aforesaid nitrogenous gases may be nitrogen monoxide.

Advantages of the Invention

The nitrogenous gas sustained releasing agent according to the invention comprises a layered double hydroxide having a nitrite ion ($NO_2^-$) and/or a nitrate ion ($NO_2^-$) included between layers thereby releasing off a nitrogenous gas in a sustained manner. The layered double hydroxide having the aforesaid specific anions included between layers is capable of releasing off various nitrogenous gases in a sustained manner at normal temperature in the air. Further, such a layered double hydroxide is convenient to handle because of no deliquescence and enhanced safety as well. The package in which the nitrogenous gas sustained releaser composed of such a sustained releasing agent is sealed up and contained in a wrapping material is superior in terms of long-term storability and stability. If such a sustained releaser or package is used, it is then possible to provide medical respiratory equipment.

The nitrogenous gas sustained releasing method of the invention makes use of the aforesaid sustained releaser, and adoption of the aforesaid sustained releaser makes operation easy because all that is needed is contact of it with a gas containing carbon dioxide and/or water vapor when release is needed. Further, the inventive method is excellent in safety because any chemical reaction using hazardous reagents is dispensed with.

The nitrogenous gas sustained releasing apparatus according to the invention comprises an atmospheric gas feeding portion and a nitrogenous gas sustained releasing portion, wherein the aforesaid nitrogenous gas sustained releasing portion comprises a nitrogenous gas releaser composed of a sustained releasing agent containing a layered double hydroxide having a nitrite ion ($NO_2^-$) and/or a nitrate ion ($NO_3^-$) included between layers to sustainably release off nitrogenous gases. The sustained releasing apparatus of the invention may be used in place of a gas bomb. Without recourse to a power source such as a battery, the inventive sustained releasing apparatus may be designed in a compact and portable form and stored over an extended period of time as well.

BRIEF EXPLANATION OF THE DRAWINGS

FIG. 14 shows time-dependent concentration change of nitrogen monoxide released off in Example 6.

FIG. 15 shows the thermal gravimetric (TG)-differential thermal analysis (DTA) profile (FIG. 15a) and infrared absorption spectra (FIG. 15b) concerning the nitrite ion-containing LDH before and after contact with exhaled air in Example 6 as well as the powder X-ray diffraction profiles of each of the aforesaid nitrite ion-containing LDHs, and the carbonate-type LDH and Cl-type LDH used in Example 1 (FIG. 15c).

FIG. 16 is a schematic view illustrating an apparatus and experimental system used in Example 7.

FIG. 17 is a schematic view illustrating an apparatus and experimental system used in Example 8.

FIG. 18 relationship between the number of connected glass containers as well as Pasteur columns 1110 in Examples 7 and 8 and the concentration of released nitrogen monoxide.

FIG. 19 is a schematic view illustrating an apparatus and experimental system used in Example 9.

FIG. 20 shows states of a mixture in a plastic syringe 1920 before and after nitrogenous gas release experimentation in Example 9.

FIG. 28 is a schematic view illustrating an apparatus and experimental system used in Example 15.

FIG. 29 shows infrared absorption spectra of the released nitrogenous gas (FIG. 29a), time-dependent concentration change of nitrous oxide in said gas (FIG. 29b), and a relation between the concentration of nitrous oxide in said gas and absorbance of 2237 $cm^{-1}$ in infrared adsorption spectra (FIG. 29c).

MODES FOR CARRYING OUT THE INVENTION

The nitrogenous gas sustained releasing agent, the nitrogenous gas releaser composed thereof, the package using the aforesaid releaser, the nitrogenous gas sustained releasing method, the respiratory equipment and the sustained releasing apparatus according to the respective aspects of the invention (hereinafter, each aspect will often be called the "first aspect" or the like) will now be explained with reference to the accompanying drawings.

(First Aspect)

The nitrogenous gas sustained releasing agent and its preparation method according to one aspect of the invention will now be explained as the first aspect.

The nitrogenous gas sustained releasing agent according to the first aspect uses a layered double hydroxide (LDH)

having a nitrite ion and/or a nitrate ion included between its layers as an essential component.

Figure 1:
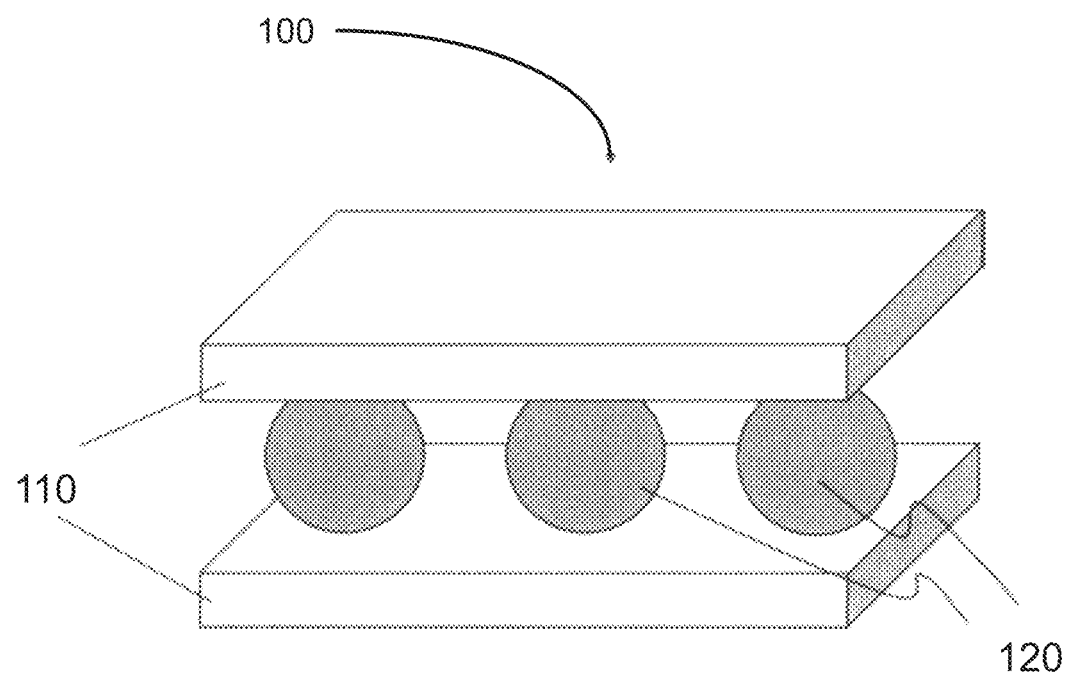
FIG. 1 is a schematic view illustrating a layered double hydroxide having anions included between layers.

FIG. 1 is a schematic view showing a structure of a layered double hydroxide (LDH) having an anion included between its layers.

The layered double hydroxide (LDH) 100 comprises layers 110, and anions 120 included between them. Each of the layers 110 is a metal hydroxide layer having positive charge. Each of the anions 120 contains at least a nitrite ion and/or a nitrate ion. All of the anions 120 may be nitrite ions ($NO_2^-$) or nitrate ions ($NO_3^-$) or, alternatively, they may contain both ions. In addition to the nitrite ion and/or the nitrate ion, the anion 120 may contain other anion(s). In what follows, the layered double hydroxide 100 will be called the "nitrite ion/nitrate ion-containing LDH" from such a point of view.

In the present disclosure, the layered double hydroxide in which the anion 120 contains at least a nitrate ion will often be called the "nitrate ion-containing LDH", and the layered double hydroxide in which the anion 120 contains at least a nitrite ion will often be called the "nitrite ion-containing LDH".

As described above, unlike a lot of other inorganic layered compounds, the LDH is one of rare inorganic compounds that can include anions 120 between layers 110 because the layer 110 has positive charge. This physical feature could allow the LDH to include anions 120 such as nitrite or nitrate ions between layers 110.

The nitrite ion/nitrate ion-containing LDH 100 is preferably represented by the following general formula (1).

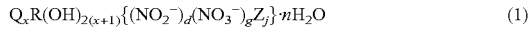

$$Q_xR(OH)_{2(x+1)}\{(NO_2^-)_d(NO_3^-)_gZ_j\}\cdot nH_2O \qquad (1)$$

In formula (1), Q is a divalent metal ion, R is a trivalent metal ion, Z is an anion other than nitrite and nitrate ions, "x", "d", "g" and "j" is a number that satisfies $1.8 \leq x \leq 4.2$, $0.01 \leq d+g \leq 2.0$ and $0 \leq j \leq 1.0$, and "n" is a number that changes depending on an environmental humidity. "$nH_2O$" is called interlayer water, and is included between the LDH layers as is the case with the anion species $\{(NO_2^-)_d(NO_3^-)_gZ_j\}$. By way of example but not by way of limitation, "n" is 0 to 4. It is here noted that while the aforesaid x range ($1.8 \leq x \leq 4.2$) is generally applied to crystalline layered double hydroxides, it is undeniably true that "x" shows a value less than 1.8 or greater than 4.2 when they contain a lot of impurities or amorphous layered double hydroxides or they are a layered double hydroxide obtained by a special synthesis process.

The "Z" in formula (1) stands for an anion derived from the starting material or solvent used for the production of nitrite ion/nitrate ion-containing LDH 100 or an atmosphere wherein the nitrite ion/nitrate ion-containing LDH 100 is produced or stored. Examples of such anions include $OH^-$, $Cr^-$, $Br^-$, $I^-$, $F^-$, $NO_3^-$, $ClO_4^-$, $SO_4^{2-}$, $CO_3^{2-}$, an acetate anion ($CH_3COO^-$), a propionate anion ($CH_3CH_2COO^-$), a lactate anion ($CH_3-CH(OH)-COO^-$), and an isethionate anion ($HOC_2H_4SO_3^-$).

In the nitrite ion/nitrate ion-containing LDH 100 represented by the aforesaid general formula (1), the aforesaid "Q" is preferably at least one selected from the group consisting of $Mg^{2+}$, $Mn^{2+}$, $Fe^{2+}$, $Co^{2+}$, $Ni^{2+}$, $Cu^{2+}$, $Zn^{2+}$ and $Ca^{2+}$, among which $Mg^{2+}$ is more preferred, and the aforesaid "R" is preferably at least one selected from the group consisting of $Al^{3+}$, $Ga^{3+}$, $Cr^{3+}$, $Mn^{3+}$, $Fe^{3+}$, $Co^{3+}$ and $Ni^{3+}$, among which $Al^{3+}$ is more preferable.

A MgAl type layered double hydroxide that is the most general solid material among layered double hydroxides is now produced in an industrial scale because it is synthesized at low costs (for instance, synthesized Hydrotalcite made by Kyowa Chemical Industry Co., Ltd.).

Referring to safety of this layered double hydroxide, its adherence to the skin or the like does not give rise to any problem at all, and it is used as gastrointestinal drugs (antacids) or the like. Further, it has been studied as a carrier for a drug delivery system (DDS) from a medical standpoint, and applied to medical fields with some achievements. For this reason, a nitrite ion/nitrate ion-containing LDH comprising the MgAl type layered double hydroxide as a fundamental structure wherein the aforesaid "Q" is $Mg^{2+}$ and the aforesaid "R" is $Al^{3+}$ could be used for medical purposes with much more enhanced safety.

The total or gross amount of the nitrogenous gas released sustainably out of the nitrogenous gas releasing agent is substantially proportional to the proportion (values of "d" and "g" in the general formula (1)) of the nitrite ion and/or nitrate ion accounting for an interlayer anion site in the nitrite ion/nitrate ion-containing LDH 100. This proportion may be varied by changing the ratio of the number of moles of nitrite ions and/or nitrate ions in a solution in contact with the LDH with respect to the number of moles of the starting LDH used for production of the nitrite ion/nitrate ion-containing LDH 100 or the LDH containing anions easy to ion exchange (easily anion-exchangeable LDH) derived from the starting LDH. When the aforesaid proportion or ratio is small, some anion component contained in the starting LDH or easy-to-anion exchange LDH remains between the layers of the nitrite ion/nitrate ion-containing LDH 100.

The sustained releasing concentration and time of nitrogenous gases may be controlled by regulation of LDH composition. The LDH composition may be regulated by varying "Q", "R", "Z", "x", "d", "g" and "j" in formula (1), and an expert in the art could make use of every possible LDH composition.

While the nitrogenous gas sustained releasing agent according to the first aspect comprises the aforesaid nitrite ion/nitrate ion-containing LDH 100 as an essential component, it is understood that the LDH may further contain various additives such as a component for regulation of sustained releasing concentration and rate, diluent, a surface coating agent, and various additives such as a component of reacting with a nitrogenous gas to form other compounds within such a range as to achieve the objects of the invention. It may be also acceptable to carry out physical processing such as wrapping using a cover tape having limited aeration thereby forming a nitrogenous gas sustained releaser according to the second aspect of the invention to be described later.

Then, how to produce the nitrogenous gas sustained releasing agent according to the first aspect of the invention as described above is explained. The nitrogenous gas sustained releasing agent according to the first aspect is obtained by synthesis of the nitrite ion/nitrate ion-containing LDH 100 by the following method or process.

Three synthetic methods: ion exchange, reconstruction, and co-precipitation are mainly applied to synthesis of the nitrite-ion/nitrate ion-containing LDH. These synthetic methods will now be explained in greater details. Here it goes without saying that other LDH synthetic methods (such as a special synthetic method wherein a solution containing given anions is added to a swollen or nano-sheeted LDH for aggregation) may also be used. As the LDH is synthesized, aging or maturing is often carried out for the purpose of enhancing crystallinity as described later; however, it is noted that a "LDH-like" compound having limited crystallinity due to poor ageing or maturing or the like may also be included in the nitrite ion/nitrate ion-containing LDH as referred to herein, if there is diffraction corresponding to a basal plane spacing (a layer-to-layer spacing) detected in powder X-ray structural analysis, and if that compound contains nitrite ions and nitrate ions providing a nitrogenous gas source.

Ion Exchange Method

How to synthesize a nitrite ion-containing LDH chosen out of nitrite ion/nitrate ion-containing LDHs is now explained in greater details. The method of synthesizing a nitrite ion-containing LDH by way of ion exchange comprises a step of providing a layered double hydroxide wherein a monovalent anion other than nitrite ion is included between layers and a solvent, a step of making the nitrite ion contained in the aforesaid solvent to prepare a solution, a step of bringing the layered double hydroxide in which a monovalent anion other than nitrite ion is included between layers into contact with the aforesaid solution, and a step of separating, washing and drying a nitrite ion-containing LDH solid matter synthesized by the aforesaid contact.

There is no limitation at all on the layered double hydroxide used as the starting material with an anion other than nitrite ion included between layers (hereafter, the layered double hydroxide called the "starting LDH"), if said anion is detached by way of ion exchange or the like. One example of such starting LDH is represented by the following formula (1)'.

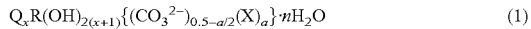

$$Q_xR(OH)_{2(x+1)}\{(CO_3^{2-})_{0.5-a/2}(X)_a\}\cdot nH_2O \quad (1)$$

In formula (1)', Q is a divalent metal ion, R is a trivalent metal ion, and X is at least one selected from the group consisting of anions having high ion exchangeability such as a chloride ion ($Cl^-$), a bromide ion ($Br^-$), a nitrate ion ($NO_3^-$), a perchlorate ion ($ClO_4^-$), a chlorate ion ($ClO_3^-$), an acetate anion ($CH_3COO^-$), a propionate anion ($CH_3CH_2COO^-$), a lactate anion ($CH_3$—$CH(OH)$—$COO^-$), and an isethionate anion ($HOC_2H_4SO_3^-$), and "x" and "a" are each a number that meets $1.8 \leq x \leq 4.2$ and $0 \leq a \leq 1$.

There is no limitation on the solvent used herein, if it can dissolve a substance that yields nitrite ions (nitrite ion source) and disperse the resulting nitrite ions in a stable manner so that they can be fed between the starting LDH layers. Such a solvent as ion exchanged water, methanol, and ethanol can be enumerated as an example. In order to ensure improved quality and consistent quality of the nitrite ions contained in a solvent and the resulting nitrite ion-containing LDH, these solvents are preferably subjected to nitrogen gas or rare gas bubbling, heating in the case of water etc., prior to the containment of nitrite ions, thereby reducing the concentration of the dissolved oxygen and carbon dioxide. In the following synthetic methods, too, it is preferable to use similarly processed solvents as the solvent such as ion exchanged water used for reaction.

The addition of nitrite ions in the solvent is carried out by addition of a substance that dissolves in said solvent to generate nitrite ions (nitrite ion source). In order to ensure improved quality and consistent quality of nitrite ions in the solvent and the resulting nitrite ion-containing LDH, the aforesaid operation is preferably carried out in an inert atmosphere. A glove box or the like filled with an inert gas may be used as means of running operation in an inert gas atmosphere. Without recourse to the glove box, it is also possible to run operation of containing nitrite ions in the solvent in an inert gas atmosphere by way of a method using a vacuum line or Schlenk tube. The inert gas atmosphere in which some of the following operations are run will not be explained any longer, because they may be carried out as mentioned above.

Although there is no limitation whatsoever on the nitrite ion source added to the solvent if it is capable of releasing off nitrite ions in the solvent, it is understood that a typical one is represented by the following general formula (2).

$$MH_P(NO_2)_q \cdot mH_2O \quad (2)$$

In formula (2), M is an alkali metal or an alkaline earth metal with the proviso that the alkaline earth metal referred to herein also includes Mg. In formula (2), p is 0 or 1, q is 1 or 2, and m is a number variable depending on a reagent preparation method and an environmental humidity. Sodium nitrite ($NaNO_2$) is mentioned as an example of the nitrite ion source represented by formula (2).

There is no limitation at all on how to bring the starting LDH in contact with the nitrite ion-containing solution as long as both are in full contact with each other to feed nitrite ions between the layers of the starting LDH. As an example, this may be achieved by pouring the aforesaid solution down into a container charged with the starting LDH, putting the aforesaid starting LDH down into a container charged with the aforesaid solution, or continuously putting the aforesaid starting LDH in a flow passage through which the aforesaid solution flows. When both are brought in contact with each other, the mixture is preferably stirred in the container for the purpose of boosting up the feeding of nitrite ions between the layers of the aforesaid starting LDH.

When an LDH having a small value of "a" in the aforesaid general formula (1)' (typically a range of $0 \leq a \leq 0.4$), that is, an LDH having a large proportion of carbonate ions ($CO_3^{2-}$) accounting for interlayer anions (hereafter, the LDH is called the "carbonate type LDH") is used as the starting LDH, it is preferable that prior to contact with the solvent, the following treatment is carried out to remove at least a part of interlayer carbonate ions between layers because they are hardly detached off.

When removing the interlayer carbonate ions, the carbonate type LDH is brought in contact with a monovalent anion ($Cl^-$, $NO_3^-$ or the like)-containing acidic compound in an alcohol according to the procedure as set forth in Japanese Patent No. 5867831 so that such LDH is converted into an easy-to-anion exchange LDH (decarbonation). Then, the easy-to-anion exchange LDH obtained by said treatment is brought in contact with a nitrite ion-containing solution (ion exchange) whereby it is exchanged with other anions in the solvent. Thus, the nitrite ion-containing LDH can be synthesized by the aforesaid decarbonation method using the carbonate type LDH as the starting material.

Figure 2:
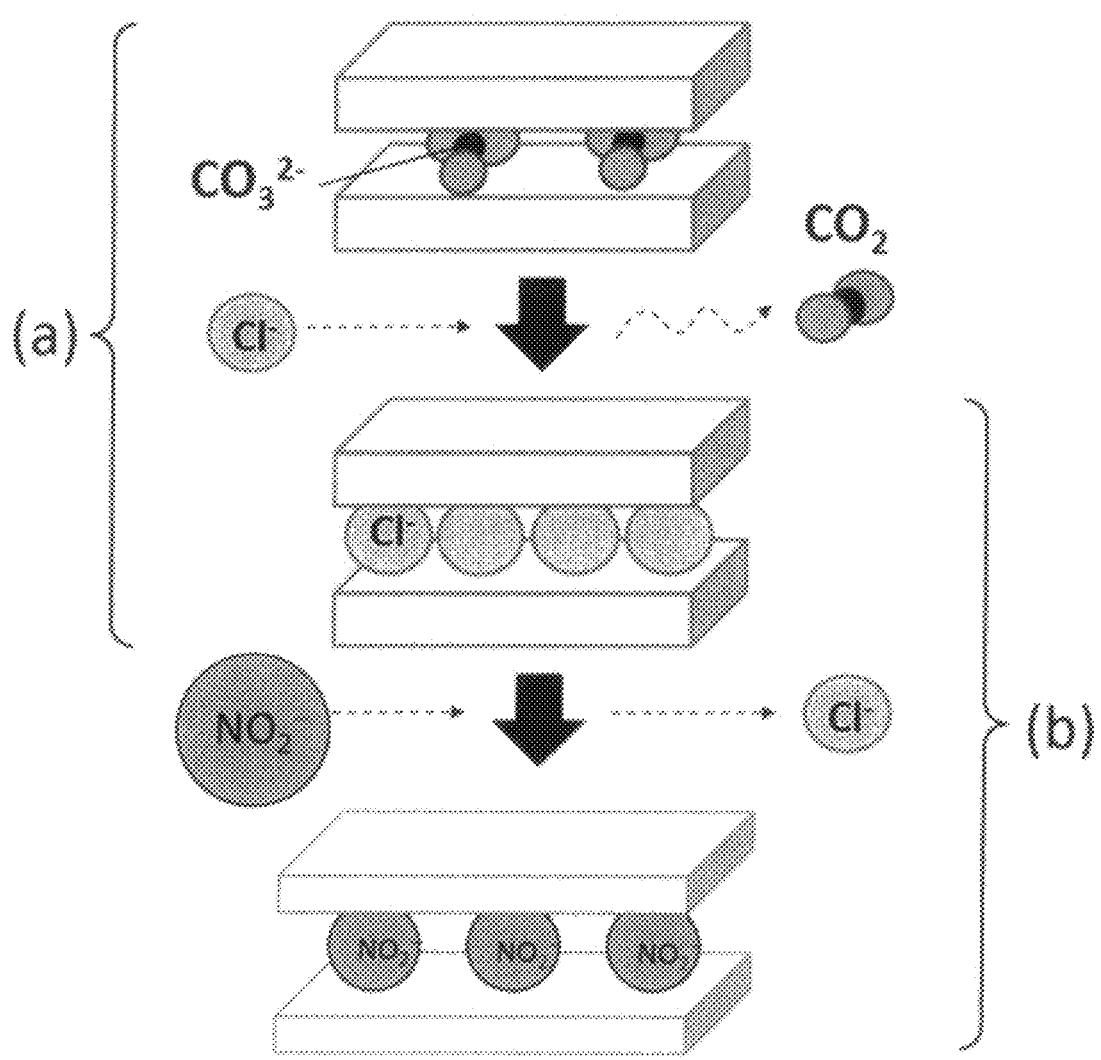
FIG. 2 is a schematic view illustrating one exemplary scheme of using a decarbonation method and an ion exchange method to synthesize a nitrite ion-containing LDH from a carbonate type LDH.

FIG. 2 is a schematic view showing an exemplary scheme of synthesizing a nitrite ion-containing LDH from a carbonate type LDH using the decarbonation and ion exchange method.

In FIG. 2, (a) shows a reaction of forming an easy-to-anion exchange LDH out of the carbonate type LDH, and (b) shows a reaction of forming a nitrite ion-containing LDH out of said easy-to-anion exchange LDH. While FIG. 2 shows that the nitrite ion-containing LDH is formed via an LDH having chloride ions included between its layers (Cl type LDH), it is understood that similar reactions take place via other easy-to-anion exchange LDHs too. In FIG. 2, (a) is also indicative of the reaction used for synthesis of a nitrate ion-containing LDH directly from the carbonate type LDH. The easy-to-anion exchange LDH obtained by full removal of carbonate ions out of the carbonate type LDH (decarbonation) is represented by the following general formula (3).

$$Q_xR(OH)_{2(x+1)}X \cdot nH_2O \quad (3)$$

In formula (3), Q is a divalent metal ion, R is a trivalent metal ion, X is a monovalent anion, "x" is a number that meets $1.8 \leq x \leq 4.2$, and "n" is a number varying depending on an environmental humidity.

The thus obtained easy-to-anion exchange LDH is allowed to come in contact with the solvent containing nitrite ions so that, as shown by (b) in FIG. 2, the interlayer anions are exchanged with nitrite ion, yielding a nitrite ion-containing LDH. When the easy-to-anion exchange LDH is a nitrate ion-containing LDH and a part of the nitrate ions exchanged with nitrite ions by such reaction as shown by (b) in FIG. 2, there is an LDH obtained with nitrite ions and nitrate ions included between its layers.

It is here noted that nitrous acid ($HNO_2$) is an acidic compound too; so if $HNO_2$ is applicable to the reaction stage shown by (a) in FIG. 2, there is then a possibility that the carbonate ions of the carbonate type LDH may be exchanged with nitrite ions in a single stage for conversion into a nitrite ion-containing LDH.

How to synthesize the nitrite ion/nitrate ion-containing LDH by introduction of nitrite ions and/or nitrate ions between layers through the "ion exchange" has been described in the foregoing.

Reconstruction Method

When the carbonate type LDH is used as the starting LDH, the "reconstruction method" may also be used in place of the aforesaid decarbonation method. In this method, a carbonate type LDH is heated to a temperature of 400° C. to 600° C. to break down a layered structure for de-carbonation, after which it is brought in contact with a solution in which the anions to be included (here nitrite ions and/or nitrate ions) are contained, followed by ageing or maturing. Contact with the solution causes the layered structure to be reconstructed while, at the same time, anions in the solvent are introduced between the layers so that the nitrite ion/nitrate ion-containing LDH can be obtained. Note here that the "ageing or maturing" means that the reaction solution is stored for a suitable period of time at room temperature while it is let standing or stirred. In LDH synthesis, ageing or maturing temperature and time are often increased for the purpose of enhancing product's crystallinity.

Coprecipitation Method

Further, there may be a method of synthesizing a nitrite ion/nitrate ion-containing LDH used, in which an aqueous solution containing a plurality of metal ion species that will form an LDH cation layer is mixed with an alkaline aqueous solution containing nitrite ions and/or nitrate ions, and the ensuing deposit or precipitate is subjected to ageing or maturing. This method, called the "coprecipitation" method, makes use of a phenomenon where an anion component in the alkaline aqueous solution used is included between layers at the time of construction of the LDH structure by coprecipitation and ageing, and finds wide use for LDH synthesis. Here note that in the coprecipitation method too, ageing or maturing temperature and time are often increased for the purpose of enhancing product's crystallinity.

In any of the aforesaid synthesis methods, although the solid nitrite ion/nitrate ion-containing LDH formed in the solution must be removed from said solution, it is noted that a generally available solid-liquid separation method such as filtration or centrifugation may be employed for separation.

The thus separated solid matter is washed with a clean solvent that is then removed for drying. For the clean solvent brought in contact with the solid matter, it is preferable to previously reduce the concentration of dissolved oxygen and carbon dioxide by nitrogen gas or rare gas bubbling or heating, as carried out in the case of synthesis.

For drying of the post-washing solid matter, a general method such as drying by heating or vacuum drying may be used, the latter being preferable in terms of prevention of deterioration of nitrite ion/nitrate ion-containing LDHs.

It is here understood that if necessary, the ensuing nitrite ion/nitrate ion-containing LDH may be mixed with various additives such as components for regulation of sustained releasing concentration and rate, diluents, surface coating agents, dehydrators, agents for elimination of carbon dioxide, deoxidants, and components of reacting with nitrogenous gases to form other compounds.

The nitrogenous gas sustained releasing agent according to the first aspect is thus obtained. This sustained releasing agent alone may provide a nitrogenous gas sustained releaser as described later (first embodiment of the second aspect). As set forth later, the obtained nitrogenous gas sustained releasing agent may be arranged side by side in such a way as to be not brought in direct contact with, or spaced away from, a reducing agent (or an oxidizing agent) to form a nitrogenous gas sustained releaser (second embodiment of the second aspect).

As also described later, the obtained nitrogenous gas sustained releasing agent may be mixed directly with a reducing agent (or an oxidizing agent) thereby forming a nitrogenous gas sustained releaser (third embodiment of the second aspect).

Second Aspect

The nitrogenous gas sustained releasing agent according to the first aspect may be provided in the form of an assembly of powders or granules, subjected to physical processing such as wrapping using a cover tape having limited gas permeability, or combined with other components or elements thereby obtaining a nitrogenous gas sustained releaser according to the second aspect of the invention. Such a sustained releaser may be exemplified by three embodiments: single use of the nitrogenous gas sustained releasing agent according to the first aspect as an effective component (first embodiment), combined use of said releasing agent and a reducing agent spaced away from the same (second embodiment), and combined use of said sustained releasing agent and a reducing agent mixed directly with the same (third embodiment). In the embodiment using the reducing agent, it is preferable to use a solid-state reducing agent because it is easy to handle when the sustained releaser is produced or utilized. Although depending on the type of the nitrogenous gas to be sustainably released off, an oxidizing agent may be used in place of said reducing agent.

An exemplary reducing agent includes an inorganic salt or inorganic compound containing a divalent iron ion, a divalent tin ion, a monovalent copper ion, and a divalent cobalt ion; a metal such as zinc or magnesium; an organic material such as sulfamic acid, hydroquinone, and ascorbic acid; an organometal; an enzyme; and a reduction electrode. For instance, if iron (II) sulfate, tin (II) chloride, zinc or sulfamic acid is allowed to react with the sustained releasing agent as the reducing agent, nitrous acid ($HNO_2$) sustainably released out of the nitrite ion/nitrate ion-containing LDH 100 is then converted or transformed into nitrogen monoxide (NO), nitrous oxide ($N_2O$), ammonia ($NH_3$) or nitrogen ($N_2$), respectively.

For a particular purpose of sustainably releasing nitrogen monoxide as the nitrogenous gas, a reducing agent containing at least a divalent iron ion is preferable, and a reducing agent containing at least iron (II) sulfate is more preferable.

An exemplary oxidizing agent includes hexavalent chromium, and oxygen ($O_2$). For instance, hexavalent chromium is allowed to reach with the releasing agent as the oxidizing agent for conversion of nitrous acid ($HNO_2$) into nitrogen dioxide ($NO_2$)

The reducing (or oxidizing) agent may be carried on a solid inorganic material such as zeolite, silica gel, and active charcoal.

The amount of such a reducing (or oxidizing) agent, on which there is no particular limitation, may come under a range of 10% by mass to 10000% by mass inclusive, or preferably within a range of 100% by mass to 1700% by mass inclusive, relative to the nitrite ion/nitrate ion-containing LDH 100. For instance, if the reducing (or oxidizing) agent is used in a small amount (no greater than 300% by mass), it is expectable that the sustained releasing time is extended in limited releasing concentrations. Within the aforesaid mass range, any desired sustained releasing concentration and time is achievable.

For the nitrogenous gas sustained releaser comprising the nitrogenous gas sustained releasing agent mixed directly with the reducing (or oxidizing) agent, it is preferable that the nitrogenous gas sustained releasing agent and the reducing (or oxidizing) agent are in a powdery form. This may cause the reaction to be boosted up to increase the sustained releasing concentration of the nitrogenous gases.

When the powdery nitrogenous gas sustained releasing agent and reducing (or oxidizing) agent are used, the area of contact may be controlled by an appropriate selection of the particle diameter of these powders. A smaller contact area causes the sustained releasing concentration to become so low that the sustained releasing time can be extended while the sustained releasing concentration is kept low. On the contrary, a larger contact area may result in an increased sustained releasing concentration. For instance, the particle diameter of the nitrogenous gas sustained releasing agent may be regulated within a range of 0.5 µm to 500 µm inclusive whereas the particle diameter of the reducing (or oxidizing) agent may be regulated within a range of 0.5 µm to 2000 µm inclusive. An LDH is a plate-like crystal in which a plane perpendicular to a stacking direction (vertical direction in the sheet plane of FIG. 1) grows; the particle diameter of the nitrogenous gas sustained releasing agent composed mainly of this crystal is provided by a median of the equivalent circle diameter or Feret's diameter of the plate-like plane of each particle (crystal). For instance, said particle diameter is provided by a mean value found from an image observed under an electron microscope such as a scanning electron microscope (SEM).

It is here noted that a reducible LDH (e.g., LDH having formula (1) where Q is a divalent iron ion) may be used as the main component nitrite ion/nitrate ion-containing LDH 100. In this case, nitrogenous gas may be released off by the nitrogenous gas sustained releaser (first embodiment) consisting only of the aforesaid nitrogenous gas sustained releasing agent, as is the case with the nitrogenous gas sustained releaser wherein the nitrite ion/nitrate ion-containing LDH 100 is mixed directly with the reducing (or oxidizing) agent (third embodiment).

In what follows, the aforesaid three sustained releasers will be explained in further details with reference to the mechanisms of releasing and sustained releasing of nitrogenous gases.

[Nitrogenous Gas Sustained Releaser According to the First Embodiment: Nitrogenous Gas Sustained Releaser Consisting Only of the Nitrite Ion/Nitrate Ion-Containing LDH]

Figure 3:
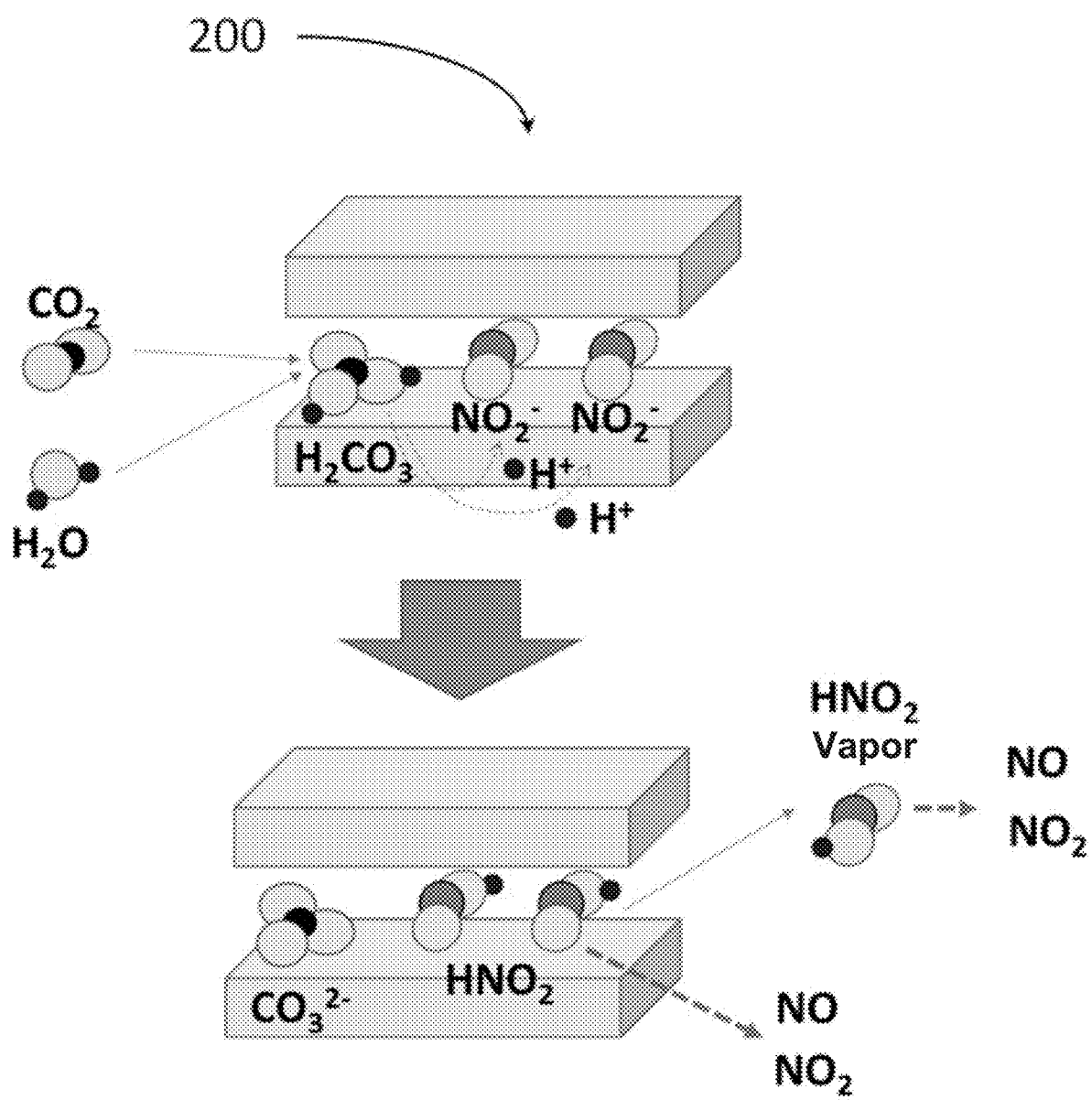
FIG. 3 is a schematic view illustrating a mechanism through which a nitrogenous gas is sustainably released from a nitrogenous gas sustained releaser composed only of a nitrogenous gas sustained releasing agent comprising a nitrite ion-containing LDH as a single component.

FIG. 3 is a schematic view showing a mechanism by which a nitrogenous gas is sustainably released out of a nitrite ion-containing LDH that is a sort of nitrite ion/nitrate ion-containing LDHs.

A nitrogenous gas sustained releaser consisting only of a nitrogenous gas sustained releasing agent composed mainly of a nitrite ion-containing LDH 200 will now be explained as the nitrogenous gas sustained releaser according to the first embodiment with reference to FIG. 3. As the nitrite ion-containing LDH 200 comes in contact with an air containing carbon dioxide and/or water vapor, it causes nitrous acid ($HNO_2$) that is a weak acid to be formed, as will be described later. Nitrous acid may take the form of nitrous acid vapor that is then vaporized. Nitrous acid, because of being an instable compound, is converted by self-oxidation-reduction reaction into nitrogen monoxide and nitrogen dioxide over time. In other words, the nitrite ion-containing LDH 200 per se works as a nitrogenous gas sustained releasing agent. The nitrogenous gas here indicates nitrous acid vapor, nitrogen monoxide and nitrogen dioxide. Further, when the releasing behavior of nitrogenous gases conforms to the "sustained releasing" to be defined later, the nitrite ion-containing LDH falls into the category of a nitrogenous gas sustained releasing agent.

The reason for using the nitrite ion-containing LDH as an element of constituting the nitrogenous gas sustained releasing agent, that is, a solid material of releasing off nitrogenous gases in a sustained manner is based on the idea that the nitrite ion-containing LDH may possibly release off nitrogenous gases in a sustained manner by way of nitrous acid formed through the following mechanism of action. This reaction is now explained using a chemical formula.

As described in Japanese Patent Application No. 2018-132081, a conjugate base of a weak acid included between the LDH layers is protonated by carbonic acid ($H_2CO_3$) generated by reaction of atmospheric carbon dioxide with interlayer water yielding the corresponding weak acid molecule; said molecule, if it is volatile, may possibly be released off in the air. A nitrous acid ion ($NO_2^-$) is a conjugate base of nitrous acid ($HNO_2$) that is a weak acid; when the nitrite ion-containing LDH is placed in the air, there is nitrous acid formed between the LDH layers based on equilibrium theory, which would be released in the form of vapor in the air. The corresponding chemical reaction is represented by the following formula (4).

$$CO_2 + H_2O + 2NO_2^- \rightarrow 2HNO_2 \leftarrow + CO_3^{2-} \qquad (4)$$

Such a series of reactions may be viewed as the "solid phase-gas phase anion exchange reaction" wherein, as shown in FIG. 3, atmospheric carbon dioxide enters between the nitrite ion-containing LDH layers, reacts with interlayer water to generate protons $H^+$ and carbonate ions, and the resulting carbonate ions are subjected to anion exchange with interlayer nitrite ions while $H^+$ is combined with nitrite ions to form nitrous acid, a part of which would be released off as vapor in the air.

It is here noted that the water previously contained in the LDH may just only be used as the interlayer water ($H_2O$) reacting with carbon dioxide but also water vapor contained in the atmosphere may be used. When the water vapor contained in the atmosphere is used, the fed gas will contain carbon dioxide and water vapor according to formula (4). When the water reacting with carbon dioxide according to formula (4) is interlayer water, on the other hand, the reaction of formula (4) makes progress with the feeding of a gas containing at least carbon dioxide, resulting in releasing of nitrous acid vapor out of the nitrite ion-containing LDH.

As shown in Example 17 as described later, there is a reaction path indicated by formula (4)' present as a mechanism of releasing nitrous acid vapor unanticipated at the beginning. When the fed gas contains much water vapor, the reaction of formula (4)' makes only slight progress on the basis of equilibrium theory, ending up with nitrous acid vapor being released off and hydroxide ions (OH⁻) remaining between the LDH layers. Referring further to formula (4)', no carbon dioxide is used for releasing of nitrous acid vapor because the water molecules function as an acid of the proton supply source. With the releasing mechanism of nitrous acid vapor according to formula (4)', it is possible to release off nitrous acid vapor although in slight amounts. As the acidity of water (pKa=14.0) is lower than that of nitrous acid, however, the equilibrium of nitrous acid formation according to formula (4)' goes too far to a reaction product side (i.e., the left side of formula (4)'), resulting in less formation of nitrous acid. It is here noted that if an OH⁻ type LDH occurring from the reaction of formula (4)' comes in contact with a gas containing carbon dioxide, one carbonate ion molecule and one water molecule will then be generated by reaction of 2 OH⁻ molecules with one carbon dioxide molecule, with carbonate ions remaining between the LDH layers.

$$H_2O + 2NO_2^- \rightarrow 2HNO_2 \leftarrow + 2OH \quad (4)'$$

Essentially required for the aforesaid reactions of formulae (4) and (4)' is a diffusion process comprising entrance of gas between the layers and separation of gas out of the layers; these reactions continue over an extended period of time and would be taken as being observed in the form of nitrous acid vapor sustained release.

Nitrous acid is broken down into nitrogen monoxide (NO) and nitrogen dioxide ($NO_2$) by the self-oxidation-reduction reaction having formula (5); if nitrous acid can be generated, there is then a possibility that other nitrogenous gases such as nitrogen monoxide and nitrogen dioxide may also be generated.

$$2HNO_2 \rightarrow NO_2 + NO + H_2O \quad (5)$$

By definition, the nitrogenous gas releasability here refers to the capability of releasing nitrogenous gases to be detected by some qualitative or quantitative method in the nitrogenous gas release experimentation to be described later, and the nitrogenous gas releasing agent refers to a material capable of releasing off nitrogenous gases.

By definition, on the other hand, the nitrogenous gas sustained releasability refers to the capability of allowing a nitrogenous gas having a concentration of 1/100 or more of the maximum value to be continuously detected over 30 minutes or longer in the nitrogenous gas release experimentation to be described later or the capability of allowing nitrogenous gases having a certain concentration to be continuously detected over 30 minutes or longer within a fluctuation range of 25%. The nitrogenous gas sustained releasing agent refers to a material having the nitrogenous gas sustained releasability.

It is here understood that the material having a property of releasing off plural nitrogenous gas species at the same time serves as a releasing agent for individual nitrogenous gases. For instance, a sustained releasing agent of releasing off both nitrogen monoxide and nitrogen dioxide at the same time serves as just only a nitrogen monoxide sustained releasing agent but also a nitrogen dioxide sustained releasing agent.

A mixed gas of nitrous acid vapor, nitrogen monoxide and nitrogen dioxide is generated out of the nitrate ion-containing LDH 200 in the air by way of the chemical reactions represented by the aforesaid formula (4) and (5). Because nitrous acid, and nitrogen dioxide is an acidic gas, the mixed gas is flowed through a column loaded up with a basic adsorbent for removal of nitrous acid vapor and nitrogen dioxide, resulting in an increased purity of nitrogen monoxide. As the mixed gas is brought in contact with air for a constant time or heated, it causes the self-oxidation-reduction reaction of nitrous acid represented by formula (5) and the oxidation of nitrogen monoxide by air represented by formula (6) to make progress so that the concentration and purity of nitrogen dioxide can be enhanced. Nitrogen dioxide reacts with water, as can be seen from formulae (7) and/or (8), yielding nitric acid as well as nitrogen monoxide and/or nitrous acid.

$$2NO + O_2 \rightarrow 2NO_2 \quad (6)$$

$$3NO_2 + H_2O \rightarrow 2HNO_3 + NO \quad (7)$$

$$2NO_2 + H_2O \rightarrow HNO_3 + HNO_2 \quad (8)$$

[Nitrogenous Gas Sustained Releaser According to the Second Embodiment: Nitrogenous Gas Sustained Releaser Wherein the Nitrogenous Gas Sustained Releasing Agent is Spaced Away from, and Placed Side by Side with, a Reducing (Oxidizing) Agent]

In what follows, a nitrogenous gas sustained releaser in which a nitrogenous gas sustained releasing agent is spaced away from, and placed side by side with a reducing agent will be explained as a nitrogenous gas sustained releaser according to the second embodiment of the invention. As already described, the nitrite ion-containing LDH 200 (see FIG. 3) that is a sort of nitrite ion/nitrate ion-containing LDHs induces the "solid phase-gas phase anion exchange reaction" with atmospheric carbon dioxide and/or water thereby generating nitrous acid vapor. The nitrous acid vapor may be reduced or oxidized (by use of an appropriate reducing agent or oxidizing agent) for conversion into the desired nitrogenous gas. For instance, the nitrous acid vapor may be allowed to react with iron (II) sulfate, tin (II) chloride, hexavalent chromium, zinc, or sulfamic acid for conversion into nitrogen monoxide (NO), nitrous oxide ($N_2O$), nitrogen dioxide ($NO_2$), ammonia ($NH_3$) or nitrogen ($N_2$), respectively. The reducing (or oxidizing) agent used herein is preferably in a solid state, and more preferably free of deliquescence.

Thus, the nitrite ion-containing LDH has a property of sustainably releasing off nitrous acid vapor according to the said "solid phase-gas phase anion exchange reaction"; if the nitrous acid vapor released off in a sustained manner is converted into other nitrogenous gases by use of a reducing (or oxidizing) agent, it is then possible to sustainably releasing off nitrogenous gases other than nitrous acid vapor. In the nitrogenous gas sustained releaser according to the second embodiment based on this idea, the exemplified nitrogenous gas sustained releasing agent composed mainly of the nitrite ion-containing LDH is spaced away from, and in no physical contact with, the reducing (or oxidizing) agent. And nitrous acid vapor sustainably released out of the aforesaid nitrogenous gas sustained releasing agent arrives at the reducing (or oxidizing) agent by way of diffusion or gas flow, where it is converted into nitrogenous gases other than nitrous acid via the reduction (or oxidization) reaction to sustainably release off the desired nitrogenous gas. That is, the nitrogenous gas sustained releaser as described herein is a composite material composed of the nitrite ion-containing LDH and the reducing (or oxidizing) agent.

In the nitrogenous gas sustained releaser according to the second embodiment, every possible method ordinarily occurring to an expert in the art may be used to locate the nitrogenous gas sustained releasing agent spatially away from, and side by side with, the reducing (or oxidizing) agent in order to place under control diffusion of nitrous acid vapor and progress of chemical reaction of nitrous acid vapor with the reducing (or oxidizing) agent. Examples include an arrangement in which the nitrogenous gas sustained releasing agent and the reducing (or oxidizing) agent are disposed on an inlet side and an outlet side, respectively, of an atmospheric gas under a flowing air, an arrangement in which a gas permeable partition such as a filter is located between the nitrogenous gas sustained releasing agent and the reducing (or oxidizing) agent, and an arrangement in which the nitrogenous gas sustained releasing agent is covered with the reducing (or oxidizing) agent.

[Nitrogenous Gas Sustained Releaser According to the Third Embodiment: Nitrogenous Gas Sustained Releaser in which the Nitrogenous Gas Sustained Releasing Agent and the Reducing (or Oxidizing) Agent are Directly Mixed Together]

Figure 4:
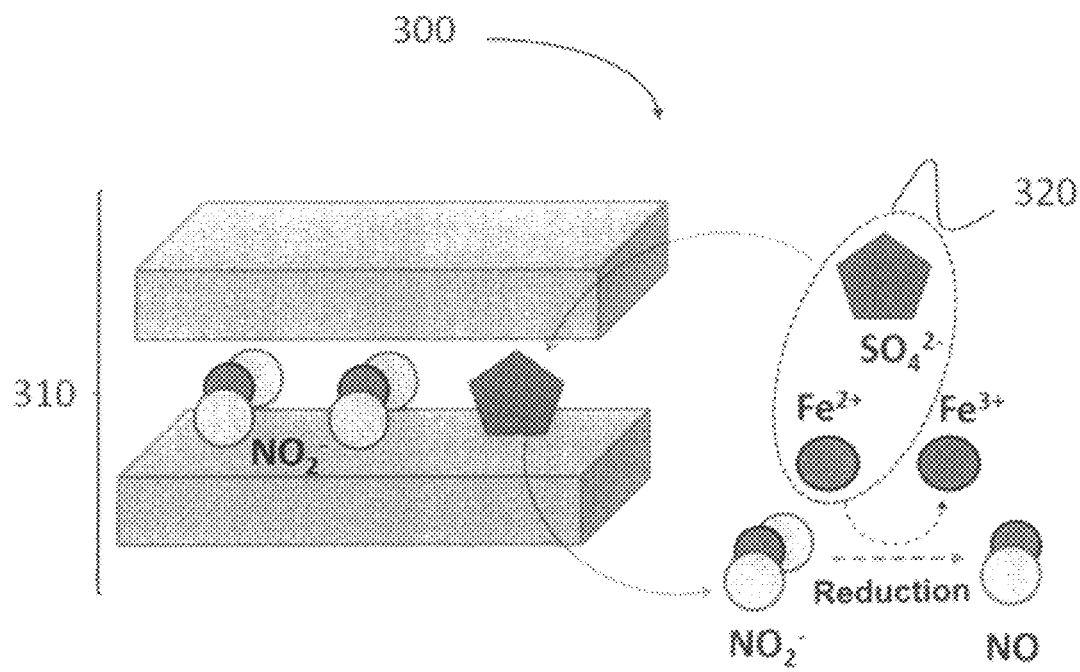
FIG. 4 is a schematic view illustrating a mechanism through which a nitrogenous gas is sustainably released from a nitrogenous gas sustained releaser comprising a nitrogenous gas sustained releasing agent composed mainly of a nitrite ion-containing LDH and a reducing agent directly mixed therewith.

FIG. 4 is a schematic view showing a mechanism by which nitrogenous gases are sustainably released out of a nitrogenous gas sustained releaser comprising a nitrogenous gas sustained releasing agent composed mainly of a nitrite ion-containing LDH that is a sort of nitrite ion/nitrate ion-containing LDHs, and a reducing agent mixed directly with the same.

With reference to FIG. 4, a nitrogenous gas sustained releaser 300 comprising a nitrogenous gas sustained releasing agent composed mainly of a nitrite ion-containing LDH 310, and a reducing agent 320 mixed directly with the same will now be explained as the nitrogenous gas sustained releaser according to the third embodiment. As already described, it has been reported (Non-Patent Publication 3) that in some cases, when the LDH is mixed with a solid salt, the solid phase-solid phase anion exchange reaction makes progress so that anions derived from the solid salt are inserted between the LDH layers whereas anions between the LDH layers are released off. Although there is no precedent for application of anion exchange reaction between the "solid phase-solid phase" in such a nitrite ion-containing LDH 310 as shown in FIG. 4 to a gas sustained releasing mechanism, the present inventors has come across an idea that anion diffusion in the LDH layers also occurs in the anion exchange between the "solid phase-solid phase" so that anion exchange makes progress over a certain time, providing useful nitrogenous gas sustained release.

There is another report mentioning about the effect that the solid phase-solid phase anion exchange reaction in the LDH is boosted up by an increase in an atmospheric relative humidity (Non-Patent Publication 3). This anion exchange may be viewed as an anion exchange reaction where start timing and progress speed can be controlled by a water vapor-containing gas as desired.

As the nitrogenous gas sustained releasing agent composed mainly of the nitrite ion-containing LDH 310 is mixed with the solid salt-containing reducing agent 320 and brought in contact with a gas containing at least water vapor, it provides sustained release of nitrogenous gases including nitrogen monoxide (NO), nitrogen dioxide ($NO_2$), nitrous acid vapor ($HNO_2$) and nitrous oxide ($N_2O$). Iron (II) sulfate shown as the reducing agent 320 in FIG. 4 is a solid salt that contains a sulfate ion ($SO_4^{2-}$) having high affinity for LDH and a divalent iron ion ($Fe^{2+}$) working as a reducing agent. Coexistence of this iron (II) sulfate with the nitrite ion-containing LDH 310 allows nitrogen monoxide to be released off in a sustained way. For this reason, the nitrogenous gas sustained releaser in which the nitrogenous gas sustained releasing agent composed mainly of the nitrite ion-containing LDH 310 is mixed with the solid salt-containing reducing agent 320 can be categorized as a nitrogen monoxide releaser. Although iron (II) sulfate is shown as the reducing agent 320 in FIG. 4, it is noted that the reducing agent is not limited thereto.

The aforesaid (sustained) nitrogen monoxide releasing reaction is represented by the following chemical formula.

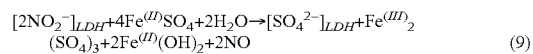

$$[2NO_2^-]_{LDH} + 4Fe^{(II)}SO_4 + 2H_2O \rightarrow [SO_4^{2-}]_{LDH} + Fe^{(III)}_2(SO_4)_3 + 2Fe^{(II)}(OH)_2 + 2NO \quad (9)$$

where "$[\ ]_{LDH}$" indicates that the bracketed matter is present between the LDH layers.

In another example, a mixture of the nitrogenous gas sustained releasing agent composed mainly of the nitrite ion-containing LDH 310 with tin (II) chloride may function as a nitrous oxide sustained releaser.

On the other hand, the nitrate ion-containing LDH that is another sort of nitrite ion/nitrate ion-containing LDHs is unlikely to release off nitric acid by way of direct reactions with water and carbon dioxide in view of equilibrium theory, because the nitrate ion is a conjugate base of nitric acid that is a strong acid. If the solid salt-containing reducing agent coexists, however, it then causes anion exchange reaction to take place between the aforesaid solid phases. Then, when the nitrate ion contained in the nitrate ion-containing LDH is released out of the LDH, this comes in contact, and reacts with, the reducing agent on the outside of the LDH so that it can be converted into nitrogenous gases. The nitrate ion-containing LDH does not release off nitric acid by way of reactions with water and carbon dioxide; a nitrogenous gas sustained releasing agent composed mainly of this LDH, and a nitrogenous gas sustained releaser formed of said releasing agent can be stored stably in the air.

In the solid phase-gas phase anion exchange, there is thus carbonic acid ($H_2CO_3$) formed so that $CO_3^{2-}$ is substituted with an interlayer anion. The acidity pKa of an acid coming from the interlayer anion is an important indicator having an influence upon sustained releasability. On the other hand, anion exchange between the solid phases takes place irrespective of pKa so that this anion exchange has a specific feature of inducing a reaction process that hardly occurs in the solid phase/gas phase anion exchange.

In this case, in order to provide efficient reduction of nitrate ions into nitrogen monoxide, it is preferable to use a reducing agent much stronger than the case of nitrite ions that is easily reducible by divalent iron ions into nitrogen monoxide. For instance, such a reducing agent includes a reducing agent obtained by mixing divalent iron ions with zinc powders, and a reducing agent obtained by mixing divalent ions with iron powders. The reducing agent for reduction of nitrate ions into the desired nitrogenous gases is not limited to them; an expert in the art could have recourse to every imaginable reducing agent.

The aforesaid reducing agent comprising a mixture of iron (II) sulfate with zinc is capable of forming a nitrogen monoxide sustained releaser by mixing it with the nitrogenous gas sustained releasing agent composed mainly of the nitrate ion-containing LDH. Further, as the released nitrogen monoxide is oxidized by oxygen in the air, it is also possible to sustainably release off nitrogen dioxide.

Thus, in the nitrogenous gas sustained releaser 300 according to the third embodiment, the nitrite ion and/or nitrate ion sustainably released out of the nitrite ion/nitrate ion-containing LDH 310 by way of the solid phase/solid phase anion exchange reaction reacts with the reducing agent 320 on the outside of the LDH layer resulting in the conversion into other nitrogenous gases that are then sustainably released off. Depending on the type of the nitrogenous gas to be sustainably released off, an oxidizing agent may be used in place of the aforesaid reducing agent.

The mixing of the nitrogenous gas sustained releasing agent with the reducing (or oxidizing) agent to obtain the nitrogenous gas sustained releaser 300 according to the third embodiment may have been carried out in advance or may be carried out just prior to contact with the gas adapted to sustainably release off the nitrogenous gases.

When the nitrogenous gas sustained releaser is previously mixed with the reducing (or oxidizing) agent, it is preferable to store the mixture of the nitrogenous gas sustained releaser with the reducing (or oxidizing) agent in a closely tight container for the purpose of preventing the solid phase/solid phase anion exchange reaction from making progress during storage. More preferably, a voidless atmosphere, a vacuum, an inert atmosphere or a dry atmosphere is used as the atmosphere filling in the closely tight container.

When the nitrogenous gas sustained releasing agent is mixed with the reducing (or oxidizing) agent just prior to contact with the gas adapted to sustainably release off the nitrogenous gases, on the other hand, at least the agent likely to react with carbon dioxide and/or moisture in the air is preferably stored in a closely tight container. More preferably, a voidless atmosphere, a vacuum, an inert atmosphere or a dry atmosphere is used as the atmosphere filling in the closely tight container. Referring specifically to how to carry out mixing, an expert in the art could have recourse to every possible method inclusive of a method in which a movable partition located between the nitrogenous gas sustained releasing agent and the reducing (or oxidizing) agent is operated to mix the nitrogenous gas sustained releasing agent with the reducing (or oxidizing) agent, or a mixing method combined with mechanical pulverization in which the nitrogenous gas sustained releasing agent and the reducing (or oxidizing) agent are mechanically pulverized and mixed together by means of such equipment as a pepper mill.

Referring to the nitrogenous gas sustained releaser in which the nitrogenous gas sustained releasing agent is directly mixed with the reducing (or oxidizing) agent, it is preferable to store both components in the same container with a partition or the like inserted into the container to space them away from each other. It is then possible not only to prevent scattering of the powdery reducing (or oxidizing) agent but also to carry out mechanical mixing operation from outside, making sure of high safety.

When the reducing agent contains divalent iron ions, the container of storing the nitrogenous gas sustained releasing agent and reducing agent is preferably transparent. This is because upon reaction of the nitrite ion/nitrate ion-containing LDH with iron (II) ions, iron (II) ions change to brown iron (III) ions which ensure qualitative identification of the degree of reaction progress by the color of the mixture. The transparent container is exemplified by a glass or plastic container.

As described above, the nitrogenous gas sustained releaser according to the second aspect is designed to sustainably release off a nitrogenous gas selected from the group consisting of nitrogen monoxide gas, nitrous acid vapor, nitrogen dioxide gas, nitrous oxide gas, and ammonia.

Any form of nitrogenous gas sustained releaser may coexist with a dehydrator, a decarbonizing agent, a deoxidant, and so on for the purpose of enhancing its storage stability over an extended period of time.

(Third Aspect) A package according to yet another aspect of the invention in which the nitrogenous gas sustained releaser is used will now be explained as the third aspect.

Figure 5:
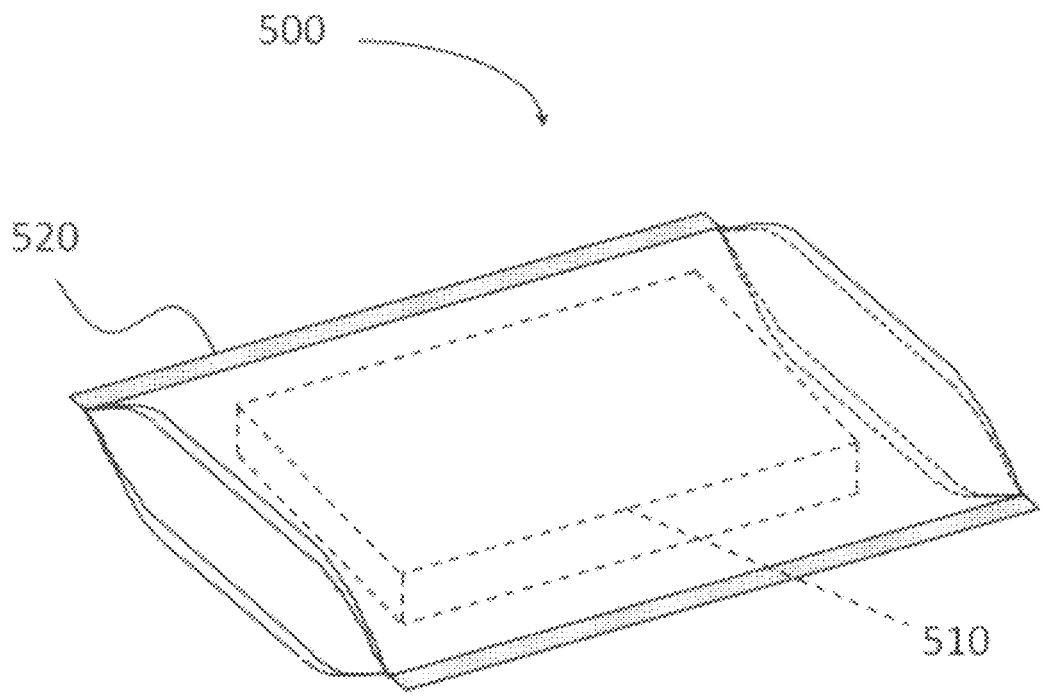
FIG. 5 is a schematic view illustrating a package according to the invention.

FIG. 5 is a schematic view showing a package according to the third aspect.

Referring to a package 500 according to the third aspect, a nitrogenous gas sustained releaser 510 is sealed up and contained in a wrapping material 520.

Here, a nitrogenous gas sustained releaser 510 corresponds to the nitrogenous gas sustained releaser represented by the 1st to 3rd embodiments of the second aspect, therefore, further explanation is omitted. Further, for the nitrogenous gas sustained releaser 510, the nitrogenous gas sustained releaser according to the 1st to 3rd embodiments can be used alone or can be modulated in combination with other member(s).

As mentioned above, when the nitrogenous gas sustained releaser 510 according to any of the $1^{st}$ to $3^{rd}$ embodiments is placed in the air, it will react with carbon dioxide and water to sustainably release off the nitrogenous gases. If it is provided in the form of such a package 500, it is then possible to avoid contact with carbon dioxide and water in the air until just prior to use.

There is no limitation on the quality of the wrapping material 520 provided that it does not react with the nitrogenous gas sustained releaser 510, has a gas barrier capability of preventing permeation of carbon dioxide, water and oxygen, and is not broken under normal storage conditions. Exemplarily, the wrapping material 520 could be an airtight bag in which the peripheral edge of an aluminum laminated film is fused and sealed up, a glass container having a tightly capped opening or the like. Although FIG. 5 shows an embodiment wherein the wrapping material 520 is in a sealed bag form, it is here noted that there is no limitation on the shape, structure, size, etc. of the wrapping material provided that a given amount of the nitrogenous gas sustained releasing agent can be contained, and that the nitrogenous gas sustained releasability can be maintained over a given period of time.

It is preferable to allow a voidless atmosphere, a vacuum, an inert gas atmosphere or a water-free dry atmosphere to fill in the interior of the package 500 in terms of an improvement in storage stability of the nitrogenous gas sustained releaser 510.

In the present disclosure, it is noted that the term "vacuum" stands for a state evacuated to a half the atmospheric pressure or lower, the term "inert gas atmosphere" stands for an atmosphere wherein the contents of oxygen gas and carbon dioxide gas are less than those of the air, and the term "dry atmosphere" stands for an atmosphere having a relative humidity of 50% or lower. For instance, the inert gas atmosphere includes a nitrogen gas atmosphere having a nitrogen gas content more than that of the air, and a rare gas atmosphere having a rare gas content more than that of the air.

An exemplary production method of the package 500 will now be explained.

In the package 500, the nitrogenous gas sustained releaser 510 may be sealed up and contained in the wrapping material 520. For instance, use may be made of a method of placing the nitrogenous gas sustained releaser 510 in the wrapping material 520 having an opening that is then sealed up. This operation may be carried out in the air if it can quickly be done. It is then preferable to seal up the opening after the wrapping material is deaerated to expel the air from inside, because the amount of air coming in contact with the nitrogenous gas sustained releaser 510 is so reduced that the storage stability of the nitrogenous gas sustained releaser 510 can be enhanced. If this operation is carried out in the inert gas atmosphere or dry atmosphere, it causes the inert gas atmosphere or dry atmosphere to fill in the wrapping material 520, or if the wrapping material 520 is evacuated inside prior to the sealing of said opening, it causes a vacuum to fill in the wrapping material 520. In any case, these methods are more preferable in terms of enhancements in the storability and stability of the nitrogenous gas sustained releaser 510. How to allow a vacuum, an inert gas atmosphere or a dry atmosphere to fill in the wrapping material 520 is not limited thereto; an expert in the art could have recourse to every imaginable method.

Prior to sealing, the nitrogenous gas sustained releaser 510 may be subjected to vacuum drying, ensuring removal of interlayer water, crystal water and/or adsorbed water contained in the contained nitrite ion/nitrate ion-containing LDH and the optionally contained reducing (or oxidizing) agent. This is more preferable because of enhancements in the storability and stability of the nitrogenous gas sustained releaser 510. Alternatively, the nitrogenous gas sustained releaser 510 may be subjected to vacuum drying with the application of heat in a range of temperatures at which there is no denaturation observed of the contained nitrite ion/nitrate ion-containing LDH and the optionally contained reducing (or oxidizing) agent.

It is here noted that it is acceptable to store the thus obtained package 500 in a refrigerator or freezer.

(Fourth Aspect)

A sustained releasing method of sustainably releasing off a nitrogenous gas according to yet another aspect in which the nitrogenous gas sustained releaser according to the second aspect is used will now be explained as the fourth aspect.

The nitrogenous gas sustained releaser composed of the nitrogenous gas sustained releasing agent containing at least the aforesaid nitrite ion/nitrate ion-containing LDH is used with the method of sustainably releasing off nitrogenous gases. As described above, typically, the nitrogenous gas sustained releaser may be used in three embodiments. Specifically, the following three releasers may be used: a sustained releaser making use of the nitrogenous gas sustained releasing agent alone ($1^{st}$ embodiment), a sustained releaser wherein the nitrogenous gas sustained releasing agent is spaced away from, and placed side by side with, the reducing (or oxidizing) agent ($2^{nd}$ embodiment), and a sustained releaser wherein the nitrogenous gas sustained releasing agent is directly mixed with the reducing (or oxidizing) agent ($3^{rd}$ embodiment). In what follows, the nitrogenous gas sustained releasing methods using three such releasers will be explained on an individual basis.

[The Nitrogenous Gas Sustained Releasing Method Using the Sustained Releaser ($1^{st}$ Embodiment) Making Use of the Nitrogenous Gas Sustained Releasing Agent Alone]

The nitrogenous gas sustained releasing method making use of the nitrogenous gas sustained releaser according to the first embodiment comprises a step of bringing a gas containing carbon dioxide and/or water vapor in contact with the nitrogenous gas sustained releaser according to the aforesaid first embodiment. The aforesaid "solid phase-gas phase anion exchange reaction" between carbon dioxide and/or water in the air and the nitrite ion-containing LDH underlies this sustained releasing method.

The nitrogenous gas sustained releaser according to the aforesaid first embodiment generates nitrous acid by way of the "solid phase-gas phase anion exchange reaction" between the main component nitrite ion-containing LDH and carbon dioxide and/or water in the air, which nitrous acid is then vaporized to sustainably release off nitrous acid vapor. Further, nitrous acid and nitrous acid vapor, because of being unstable compounds, are broken down into nitrogen monoxide and nitrogen dioxide by the self-oxidation-reduction reaction. As a result, the aforesaid nitrogenous gas sustained releaser according to the aforesaid first embodiment can be used to sustainably release off nitrogen monoxide and nitrogen dioxide.

In the step of bringing the gas containing carbon dioxide and/or water vapor in contact with the nitrogenous gas sustained releaser according to the aforesaid embodiment, any desired method may be used for the aforesaid contact provided that said nitrogenous gas sustained releaser comes in contact with carbon dioxide and/or water. Referring here to one example of contact, the nitrogenous gas sustained releaser according to the first embodiment may be placed in a container such as a glass vial bottle or a glass tube, followed by feeding of the gas containing carbon dioxide and/or water vapor into said container using a pump or the like. The feeding rate of the gas containing carbon dioxide and/or water vapor may be in a range of 10 (mL/min) to 20 (L/min) inclusive as an example.

While there is no particular limitation on the content of carbon dioxide in the gas, it may typically be in a range of 0.03% or 5% inclusive. The content of water (water vapor) in the gas may typically be in a range of 40% to 100% inclusive, as expressed in terms of relative humidity.

In the step of bringing the gas containing carbon dioxide and/or water vapor in contact with the nitrogenous gas sustained releaser according to the aforesaid embodiment, said gas may be prepared by adding water vapor and carbon dioxide to air or an inert gas such as nitrogen or a rare gas. The addition of water vapor may be carried out by every possible method ordinarily occurring to an expert in the art such as a bubbling method comprising aeration through water, a method of aeration through a column loaded up with water-wetted paper or cloth, a method making use of water generated by chemical reaction, a method comprising concentration of moisture in air, and a method making use of exhaled air. The addition of carbon dioxide may be carried out by every possible method ordinarily occurring to an expert in the art such as a method using a high-pressure bomb, a method using carbonated water, a method using dry ice, a method using a solid material such as a bath additive that comes in contact with water to generate carbon dioxide, a method using a solid material that comes in contact with oxygen to generate carbon dioxide, a method using combustion reaction, a method of heating a material to which carbon dioxide is adsorbed to separate off carbon dioxide, a method using chemical reaction, a method of concentrating carbon dioxide in air, and a method using exhaled air.

In the step of bringing the gas containing carbon dioxide and/or water vapor in contact with the nitrogenous gas sustained releaser according to the aforesaid first embodiment, said nitrogenous gas sustained releaser may be heated thereby boosting up the self-oxidation-reduction reaction of nitrous acid vapor, the diffusion of molecules or ions in the nitrite ion-containing LDH, the vaporization of nitrous acid, etc. so that the sustained releasing concentration of nitrogenous gases can be enhanced. For instance, heating may be carried out in a temperature range of 30° C. to 150° C. inclusive.

When the nitrogenous gas sustained releaser according to the aforesaid first embodiment is used to create a package 500 according to the aforesaid third aspect, it is possible to sustainably release of nitrogenous gases by opening said package 500 to bring carbon dioxide and/or water vapor in contact with the aforesaid nitrogenous gas sustained releaser 510.

As described above, in the step of bringing the gas containing carbon dioxide and/or water vapor in contact with the nitrogenous gas sustained releaser according to the aforesaid first embodiment, it is possible to sustainably release nitrous acid vapor, nitrogen monoxide and nitrogen dioxide out of said nitrogenous gas sustained releaser. How to take only nitrogen monoxide out of these gases will now be explained.

In one example of this method, a basic adsorbent is disposed in the rear stage of the nitrogenous gas sustained releaser according to the aforesaid first embodiment, and the gas sustainably released out of said releaser is then brought in contact with said adsorbent. Among the aforesaid gases, nitrous acid vapor and nitrogen dioxide are an acidic gas whereas nitrogen monoxide is a neutral gas. Upon coming in contact with said adsorbent, nitrous acid vapor and nitrogen dioxide are adsorbed to said adsorbent so that only nitrogen monoxide is sustainably released off. More specifically, magnesium hydroxide loaded up in a glass tube is provided as the basic adsorbent, and the gas sustainably released out of the nitrogenous gas sustained releaser according to the aforesaid first embodiment is brought in contact with magnesium hydroxide.

In addition to the aforesaid magnesium hydroxide, the basic adsorbent used herein includes calcium hydroxide, sodium hydroxide, hydrated lime, quicklime, soda lime, a basic polymer such as polyvinylpyridine, an organic compound having an amino group, a silica gel modified with an amino group, etc. From a safety standpoint, it is preferable to use an adsorbent that has low hygro-scopicity, is free from deliquescence, and is not dissolved in water to form an irritating, strong basic liquid. The basic adsorbent is preferably magnesium hydroxide that is a less water soluble solid base. It is here noted that through comparisons of properties of nitrogenous gases to be removed out of coexisting gas species with properties of nitrogenous gases desired to have increased purities, an expert in the art could select a desired one from every possible adsorbent.

In another example of sustainably releasing off nitrogen monoxide alone, a gas sustainably released out of the nitrogenous gas sustained releaser according to the aforesaid first embodiment is bubbled in water. Because nitrogen monoxide is a gas insoluble in water whereas nitrous acid vapor and nitrogen dioxide are soluble in water, nitrous acid vapor and nitrogen dioxide are dissolved by bubbling in water, rendering selective removal of both nitrous acid and nitrogen dioxide possible. The water used for bubbling is preferably alkaline in view of removal efficiency. It is here noted that the method of sustainably releasing nitrogen monoxide alone out of a gas containing nitrous acid vapor, nitrogen monoxide and nitrogen dioxide, that is, the method of removing only nitrous acid vapor and nitrogen dioxide is not limited to these; an expert in the art could have recourse to every possible method.

In what follows, how to take nitrogen dioxide out of nitrous acid vapor, nitrogen monoxide and nitrogen dioxide sustainably released out of the nitrogenous gas sustained releaser according to the aforesaid first embodiment will now be explained.

In one example of this method, the gas sustainably released out of the nitrogenous gas sustained releaser according to the aforesaid first embodiment is brought in contact with the air. By way of the self-oxidation-reduction reaction represented by formula (5), nitrous acid yields nitrogen monoxide and nitrogen dioxide, and by way of the reaction represented by formula (6), nitrogen monoxide reacts with oxygen in the air to yield nitrogen dioxide; so the gas sustainably released out of the nitrogenous gas sustained releasing agent according to the aforesaid first embodiment is brought in contact with the air for a certain period of time, causing the reactions represented by formulae (5) and (6) to make progress for conversion of nitrous acid vapor and nitrogen monoxide contained in said gas into nitrogen dioxide. Upon contact of the aforesaid sustainably released gas with the air, the nitrogenous gas sustained releaser of the aforesaid first embodiment and/or the sustainably released nitrogenous gases may be heated. This is preferable because the reactions of formulae (5) and (6) are accelerated. For instance, heating may be carried out within a temperature range of 30° C. to 150° C. inclusive.

Thus, the desired gas alone may be taken out of the nitrogenous gas sustained releaser according to the first embodiment.

[Method of Sustainably Releasing Off Nitrogenous Gases with the Use of a Sustained Releaser ($2^{nd}$ Embodiment) Wherein the Nitrogenous Gas Sustained Releasing Agent is Spaced Away from, and Placed Side by Side with, the Reducing (or Oxidizing) Agent]

A method of sustainably releasing off nitrogenous gases with the use of a nitrogenous gas sustained releaser according to the second embodiment comprises a step of bringing a gas containing carbon dioxide and/or water vapor in contact with a nitrogenous gas sustained releasing agent that forms a part of the aforesaid sustained releaser, and a step of bringing nitrous acid vapor obtained in said step in contact with a solid reducing (or oxidizing) agent that forms a part of the aforesaid sustained releaser. The aforesaid "solid phase-gas phase anion exchange reaction" between carbon dioxide and/or water in the air and the nitrite ion-containing LDH underlies this sustained releasing method.

The step of bringing the gas containing carbon dioxide and/or water vapor in contact with the nitrogenous gas sustained releaser will not be explained any longer because of being the same as the step of bringing said gas in contact with the nitrogenous gas sustained releaser according to the aforesaid $1^{st}$ embodiment.

For instance, the step of bringing nitrous acid vapor in contact with the solid reducing (or oxidizing) agent may be carried out by passing nitrous acid vapor sustainably released out of the nitrogenous gas sustained releasing agent through the solid reducing (or oxidizing) agent that forms a part of the nitrogenous gas sustained releaser according to the $2^{nd}$ embodiment thereby converting nitrous acid into other nitrogenous gases. The nitrous acid vapor, because of having high reactivity, is converted by the action of the reducing (or oxidizing) agent into nitrogen monoxide (NO), nitrous oxide ($N_2O$), nitrogen dioxide ($NO_2$), ammonia ($NH_3$) or nitrogen ($N_2$). The solid reducing (or oxidizing) agent may be spaced away from, and placed side by side with, the nitrogenous gas sustained releasing agent or loaded up in a column such that it is not directly mixed with the nitrogenous gas sustained releasing agent.

For instance, the solid reducing agent or solid oxidizing agent used here includes iron (II) sulfate, tin (II) chloride, hexavalent chromium, zinc or sulfamic acid, and upon reactions of these with nitrous acid vapor, it is converted into nitrogen oxide (NO), nitrous oxide ($N_2O$), nitrogen dioxide ($NO_2$), ammonia ($NH_3$) or nitrogen ($N_2$), respectively. In other words, as nitrous acid vapor passes through a column loaded up with a divalent iron ion-containing solid such as iron (II) sulfate, it turns into nitrogen monoxide, and as it goes through a column loaded up with tin (II) chloride, it turns into nitrous oxide. As nitrous acid vapor passes through a column loaded up with hexavalent chromium, zinc powders, and sulfamic acid, it turns into nitrogen dioxide, ammonia, and nitrogen ($N_2$), respectively. After passing nitrous acid vapor through a column loaded up with iron (II) sulfate for conversion into nitrogen monoxide, this nitrogen monoxide may be converted into nitrogen dioxide using a column loaded up with hexavalent chromium. Thus, combined use of a plurality of reducing or oxidizing agents results in cascade reactions by which the desired nitrogenous gas alone may be sustainably released off. Although, in the examples given later, iron (II) sulfate heptahydrate is used as the reducing agent for sustained releasing of nitrogen monoxide, it goes without saying that the aforesaid reducing agents may optionally be used.

The step of bringing the gas containing carbon dioxide and/or water vapor in contact with the nitrogenous gas sustained releasing agent, and the step of bringing nitrous acid vapor sustainably released out of the nitrogenous gas sustained releasing agent in contact with the solid reducing (or oxidizing) agent may repeatedly be carried out whereby the nitrogenous gas is accumulated or piled up so that it can be released off in high concentrations. An expert in the art could have recourse to every ordinarily possible method such as a method of connecting the nitrogenous gas sustained releasing agent and reducing agent in an alternate arrangement using a tube or the like, and a method of alternately filling the nitrogenous gas sustained releasing agent and reducing agent in a column.

In the nitrogenous gas sustained releasing method using the nitrogenous gas sustained releaser according to the aforesaid second embodiment, too, the step of placing an adsorbent in the rear stage of said sustained gas releaser for adsorption of the given gas may be carried out. The adsorption step used here will not be explained any longer because of being the same as mentioned above. This step enables to enhance the purity of the desired nitrogenous gas.

In the nitrogenous gas sustained releaser according to the second embodiment, the nitrite ion-containing LDH is spaced away from the solid reducing (or oxidizing) agent so that two such agents are in no contact, as described above. This sustained releaser has a characteristic feature of sustainably releasing off nitrogenous gases by way of a process wherein nitrous acid vapor sustainably released out of the nitrite ion-containing LDH arrives at the reducing (or oxidizing) agent where it is converted into nitrogenous gases other than nitrous acid. There are various redox reactions known for nitrous acid; therefore, generation and sustainable release of various nitrogenous gases become possible by an appropriate combination of the nitrite ion-containing LDH with an appropriate oxidizing or reducing agent.

It is here noted that in addition to using the solid oxidizing or reducing agent that is a chemical substance, it is acceptable to use electrochemical methods or electrochemical catalysts to oxidize/reduce nitrous acid or nitrous acid vapor.

[Nitrogenous Gas Sustained Releasing Method Using a Sustained Releaser ($3^{rd}$ Embodiment) Wherein the Nitrogenous Gas Sustained Releasing Agent is Directly Mixed with the Solid Reducing (or Oxidizing) Agent]

The nitrogenous gas sustained releasing method using the nitrogenous gas sustained releaser according to the third embodiment comprises a step of bringing a gas containing at least water vapor in contact with the aforesaid sustained releaser. This sustained releasing method is based on the aforesaid "solid phase-solid phase anion exchange reaction" between the solid reducing (or oxidizing) agent and the nitrite ion/nitrate ion-containing LDH mediated by the water in the atmosphere. The solid phase-solid phase anion exchange reaction, because of taking place in association with diffusion of interlayer ions and gas molecules, makes it possible to sustainably release off nitrogenous gases over an extended period of time.

In the step of bringing the gas containing at least water vapor in contact with the nitrogenous gas sustained releaser according to the aforesaid third embodiment, the contact may be carried out by any desired method with the proviso that the aforesaid sustained releaser is in contact with the water vapor-containing gas. In one example of this contact, the nitrogenous gas sustained releaser according to the third embodiment may be placed in a column such as a glass vial or tube, to which column the water vapor-containing gas is fed by means of a pump or the like. For instance, the feed speed of the water vapor-containing gas may be within a range of 10 (mL/min) to 20 (L/min) inclusive. The content of water in the gas may be in a range of 40% to 100% inclusive, as expressed in terms of relative humidity. It is noted that the water vapor-containing gas may be prepared as mentioned above, and carbon dioxide may be added to a gas flow or the nitrogenous gas sustained releaser may be heated for the purpose of regulating the sustained releasing concentration. Heating may be carried out in a temperature range of 30° C. to 150° C. inclusive as an example.

When the nitrogenous gas sustained releaser according to the aforesaid $3^{rd}$ embodiment wherein the nitrogenous gas sustained releasing agent is mainly composed of the nitrite ion-containing LDH and the solid reducing agent is iron (II) sulfate is loaded up in a column and a water vapor-containing gas is passed through said column, nitrite ions released out of the LDH layer react with the divalent iron ions of the reducing agent for conversion into nitrogen monoxide. If water vapor is here added to air, it is then possible to accelerate the solid phase-solid phase anion exchange reaction so that nitrogen monoxide can be sustainably released off in higher concentrations.

Alternatively, when the nitrogenous gas sustained releaser according to the aforesaid $3^{rd}$ embodiment wherein the nitrogenous gas sustained releasing agent is mainly composed of the nitrite ion-containing LDH and the solid reducing agent is tin (II) chloride is loaded up in a column and the water vapor-containing gas is passed through said column, nitrous oxide is sustainably released off.

Yet alternatively, when the nitrogenous gas sustained releaser according to the aforesaid $3^{rd}$ embodiment wherein the nitrogenous gas sustained releasing agent is mainly composed of the nitrate ion-containing LDH and the solid reducing agent is zinc and iron (II) sulfate is loaded up in a column and the water vapor-containing gas is passed through said column, nitrogen monoxide, nitrogen dioxide and nitrous acid are sustainably released off.

In the nitrogenous gas sustained releasing method using the nitrogenous gas sustained releaser according to the aforesaid third embodiment, too, the step of placing an adsorbent in the rear stage of said sustained releasing agent for adsorption of the given gas may be carried out. The adsorption step, because of being the same as mentioned above, will not be explained any longer. By this step it is possible to enhance the purity of the desired nitrogenous gas.

When the nitrogenous gas sustained releaser according to the third embodiment is obtained just prior to contact with the gas containing at least water vapor, that is, when the nitrogenous gas sustained releasing agent is mixed with the solid reducing agent just prior to said contact, an expert in the art could have recourse to every imaginable mixing method such as a method of removing a movable partition located between the nitrogenous gas sustained releasing agent and the solid reducing (or oxidizing) agent, a mechanical stirring method or a pulverization mixing method using a device such as a pepper mill.

When the nitrogenous gas sustained releaser according to the aforesaid third embodiment is used to make the package 500 according to the aforesaid third aspect, it is possible to sustainably release off nitrogenous gases by opening said package 500 to take out the aforesaid nitrogenous gas sustained releaser 510 for contact with the water vapor-containing gas. Alternatively, the nitrogenous gas sustained releasing agent and the solid reducing (or oxidizing) agent may be sealed up and contained in separate packages. Just prior to contact with the water vapor-containing gas, each package may be opened to mix both together, after which the gas sustained releasing agent is brought in contact with the water vapor-containing gas.

Referring further to the nitrogenous gas sustained releasing method according to the fourth aspect as described above, temporary stopping of nitrogenous gas sustained release on the way is possible by placing the nitrogenous gas sustained releaser in an inert gas atmosphere or a vacuum before finishing the release.

(Fifth Aspect)

The nitrogenous gas sustained releasing apparatus according to a further aspect using the nitrogenous gas sustained releaser according to the second aspect will now be explained as the fifth aspect.

Figure 6:
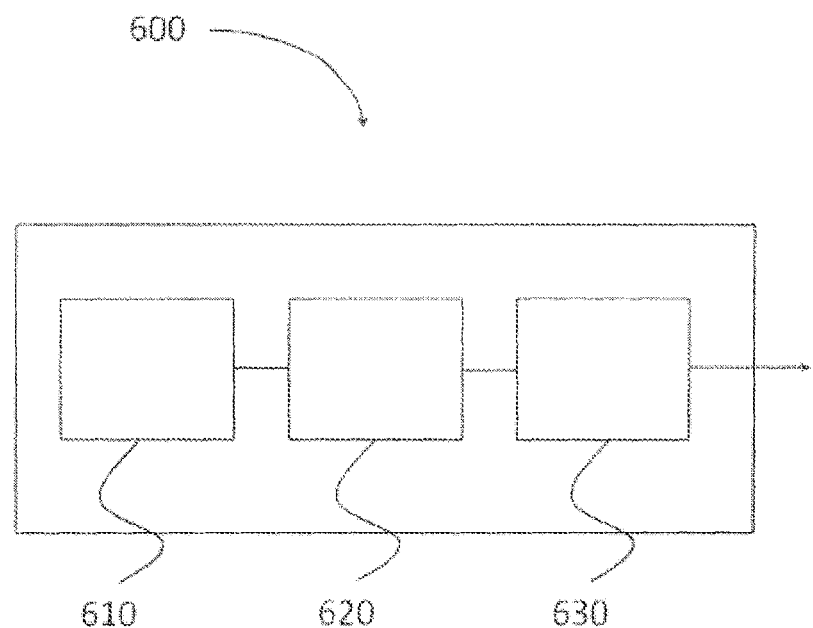
FIG. 6 is a schematic view illustrating a nitrogenous gas sustained releasing apparatus.

FIG. 6 is a schematic view showing a nitrogenous gas sustained releasing apparatus.

A sustained releasing apparatus 600 according to the fifth aspect comprises at least an atmospheric gas feeding portion 610 adapted to feed an atmospheric gas, and a nitrogenous gas sustained releasing portion 620 adapted to sustainably release off a nitrogenous gas via an atmosphere gas fed out of the atmospheric gas feeding portion 610. The sustained releasing apparatus 600 of the invention further comprises an impurity gas removal portion 630 adapted to remove impurities from the nitrogenous gas released out of the nitrogenous gas sustained releasing portion 620, but this portion is not essential.

Any desired means capable of feeding a gas containing at least water vapor may be used for the atmospheric gas feeding portion 610. Examples include a pump, a bomb, an exhaled air inlet or the like. When the pump is used, it may be combined with a humidifier as an example. In addition to the water vapor-containing gas, the atmospheric gas feeding portion 610 may feed carbon dioxide. The atmospheric gas feeding portion 610 may comprise a plurality of bombs, each containing gases capable of being fed to the nitrogenous gas sustained releasing portion 620 in combination.

The nitrogenous gas sustained releasing portion 620 comprises at least the nitrogenous gas sustained releaser according to the second aspect which, because of being the same as mentioned above, will not be explained any longer. The nitrogenous gas sustained releaser may be loaded up and placed in a column. The nitrogenous gas sustained releasing portion 620 is connected to a gas feed pipe or the like in such a way that the atmospheric gas fed out of the atmospheric gas feeding portion 610 comes in contact with the nitrogenous gas sustained releaser. It is here noted that the package according to the third aspect may be opened just prior to the start of feeding of the atmospheric gas to locate the nitrogenous gas sustained releaser according to the second aspect in place.

Referring further to the nitrogenous gas sustained releasing portion 620 wherein the nitrogenous gas sustained releaser according to the aforesaid second embodiment is used as the nitrogenous gas sustained releaser, a plurality of nitrogenous gas sustained releasers, each comprising a set of a nitrogenous gas sustained releasing agent and a solid reducing (or oxidizing) agent, may be provided. In this case, it is preferable that the solid reducing or oxidizing agent is placed in the rear stage of the nitrogenous gas sustained releasing agent. As plural nitrogenous gas sustained releasers are provided, it allows nitrogenous gases to be released off in high concentrations.

The nitrogenous gas sustained releasing portion 620 may further comprise heating means such as a heater that increases diffusion of molecules and ions in the nitrite ion/nitrate ion-containing LDH in the nitrogenous gas sustained releasing agent so that the anion exchange reaction can be boosted up with an increase in the sustained releasing concentration of nitrogenous gases.

The impurity gas removal portion 630 provides means adapted to adsorb and remove unnecessary components (impurities) contained in the sustainably released gases. One example of removal by adsorption is an adsorbent loaded up in a column. When the adsorbent is a basic adsorbent, nitrous acid vapor and nitrogen dioxide can be removed by adsorption. Such a basic adsorbent, because of being the same as described above, will not be explained any longer. Another example of removal by adsorption is a water bubbling device adapted to remove nitrous acid vapor and nitrogen dioxide by adsorption. If nitrogen monoxide is oxidized into nitrogen dioxide, it can be removed by the basic adsorbent thereby purifying chemically stable nitrous oxide. As nitrogen monoxide is known to be coordinated at the center metal of a ruthenium complex or the like to form a nitrosyl complex, it can be removed by adsorption on the basis of the formation of the nitrosyl complex.

In the nitrogenous gas sustained releasing apparatus 600 according to the fifth aspect, if necessary, means adapted to feed an atmospheric gas from the atmospheric gas feeding portion 610 may be provided in the rear stage of the impurity gas removal portion 630 or, alternatively, another separate atmospheric gas feeding portion may be provided. It is thus possible to regulate the sustained releasing concentration of nitrogenous gases obtained in the impurity gas removal portion 630. The sustained releasing apparatus 600 according to the fifth aspect can be downsized to convenient-to-carry bag size.

The operation of the sustained releasing apparatus 600 according to the fifth aspect will now be explained on the assumption that, for simplification, the nitrogenous gas sustained releaser according to the aforesaid third embodiment comprising the reducing agent containing divalent iron ions is provided in the nitrogenous gas sustained releasing portion 620 as the nitrogenous gas sustained releaser and the sustained releasing apparatus 600 is provided for sustained releasing of nitrogen monoxide gas.

The gas containing at least water vapor is fed from the atmospheric gas feeding portion 610 to the nitrogenous gas sustained releasing portion 620 where the "solid phase-solid phase anion exchange reaction" takes place between the reducing agent and the nitrite ion/nitrate ion-containing LDH mediated by the fed water, resulting in release of nitrite ions from the nitrite ion/nitrate ion-containing LDH. Then, nitrite ions react with divalent iron ions for conversion into nitrogen monoxide that is then sustainably released off.

As the nitrogenous gas sustained releasing apparatus shown in FIG. 6 further comprises the impurity gas removal portion 630, nitrogen monoxide generated in the nitrogenous gas sustained releasing portion 620 as well as nitrous acid vapor, nitrogen dioxide, etc. remaining unconverted are fed to the impurity gas removal portion 630 where nitrous acid vapor and nitrogen dioxide are removed by adsorption so that purified nitrogen monoxide gas can be sustainably released out of the sustained releasing apparatus 600.

If the nitrogenous gas sustained releaser according to the second aspect is introduced into the medical field, it is then possible to provide medical respiratory equipment. For instance, only nitrogen monoxide can be sustainably released off by the nitrogenous gas sustained releasing apparatus comprising a hand-operated pump acting as the atmospheric gas feeding portion 610, and the nitrogenous gas sustained releaser according to the second aspect acting as the nitrogenous gas sustained releasing portion 620 with options such as a humidifier and an adsorbent. The sustainably released nitrogen monoxide is fed to a patient by way of a ventilator.

According to the nitrogenous gas sustained releasing apparatus assembled as described above, it is possible to feed nitrogen monoxide having the concentration required in medical levels by manual operation alone without recourse to a power source such as a battery whatsoever. This sustained releasing apparatus is advantageous for use in situations or environment such as emergency lifesaving of patients having difficulty breathing as well as use in developing countries, at home and at power failure, which are unmanageable even for the existing state of art.

In what follows, the present invention will be explained specifically with reference to examples. It is noted, however, that these examples are given as an aid to have a better understanding of the present invention; they are by no means given for limitation on the present invention.

EXAMPLES

[How to Measure the Components of Nitrogenous Gases]

Prior to Examples, how to measure the components of sustainably released nitrogenous gases is explained.
(1) Quantitative Measurement of Nitrogen Dioxide, Nitrogen Monoxide and Nitrous Acid Vapor Using Griess Reagent and a Detector Tube.

A nitrous acid vapor-containing gas generated out of the nitrogenous gas sustained releasing agent or sustained releaser was aerated through an aqueous solution containing Griess reagent that was a nitrite ion coloring reagent with application of bubbling to identify release of nitrous acid vapor by the color change of said aqueous solution from colorless to purple. The quantitative determination of nitrous acid can be carried out by measuring the visible ultraviolet adsorption spectra of the aqueous solution of Griess reagent undergoing coloration in response to nitrous acid.

By aerating the gas generated out of the nitrogenous gas sustained releasing agent or sustained releaser through a detector tube (No. 11L made by Gastec Corporation) for detection of nitrogen monoxide+nitrogen dioxide, the combined quantity of nitrogen monoxide+nitrogen dioxide+ nitrous acid was determined. As said detector tube is installed on its tip with a strong oxidizing agent ($Cr^{6+}$+ $H_2SO_4$) for the purpose of oxidizing nitrogen monoxide into nitrogen dioxide, nitrous acid in the aerated gas is also oxidized and converted into nitrogen dioxide. For this reason, the total of nitrogen monoxide, nitrogen dioxide and nitrous acid is obtained as a quantity of nitrogen dioxide. This reaction may also be used as the method of generating nitrogen dioxide from nitrous acid vapor.

By aerating the gas generated out of the nitrogenous gas sustained releasing agent or sustained releaser through a detector tube for detection of nitrogen dioxide (No. 10 or No. 9P made by Gastec Corporation), the quantity of nitrogen dioxide alone was determined. Said detector tube does not respond to nitrogen monoxide and nitrous acid because it is not provided on its tip with any strong oxidizing agent ($Cr^{6+}$+$H_2SO_4$). For this reason, the quantity of only nitrogen dioxide in the gas is determined. As this detector tube for detection of nitrogen dioxide (No. 10 made by Gastec Corporation) uses orthotolidine that is an organic amine as a coloring reagent, nitrous acid that is an acidic gas is neutralized and adsorbed onto the detector tube, but the coloring reagent does not show any coloration.

Further, the gas generated out of the nitrogenous gas sustained releasing agent or sustained releaser was passed through the detector tube for detection of nitrogen dioxide (No. 10 made by Gastec Corporation) to remove nitrogen dioxide and nitrous acid, after which the detector tube for detection of nitrogen monoxide+nitrogen dioxide (No. 11L made by Gastec Corporation) was used to determine the quantity of nitrogen monoxide alone. This process may also be considered as a method of purifying nitrogen monoxide using the detector tube for detection of nitrogen dioxide (No. 10 made by Gastec Corporation). It is here noted that not only nitrogen dioxide but also nitrous acid is removed out of the gas passed through the detector tube for detection of nitrogen dioxide (No. 10 made by Gastec Corporation), as identified by a coloring method using the aforesaid Griess reagent.

Based on the foregoing measurement results, the concentration of nitrogen dioxide and nitrogen monoxide was subtracted from the concentration of nitrogen monoxide+ nitrogen dioxide+nitrous acid to figure out the concentration of nitrous acid.
(2) Quantitative Method of Measuring Nitrous Oxide Using Infrared Spectroscopy Nitrous oxide sustainably released out of the nitrogenous gas sustained releasing agent was measured by infrared spectroscopy using a gas cell. The gas generated out of the nitrogenous gas sustained releasing agent was aerated through a gas cell for infrared absorption spectra (made by GL Science Inc. with an optical path length of 10 cm and a single crystal NaCl window frame) at a flow rate of 100 mL/min to measure Fourier transform infrared absorption spectra at a time interval of 2 minutes for gas component analysis. When the aerated gas contained 50% or more water vapor, said gas was dehumidified through a column loaded up with a molecular sieve 3A $1/16$ for the purpose of protecting the NaCl single crystal that was a window material, after which it was aerated through the gas cell. The molecular sieve 3A $1/16$ used was dried under the air at 200° C. for one day or longer using an electrical oven for activation, and then cooled from 200° C. down to room temperature in vacuo. The Fourier transform infrared adsorption spectra were measured using NEXUS 670-FT-IR made by NICOLET within a measurement range of 4000 to 600 $cm^{-1}$ with an accumulation number preset to 16. The gas cell was set in a sample chamber within a spectrometer with a dry nitrogen gas atmosphere filling in the sample chamber.
(3) Quantitative Method of Measuring Ammonia Using a Detector Tube Ammonia sustainably released out of the nitrogenous gas sustained releasing agent was measured using a detector tube (Gastec 3L).

[Method of Releasing Off Nitrogenous Gas Components]

Release experimentation for various nitrogenous gases was carried out as outlined below.

First of all, the nitrogenous gas sustained releasing apparatus 600 shown in FIG. 6 was assembled. A pump was used as the atmospheric gas feeding portion 610, and a container provided therein with the nitrite ion/nitrate ion-containing LDH was used as the nitrogenous gas sustained releasing portion 620. A column load up with magnesium hydroxide was used as the impurity gas removal portion 630, when provided.

Nitrite ion-containing LDH or Nitrate ion-containing LDH was used as nitrite ion/nitrate ion-containing LDH which was the nitrogenous gas sustained releasing agent and then applied as the nitrogenous gas sustained releaser. If required, the nitrite ion/nitrate ion-containing LDH was spaced away from, and placed side by side with, the reducing agent (iron (II) sulfate heptahydrate, zinc or the like), or it was directly mixed with the reducing agent into the nitrogenous gas sustained releaser. When the reducing agent was placed side by side with the nitrogenous gas sustained releasing agent, a column loaded up with the reducing agent was used.

The pump and the container having the nitrite ion/nitrate ion-containing LDH placed therein were connected by a gas feeder pipe, and an air of 20° C. was introduced from the pump at a constant flow rate of 50 mL/min or 100 mL/min. It is here noted that the air fed in the container was reduced or increased in terms of temperature, humidity, and amount of carbon dioxide. The humidity, and carbon dioxide concentration was regulated by feeding exhaled air (100% relative humidity and 4.0% carbon dioxide) stored in a humidifier or Tedlar® bag using the pump.

The side of the container (having the nitrite ion/nitrate ion-containing LDH placed therein) in opposition to the gas feeder pipe was connected with a discharge pipe, and a gas exiting the vent pipe was introduced through a filter into Griess reagent or a detector tube to detect nitrogenous gases.

Further, a gas exiting the discharge pipe was passed through a column loaded up with iron (II) sulfate and, if required, through a column loaded up with magnesium hydroxide to detect nitrogenous gases using the detector tube or measure the concentration of nitrogen monoxide using a nitrogen monoxide concentration sensor (ToxiRAE Pro made by RAE Systems with a detection range of 0.5 to 250 ppm). The time-dependent concentration change of nitrogen monoxide was measured per minute, and depending on sustained releasing time, measurement intervals were regulated between per 1 and per 5 minutes.

It is here noted that the concentrations of nitrogenous gases can also be measured using other concentration measurement equipment such as gas chromatography equipment, an infrared spectrometer or an ozone luminescence device in place of the detector tube or nitrogen monoxide concentration sensor.

Example 1

A commercially available carbonate type layered double hydroxide (DHT-6 made by Kyowa Chemical Industry Co., Ltd. with a particle diameter distribution of about 0.1 to 1 m and a Mg/Al molar ratio of 2.99 (±0.06)) having Mg ions as divalent metal ions and Al ions as trivalent metal ions and represented by a general formula: $Mg_3Al(OH)_8(CO_3^{2-})_{0.5} \cdot 2H_2O$ was used as the carbonate type LDH. Hereafter, this LDH will be described as $CO_3^{2-}$ MgAl-LDH3.

First of all, the carbonate type LDH was converted into Cl type LDH according to the method set forth in Japanese Patent No. 5867831. Specifically, 2.0 grams of $CO_3^{2-}$ MgAl-LDH3 were weighed, and placed in a three-neck flask to which 300 mL of ethanol were added. Then, 16.1 mL of an alcohol solution of hydrochloric acid (3 mass %) were added dropwise to the resulting suspension at 35° C. for 2 hours while the suspension was stirred by a magnetic stirrer under a nitrogen flow (500 mL/min) for reaction. Thereafter, the ensuing solution was filtrated by a membrane filter having a pore diameter of 0.2 m in a nitrogen flow, and the filtrate (residues) was fully washed with methanol. The residues were gathered up and collected, just after which they were evacuated and dried in vacuo for 1 hour or longer to obtain white powders.

The infrared adsorption spectra of the obtained white powders were measured by a Fourier transform infrared spectrophotometer (Perkin-Elmer Spectrum One, ATR attachment). As a result, there was no absorption of 1360 cm−1 attributable to carbonate ions found, judging that carbonate ions were substituted by chloride ions. Hereafter, this LDH will be referred to as Cl−MgAl-LDH3.

Then, nitrite ion-containing LDH was prepared from Cl−MgAl-LDH3. In a glove box in which a nitrogen atmosphere filled, 182.7 mg of $NaNO_2$ (Wako Pure Chemical Corporation) were dissolved in 30 ml of degassed ion exchange water to prepare a $NaNO_2$ solution. It is here noted that the degassed ion exchange water used herein was obtained by boiling ion exchange water, and then cooling it while nitrogen gas bubbling was carried out. In the examples given later, too, the ion exchange water subjected to the same operation was used.

Forty (40) mg of Cl−MgAl-LDH3 were weighed and placed in a 30 mL glass vial, and in the aforesaid glove box, the aforesaid $NaNO_2$ solution was added to the glass vial, followed by full shaking for dispersion. The glass vial was tightly capped for a two-day reaction, after which the reaction solution was filtrated through a membrane filter having a pore diameter of 0.2 μm in the glove box. The residues were washed with degassed ion exchange water, evacuated together with the membrane filter, and dried in vacuo for about 120 minutes to obtain a white powdery sample.

The FTIR measurement of the white powdery sample was carried out. As a result, absorption of 1227 cm$^{-1}$ by nitrite ions ($NO_2^-$) was observed, and its infrared absorption band showed sufficient absorption intensity as strong as that of other infrared absorption band derived from interlayer water, LDH skeleton or the like. From this, it was judged that chloride ions were sufficiently substituted by nitrite ions so that the nitrite ion-containing LDH was obtained. As a result of measurement of Mg/Al ratios by SEM-EDS (JSM6010LA made by JEOL Ltd., 10 kV), it was found that the Mg/Al ratio of the starting carbonate type LDH was maintained. The value of Cl relative to Al was about 8 to 9% that were considered to be equivalent to the quantity of chloride ions remained unsubstituted by nitrite ions upon preparation of the nitrite ion-containing LDH from Cl−MgAl-LDH3. As can be seen from a comparison of (i) with (iii) in FIG. 15c, an X-ray diffraction pattern reflected the characteristic feature of the layered double hydroxide; it would be considered that the nitrite ion-containing LDH obtained by progress of anion exchange without destroying the structure of the starting carbonate type LDH ($Mg_3Al(OH)_8(CO_3^{2-})_{0.5} \cdot 2H_2O$) meets the aforesaid general formula (1).

Then, a package in which the nitrite ion-containing LDH was sealed up and contained was produced. One hundred (100) mg of a powdery sample of the obtained white nitrite ion-containing LDH were placed and tightly capped in a 13.5 mL glass container (wrapping material) together with a membrane filter in the aforesaid glove box to obtain the package.

Figure 7:
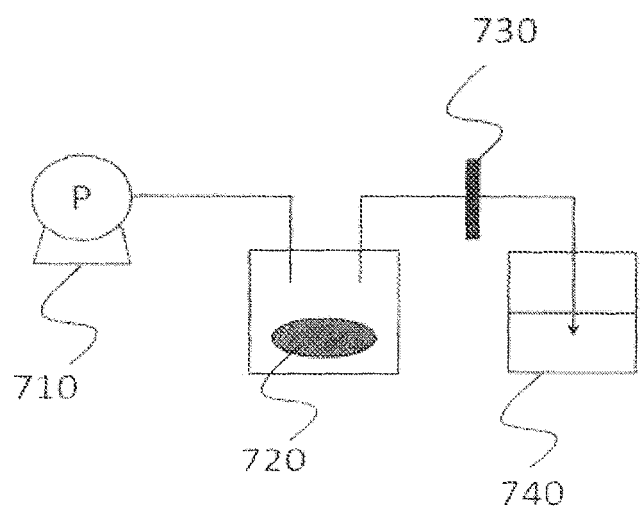
FIG. 7 is a schematic view illustrating an apparatus and experimental system used in Example 1.

Then, the package was opened up, and nitrous acid vapor was released out of the nitrite ion-containing LDH using the apparatus shown in FIG. 7, and detected by Griess reagent.

FIG. 7 is a schematic view showing the apparatus and experimental system used in Example 1.

Specifically, the air (20° C., a relative humidity of 35% and a carbon dioxide concentration of approximately 500 ppm) was fed to a nitrite ion-containing LDH powdery sample 720 in a glass container (also called a glass vial bottle) at a flow rate of 100 mL/min using a pump 710 and passed through a filter 730 having a pore diameter of 0.45 m, and then aerated through a 3 mL aqueous solution 740 having Griess reagent (1 g/25 mL) dissolved therein, followed by a 15-minute bubbling. Changes in Griess reagent were observed, and absorption spectra were measured before and after aeration through Griess reagent, using a spectrophotometer (Model No. UV-3600 made by Shimadzu Corporation). The results are shown in FIG. 8.

Figure 8:
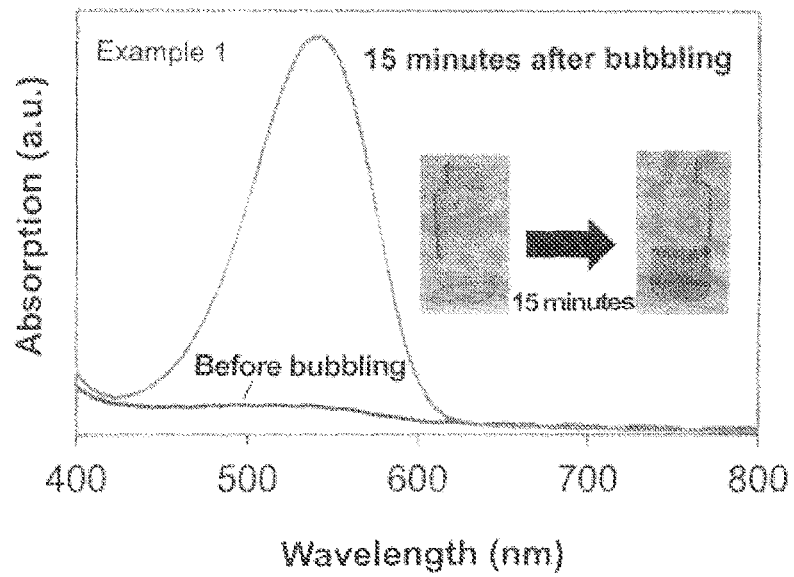
FIG. 8 is indicative of changes in Griess reagent and changes in absorption spectra before and after aeration in Example 1.

FIG. 8 shows changes in Griess reagent and changes in the absorption spectra before and after aeration in Example 1.

As shown in FIG. 8, the Griess reagent aqueous solution before aeration was nearly colorless and transparent, but it turned into pink after aeration. In FIG. 8 provided in a gray scale, a dark portion of the inside of the container corresponds to pink. From this, it has been found that as the nitrite ion-containing LDH powdery sample comes in contact with the air, it causes nitrous acid vapor to be generated.

Further according to the absorption spectra of FIG. 8, the adsorption spectra before aeration (bubbling) had no adsorption peak in the wavelength range under measurement, but after aeration (bubbling), there was a clear absorption peak appearing near 543 nm. This peak is consistent with an absorption peak coming from an azo dye formed by reaction of nitrite ions with Griess reagent. From this too, it has been identified that the nitrite ion-containing LDH powdery sample generates nitrous acid vapor by coming in contact with the air, that is, a gas containing carbon dioxide and water vapor.

Example 2

Figure 9:
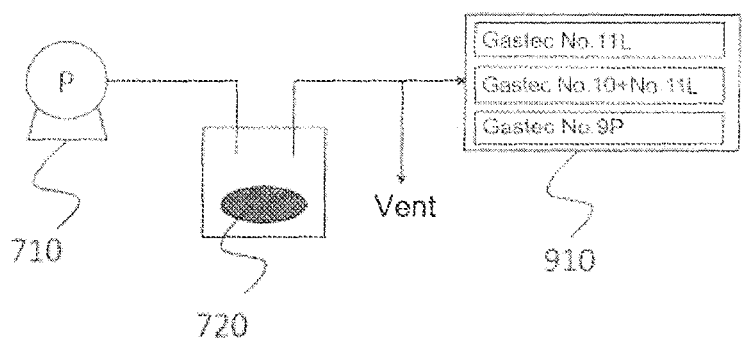
FIG. 9 is a schematic view illustrating an apparatus and experimental system used in Example 2.

Then, the apparatus shown in FIG. 9 was used together with the nitrite ion-containing LDH obtained in Example 1 to carry out nitrogenous gas sustained release experimentation and measurement using a detector tube.

FIG. 9 is a schematic view illustrative of the apparatus and experimental system used in Example 2.

Specifically, the pump 710 was used to feed the air (20° C., a relative humidity of 35%) to the nitrite ion-containing LDH powdery sample 720 (100 mg) in the glass container at a flow rate of 100 mL/min for an about 1-hour stabilization, after which components in the gas coming in contact with the nitrite ion-containing LDH were measured using various detector tubes 910. It is here noted that the pump 710 was used to feed the air (20° C., a relative humidity of 35%) into the nitrite ion-containing LDH powdery sample at a flow rate of 100 mL/min, but an air portion of 50 mL/min was sucked by the detector tube 910 if required, while the remaining portion of 50 mL/min was let go out via a branched line.

First of all, detector tube No. 11L (for $NO+NO_2$) made by Gastec Corporation was used to measure the total quantity of nitrogen monoxide+nitrogen dioxide+nitrous acid vapor. Detector tube No. 11L made by Gastec Corporation, having a strong oxidizing agent ($Cr^{3+}$+sulfuric acid) at its tip, is designed to convert nitrogen monoxide into nitrogen dioxide, and then determine the total quantity of nitrogen dioxide by orthotolidine. For this reason, nitrous acid vapor was also converted into nitrogen dioxide that was then determined as the total quantity of nitrogen dioxide. A metering pump used exclusively with detector tubes (GSP-300FT-2 made by Gastec Corporation) was used for a 4-minute suction at a flow rate of 50 mL/min to find that the concentration of nitrogen monoxide+nitrogen dioxide+nitrous acid vapor was 0.7 ppm.

Subsequently, detector tube No. 9P (for $NO_2$) made by Gastec Corporation was used to measure only nitrogen dioxide. Unlike the aforesaid detector tube No. 11L, detector tube No. 9P is not provided at its tip with any oxidizing agent ($Cr^{3+}$+sulfuric acid); it is designed to determine the quantity of nitrogen dioxide alone by orthotolidine. A metering pump used exclusively with detector tubes was used for a 30-minute suction at a flow rate of 100 mL/min to find that the concentration of nitrogen dioxide was 0.2 ppm.

Subsequently, detector tube No. 10 (for $NO_2$) made by Gastec Corporation was coupled to detector tube 11L (for $NO+NO_2$) made by Gastec Corporation to remove nitrogen dioxide and nitrous acid vapor by orthotolidine contained in detector tube No. 10 (for $NO_2$) made by Gastec Corporation, after which detector tube No. 11L (for $NO+NO_2$) was used to measure nitrogen monoxide alone. A metering pump used exclusively with detector tubes was used for a 4-minute suction at a flow rate of 50 mL/min to find that the concentration of nitrogen monoxide was 0.2 ppm.

The fact that nitrogen monoxide and nitrogen dioxide have much the same concentration shows that two such gases are formed by the self-oxidation-reduction reaction ($2HNO_2 \rightarrow NO_2+NO+H_2O$).

These results are summed up as described below.

Gastec No. 11L ($NO+NO_2+HNO_2$=0.7 ppm)
Gastec No. 10+No. 11L (NO=0.2 ppm)
Gastec No. 9P ($NO_2$=0.2 ppm)
$HNO_2$=0.3 ppm From the aforesaid results showing that nitrogen monoxide+nitrogen dioxide+nitrous acid vapor=0.7 ppm, nitrogen dioxide=0.2 ppm and nitrogen monoxide=0.2 ppm, nitrous acid vapor was calculated by subtraction as 0.3 ppm.

It is here noted that the concentration of released nitrogen monoxide, nitrogen dioxide and nitrous acid vapor reached a maximum about 15 to 30 minutes after the start of release but, even when release was kept going on for a further 6 hours, the maximum concentration was nearly maintained, showing that the nitrite ion-containing LDH could sustainably release off nitrogen monoxide, nitrogen dioxide and nitrous acid vapor.

Example 3

Figure 10:
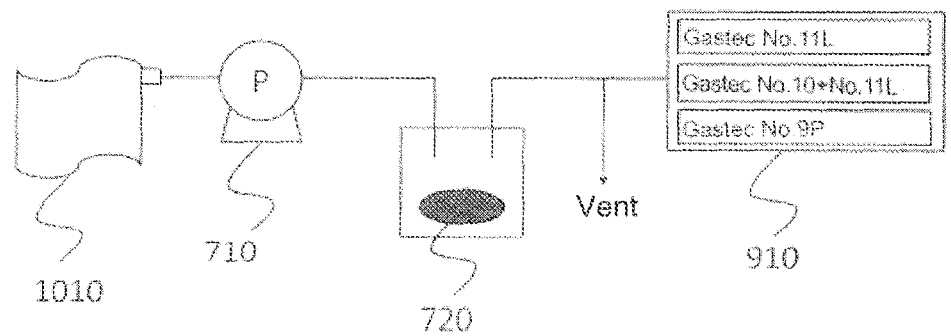
FIG. 10 is a schematic view illustrating an apparatus and experimental system used in Example 3.

The nitrite ion-containing LDH obtained in Example 1 was used with the apparatus shown in FIG. 10 for nitrogenous gas release experimentation, and compositions of released gases were measured by a detector tube 910.

FIG. 10 is a schematic view showing the apparatus and experimental system used in Example 3.

The operation of Example 3 is much the same as that of Example 2 with the exception that exhaled air (20° C., a carbon dioxide concentration of 4.0%, and a relative humidity of 100%) stored in 50L Tedlar bag 1010 rather than air was fed at a flow rate of 100 mL/min, using the pump 710.

Because the exhaled air had a relative humidity of 100% higher than an acceptable humidity range (0 to 90%) for detector tubes, the relative humidity was regulated to 50% by mixing with the same amount (100 mL/min) of dry air. Accordingly, the release concentration was corrected by doubling the detected value.

The post-correction values are summed up as follows.
Gastec No. 11 ($NO+NO_2+HNO_2=7.0$ ppm)
Gastec No. 10+No. 11L ($NO=1.0$ ppm)
Gastec No. 9P ($NO_2=1.1$ ppm)
$HNO_2=5.9$ ppm The post-correction concentration was 1.0 ppm for nitrogen monoxide, 1.1 ppm for nitrogen dioxide, and 5.9 ppm for nitrous acid vapor, indicating that release concentrations were more improved as compared with Example 2. In this case, too, nitrogen monoxide and nitrogen dioxide had much the same concentration, showing that two such gases were formed by the self-oxidation-reduction reaction of nitrous acid ($2HNO_2 \rightarrow NO_2+NO+H_2O$).

From this, it has been found that the nitrite ion-containing LDH is capable of releasing off a high concentration of nitrogenous gases upon coming in contact with a gas containing much carbon dioxide and water vapor.

Example 4

Figure 11:
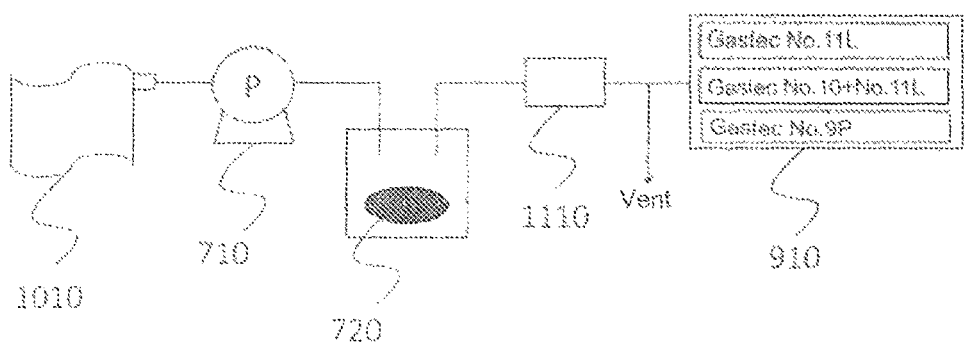
FIG. 11 is a schematic view illustrating an apparatus and experimental system used in Example 4.

The apparatus shown in FIG. 11 was used to carry out nitrogenous gas release experimentation with the nitrite ion-containing LDH obtained in Example 1 to measure the compositions of released gases by the detector tube 910.

FIG. 11 is a schematic view showing the apparatus and experimental system used in Example 4.

The operation of Example 4 is much the same as that of Example 3 except that exhaled air coming in contact with the nitrite ion-containing LDH (100 mg) was aerated through a Pasteur column 1110 loaded up with 750 mg or 1500 mg of iron (II) sulfate heptahydrate (made by Fujifilm Wako Pure Chemical Corporation). Iron (II) sulfate heptahydrate loaded up in the Pasteur column 1110 made of 2 mL glass had a length of about 3 cm (in the case of a loading amount of 750 mg).

The results in the case where the loading amount of iron (II) sulfate heptahydrate is 750 mg are summed up as mentioned below.
Gastec No. 11 ($NO+NO_2+HNO_2=7.0$ ppm)
Gastec No. 10+No. 11 ($NO=6.6$ ppm)
Gastec No. 9P ($NO_2=0.55$ ppm)
$HNO_2=0$ ppm From the foregoing results: 6.6 ppm for nitrogen monoxide, 0.55 ppm for nitrogen dioxide and 7.0 ppm for nitrogen monoxide+nitrogen dioxide+nitrous acid vapor, it has been found that the concentration of nitrous acid vapor is substantially equal to zero, and nitrous acid vapor can be converted into nitrogen monoxide by passing it through the Pasteur column loaded up with iron (II) sulfate heptahydrate.

It is here noted that when the amount of iron (II) sulfate heptahydrate loaded up in the Pasteur column was doubled (with a length of about 6 cm), there was no change in the concentration of nitrogen monoxide product. From this, it is preferable to place the upper limit of iron (II) sulfate heptahydrate relative to the nitrite ion-containing LDH on 1700% by mass.

Example 5

Figure 12:
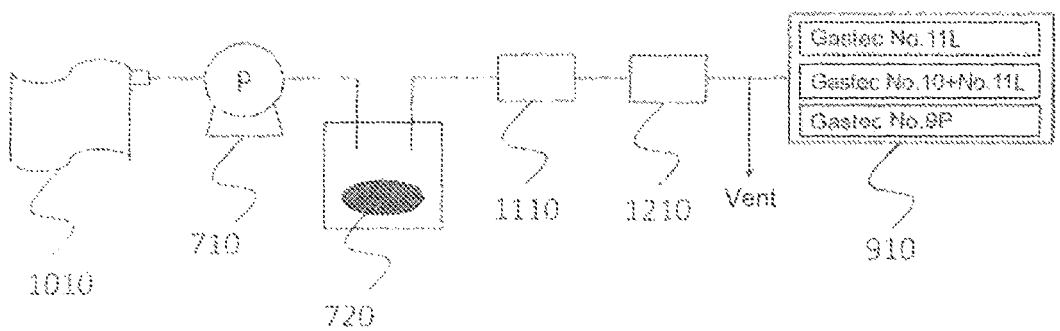
FIG. 12 is a schematic view illustrating an apparatus and experimental system used in Example 5.

The apparatus shown in FIG. 12 was used to perform nitrogenous gas release experimentation with the nitrite ion-containing LDH obtained in Example 1 to measure compositions of released gases by the detector tube 910.

FIG. 12 is a schematic view showing the apparatus and experimental system used in Example 5.

The operation of Example 5 is the same as that of Example 4 except that exhaled air coming in contact with the nitrite ion-containing LDH was aerated through the Pasteur column 1110 loaded up with 750 mg of iron (II) sulfate heptahydrate and further aerated through a Pasteur column 1210 loaded up with 250 mg of magnesium hydroxide (Kanto Chemical Industry Co., Inc.). Again, iron (II) sulfate heptahydrate and magnesium hydroxide loaded up in the Pasteur columns had a length of about 3 cm.

The results are summed up as below.
Gastec No. 11 ($NO+NO_2+HNO_2=4.0$ ppm)
Gastec No. 10+No. 11 ($NO=4.0$ ppm)
Gastec No. 9P ($NO_2=0.02$ ppm)
$HNO_2=0$ ppm From the foregoing results: 4.0 ppm for nitrogen monoxide, 0.02 ppm for nitrogen dioxide and 4.0 ppm for nitrogen monoxide+nitrogen dioxide+nitrous acid vapor, it has been found that the concentration of nitrous acid vapor is substantially equal to zero, and the concentration of nitrogen dioxide can be greatly reduced down. This has been considered to be due to the fact that nitrogen monoxide, because of being neutral, passes through magnesium hydroxide with no reaction, whereas nitrogen dioxide and nitrous acid vapor, because of being each an acidic gas, are removed by neutralization reaction with magnesium hydroxide. This has revealed that by passing the gases through the columns loaded up with iron (II) sulfate heptahydrate and magnesium hydroxide, it is possible to generate high-purity nitrogen monoxide substantially free from impurities such as nitrogen dioxide and nitrous acid.

It is here noted that the concentration of released nitrogen monoxide reached a maximum about 15 to 30 minutes after the start of release but, even when release was kept going on for a further 6 hours, the maximum concentration was nearly maintained, showing that the nitrite ion-containing LDH could sustainably release off nitrogen monoxide.

Example 6

Figure 13:
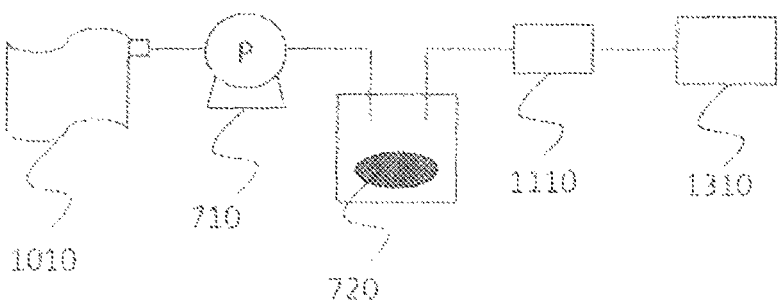
FIG. 13 is a schematic view illustrating an apparatus and experimental system used in Example 6.

In Example 6, the apparatus shown in FIG. 13 was used to perform nitrogenous gas release experimentation with the nitrite ion-containing LDH obtained in Example 1 to measure compositions of released gases by an electrochemical nitrogen monoxide sensor.

FIG. 13 is a schematic view showing the apparatus and experimental system used in Example 6.

The operation of Example 6 is much the same as that of Example 4 except that exhaled air (50 mL/min) coming in contact with the nitrite ion-containing LDH (100 mg) was aerated through the Pasteur column 1110 loaded up with 750 mg of iron (II) sulfate heptahydrate, after which an electrochemical nitrogen monoxide sensor ((TOXIRAE Pro with a detection range of 0.5 to 250 ppm)) 1310 was introduced in place of the detector tube 910.

While iron (II) sulfate heptahydrate loaded up in the Pasteur column 1110 was periodically replaced with new one, the concentration of nitrogen monoxide was measured over 15 days. The results are shown in FIG. 14, and shown in FIG. 15b are infrared absorption spectra of the nitrite ion-containing LDH before contact and, 2 weeks after contact, with exhaled air.

FIG. 14 is a view showing time-dependent concentration change of nitrogen monoxide released off in Example 6.

In FIG. 14, arrows are indicative of iron (II) sulfate heptahydrate replacement timing. According to FIG. 14, release of nitrogen monoxide was kept going on over two weeks or longer with a concentration half-life of about 6 days, revealing that the inventive nitrite ion-containing LDH could have enhanced nitrogenous gas sustained releasability and function as a nitrogenous gas sustained releasing agent.

This enhanced nitrogen dioxide sustained releasability would provide a promising method of feeding low-concentration nitrogen monoxide for an extended period time and, combined with equipment such as a metering pump or a nitrogen monoxide sensor, would show promise as home treatment equipment for pulmonary hypertension as an example.

Referring here to the nitrite ion-containing LDH of Example 6 before and after contact with exhaled air, FIG. 15 shows thermogravimetric (TG)·differential thermal analysis (DTA) profile (FIG. 15a), infrared absorption spectra (FIG. 15b), and powder X-ray diffraction profile (FIG. 15c), respectively.

In FIG. 15, (i) profile corresponds to carbonate type LDH, (ii) profile corresponds to Cl type LDH, (iii) profile corresponds to nitrite ion-containing LDH before contact with exhaled air, and (iv) profile corresponds to nitrite ion-containing LDH 2 weeks after contact with exhaled air.

In the infrared absorption spectra of FIG. 15b, a signal found near 1227 $cm^{-1}$ corresponds to a nitrite ion, and a signal found near 1360 $cm^{-1}$ corresponds to a carbonate ion. Before contact with exhaled air, the signals of nitrite ions were stronger than those of carbonate ions, but two weeks after contact with exhaled air, there was a reduction in the signals of nitrite ions, rendering the signals of carbonate ion stronger. This result is supportive of a mechanism wherein nitrous acid vapor is released out of the nitrite ion-containing LDH by the solid phase-gas phase anion exchange reaction based on atmospheric carbon dioxide, explained with reference to FIG. 3, and carbonate ions remain in the LDH layers.

Examples 7-8

In Examples 7 and 8, nitrogenous gas release experimentation was carried out, while a mode of connection of the nitrite ion-containing LDH obtained in Example 1 with iron (II) sulfate heptahydrate was varied, to measure compositions of released gases by an electrochemical nitrogen monoxide sensor.

FIG. 16 is a schematic view illustrative of the apparatus and experimental system used in Example 7, and FIG. 17 is a schematic view illustrative of the apparatus and experimental system used in Example 8.

As depicted in FIG. 16, the apparatus used in Example 7 is assembled such that, in the apparatus used in Example 6, two or three glass containers, each containing 100 mg of a nitrite ion-containing LDH powdery sample 720, were connected with a Teflon® tube and a septum cap, and Pasteur columns 1110 as many as the aforesaid glass containers, each loaded up with 750 mg of iron (II) sulfate heptahydrate, were connected to the rear stages thereof. FIG. 16 shows an assembly where three nitrite ion-containing LDH powdery samples 720 are connected to three Pasteur columns 1110. In Example 7, such apparatus was used to introduce exhaled air at a flow rate of 50 mL/min, and then stabilized for 15 minutes to measure the concentration of nitrogen monoxide in released gases by an electrochemical nitrogen monoxide sensor. The results are shown in a white bar graph in FIG. 18.

As depicted in FIG. 17, on the other hand, the apparatus used in Example 8 is assembled such that, in the apparatus used in Example 6, two or three sets, each comprising a glass container containing 100 mg of a nitrite ion-containing LDH powdery sample 720 and a Pasteur column 1110 loaded up with 750 mg of iron (II) sulfate heptahydrate, are alternately connected together using a Teflon® tube. FIG. 17 shows that three sets, each comprising a glass container containing 100 mg of a nitrite ion-containing LDH powdery sample 720 and a Pasteur column 1110 loaded up with 750 mg of iron (II) sulfate heptahydrate, are connected together in place. In Example 8, the concentration of nitrogen monoxide in released gases was measured under the same conditions as in Example 7 by an electrochemical nitrogen monoxide sensor. The results are given in a shadowed bar graph in FIG. 18.

FIG. 18 is indicative of relations of the number of glass containers and Pasteur columns 1110 to the concentration of nitrogen monoxide released in Examples 7 and 8.

In any assembly of Examples 7 and 8, as the number of glass containers and Pasteur columns 1110 increased, the concentration of nitrogen monoxide tended to increase.

In the assembly of Example 7, however, the rate of increase in nitrogen monoxide concentration was not in direct proportion to the number of glass containers and Pasteur columns 1110; it tended to increase gradually. In the assembly of Example 8, on the other hand, the concentration of nitrogen monoxide tended to increase in direct proportion to the number of glass containers and Pasteur columns 1110.

This would be considered due to no saturation of equilibrium of nitrous acid production because, per set of glass container and Pasteur column, nitrous acid vapor is converted by iron (II) sulfate heptahydrate into nitrogen monoxide. This would show that if a proper way is figured out to combine the nitrite ion-containing LDH with the reducing agent, that is, if the construction of the nitrogenous gas releaser is properly determined, it would then be possible to release off high-concentration nitrogen monoxide in a sustained way.

Example 9

The apparatus shown in FIG. 19 was used to perform nitrogenous gas release experimentation with a mixture of the nitrite ion-containing LDH obtained in Example 1 with iron (II) sulfate heptahydrate thereby measuring compositions of released gases with the aid of an electrochemical nitrogen monoxide sensor and a detector tube.

FIG. 19 a schematic view showing the apparatus and experimental system used in Example 9.

The apparatus of FIG. 19 was assembled such that, in the apparatus depicted in FIG. 6, the atmospheric gas feeding portion 610 was changed to a pump 710 and a 30-mL plastic syringe 1910 loaded up with water-wetted gauze for humidification, the nitrogenous gas sustained releasing portion 620 was changed to a 3-mL plastic syringe 1920 loaded up with a mixture of the nitrite ion-containing LDH powdery sample obtained in Example 1 with iron (II) sulfate heptahydrate with cotton wool put in, and the impurity gas removal portion 630 was changed to a 12-mL plastic syringe 1210 loaded up with 4 grams of magnesium hydroxide. In the apparatus of FIG. 19, a filter 730 is also set before and after the plastic syringe 1210 to prevent powders from entering the syringe 1210 from the plastic syringe 1920. Further, a check valve was located to the rear stage of the plastic syringe 1210 for backflow prevention.

There were two plastic syringes 1920 provided: one loaded up with a mixture of 100 mg of nitrite ion-containing LDH powders with 1.0 g of iron (II) sulfate heptahydrate, and another loaded up with a mixture of 50 mg of nitrite ion-containing LDH powders with 0.5 g of iron (II) sulfate heptahydrate. The nitrite ion-containing LDH, and iron (II) sulfate heptahydrate was powdered using an agate mortar, followed by mixing.

The apparatus was operated as described below. The pump 710 was used to feed the air at a flow rate of 100 mL/min for aeration through the plastic syringe 1910 for the purpose of humidification. After humidification, there was a relative humidity of 93% as actually measured. This humidified air was aerated through the plastic syringe 1920 and plastic syringe 1210 in this order. After aeration through the syringe 1210 at a flow rate of 100 mL/min, the gas was mixed with 4 L/min of the air, and then introduced in the electrochemical nitrogen monoxide sensor 1310 or detector tube 1930 to measure the concentration of nitrogen monoxide or nitrogen dioxide. The results are shown in FIGS. 20 and 21.

FIG. 20 shows states of the mixture in the plastic syringe 1920 in Example 9 before and after nitrogenous gas release experimentation.

An area indicated by a dotted line in FIG. 20 is indicative of the mixture. The mixture before use (release experimentation) presented a pale blue color, but turned into brown after use (release experimentation). In FIG. 20 given on a gray scale, a bright portion in the area indicated by a dotted line corresponds to pale blue, and a dark portion corresponds to brown. This coloring reaction is based on the oxidation of iron (II) sulfate heptahydrate in the mixture, and it suggests that divalent iron ions function as a reducing agent because divalent iron ions before release experimentation turn into trivalent iron ions after release experimentation. This coloring reaction can be used for qualitative determination of the nitrogenous gas sustained releaser in general, and storage states of nitrogen monoxide sustained releaser and sustained release state of nitrogen monoxide in particular.

Figure 21:
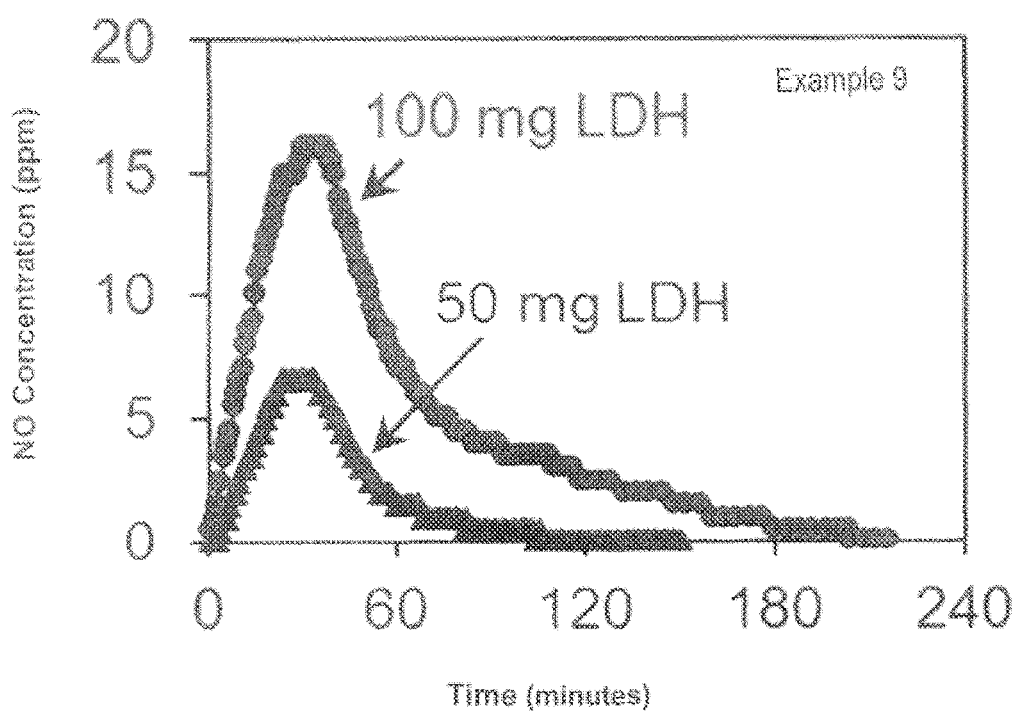
FIG. 21 shows time-dependent concentration change of nitrogen monoxide released off in Example 9.

FIG. 21 shows time-dependent concentration change of nitrogen monoxide released off in Example 9.

According to FIG. 21, it has been indicated that with 100 mg of the nitrite ion-containing LDH, a maximum of 16 ppm of nitrogen monoxide can be sustainably released off in air at a flow rate of 4.1 L/min., and it has been revealed that a concentration (5 to 20 ppm) and respiratory volume (about 0.5 L/min. for newborns and about 2.5 L/min. for infants) applicable to nitrogen monoxide inhalation is achievable. With 50 mg of the nitrite ion-containing LDH, it has been shown that the sustained release concentration of nitrogen monoxide reduces by about half, and by quantitative regulation of the nitrite ion-containing LDH, the concentration of nitrogen monoxide can be increased/decreased to make it easy to obtain the desired nitrogen monoxide concentration.

According to FIG. 21, it has been seen that nitrogen monoxide having a concentration of 0.16 ppm, 1/100 of a maximum of 16 ppm, is continuously detected for 30 minutes or longer. Accordingly, the mixture of the nitrite ion-containing LDH powders with iron (II) sulfate heptahydrate used here provides a nitrogenous gas sustained releaser having nitrogen monoxide sustained releasability.

The concentration of nitrogen dioxide coexisting with 16 ppm of nitrogen monoxide was found to be a maximum of 0.075 ppm as a result of measurement by a detector tube (Gastec No. 9P), which was much lower than 0.2 ppm: environmental standards prescribed for 8-hours workers.

By calculation, the concentration of nitrogen monoxide generated out of 100 mg of nitrite ion-containing LDH and 1 g of iron (II) sulfate heptahydrate was found to be a maximum of 640 ppm at a flow rate of 100 mL/min As this is mixed with 4 L/min of air, it would be diluted up to 5 to 16 ppm.

Example 10

In Example 10, $CO_3^{2-}$-MgAl-LDH2 containing Mg ions as the divalent metal ions and Al ions as the trivalent metal ions and represented by the general formula: $Mg_2Al(OH)_6(CO_3^{2-})_{0.5} \cdot 2H_2O$ was used as the carbonate type LDH in place of $CO_3^{2-}$-MgAl-LDH3 used in Example 1. $CO_3^{2-}$-MgAl-LDH2 was synthesized by the process described in JP(A) 2005-335965.

Specifically, $MgCl_2 \cdot 6H_2O$ (508 mg) and $AlCl_3 \cdot 6H_2O$ (302 mg) were first weighed, and ion exchange water was then added to them to prepare 12.5 mL of a solution. Then, 12.5 mL of an aqueous solution of hexamethylenetetramine (613 mg) was, added to the solution and mixed. Then, the resulting mixed solution was filtrated through a membrane filter having a pore diameter of 0.2 μm, then placed in a 50-mL pressure-resistant Teflon® container, then placed and sealed up in a pressure-resistant stainless container, and finally hydrothermally treated at 140° C. for one day. The hydrothermally treated liquid mixture was filtrated, and the residues were washed with water and finally dried in vacuo to obtain 279 mg of white powders.

The thus obtained white powders had a particle diameter of about 0.5 to 2 μm and a Mg/Al molar ratio of 1.94 (±0.04), and the Fourier transform infrared absorption (FTIR) spectrum is consistent with the profile already on report (for instance, Japanese Patent Application No. 2018-132081).

Then, the obtained carbonate type LDH ($CO_3^{2-}$-MgAl-LDH2) was converted into Cl type LDH, as detailed just below. First, 1.15 g of $CO_3^{2-}$-MgAl-LDH2 were weighed, and then placed in a three-neck flask, to which 200 mL of methanol were added to prepare a suspension. While this suspension was stirred by a magnetic stirrer under a nitrogen flow (500 mL/min), 9.0 mL of a hydrochloric acid alcohol solution (3% by mass) were added dropwise to the solution for a two-hour reaction at 35° C. under stirring. Finally, filtration, washing and drying were carried out under the same conditions as in the preparation of the Cl type LDH in Example 1, thereby obtaining 984 mg of white powders.

There was no absorption of 1360 cm$^{-1}$ attributable to carbonate ions ($CO_3^{2-}$) observed as a result of measurement of Fourier transform infrared absorption (FTIR) spectra of the obtained white powders; carbonate ions were judged as being substituted by chloride ions. Hereafter, this LDH will be referred to as Cl⁻MgAl-LDH2.

Then, the nitrite ion-containing LDH was produced from Cl⁻MgAl-LDH2. Under the air, 400 mg of Cl⁻MgAl-LDH2 were placed in a three-neck flask that was then fully substituted inside by dry nitrogen. One hundred and fifty (150) mL of ion exchange water degassed by a syringe were placed in the flask for thorough dispersion of Cl⁻MgAl-LDH2, and 1.89 grams of NaNO$_2$ (made by Wako Pure Chemical Corporation) was dissolved in 30 mL of degassed ion exchange water to prepare a NaNO$_2$ solution. The NaNO$_2$ solution was added in the flask using a syringe and stirred for one day, after which stirring was stopped and the solution was let stand for one day. The solution was then filtrated through a membrane filter having a pore diameter of 0.2 μm, and the residues were washed with degassed ion exchange water, further washed with methanol, evacuated together with the membrane filter, and dried in vacuo for about 120 minutes to obtain a white powdery sample.

FTIR measurement of the white powdery sample was carried out, and as a result of observation of sufficient absorption of 1227 cm$^{-1}$ by nitrite ions (NO$_2^-$), it was judged that chloride ions were substituted by nitrite ions, yielding the nitrite ion-containing LDH. As a result of measurement of Mg/Al ratios by SEM-EDS (JSM6010LA made by JEOL Ltd., 10 kV), it was found that the Mg/Al ratio of the starting carbonate type LDH was maintained. Cl was about 8 to 9% relative to Al, which supported that the anion exchange from Cl$^-$MgAl-LDH2 to the nitrite ion-containing LDH was fully accomplished. X-ray diffraction pattern and TG-DTA profile (ThemoPlus 8120 made by RIGAKU) were characteristic of a layered double hydroxide, showing that anion exchange took place from the starting carbonate type LDH(Mg$_2$Al(OH)$_8$(CO$_3^{2-}$)$_{0.5}$·2H$_2$O) with no destruction of the layered structure. From this, it has been judged that the obtained nitrite ion-containing LDH satisfies the aforesaid general formula (1).

Then, a package having the nitrite ion-containing LDH sealed up and contained therein was produced. In a glove box, the obtained white nitrite ion-containing LDH powdery sample was placed and tightly capped in a 13.5 mL glass container (wrapping material) together with the membrane filter to form a package.

Figure 22:
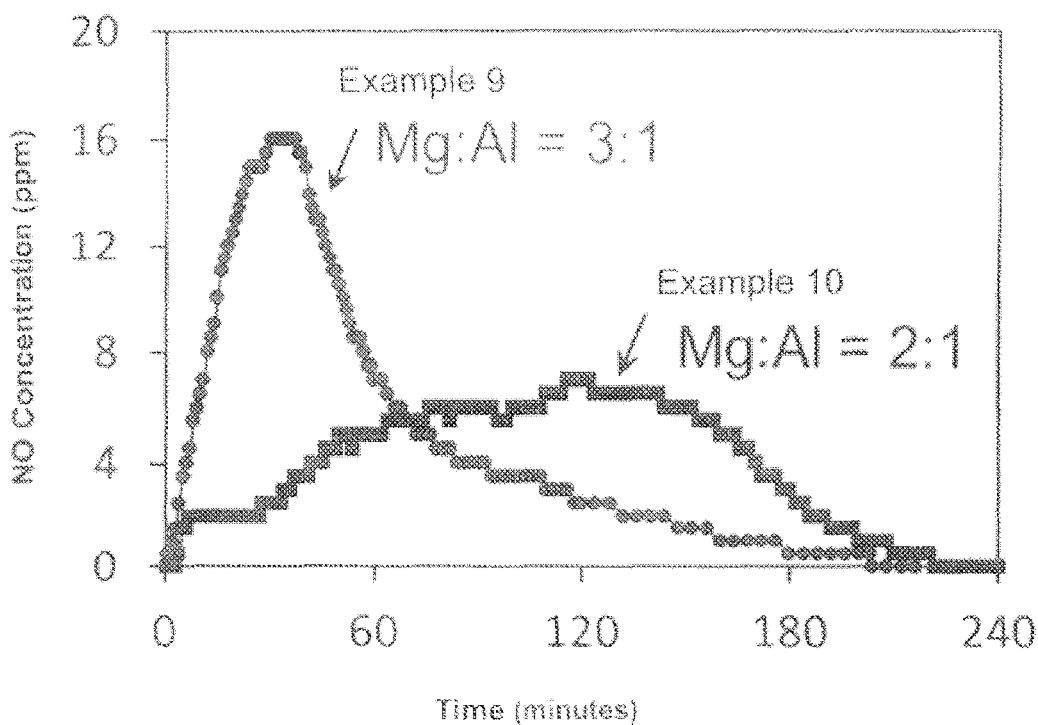
FIG. 22 shows time-dependent concentration change of nitrogen monoxide released off in Example 10.
Figure 23:
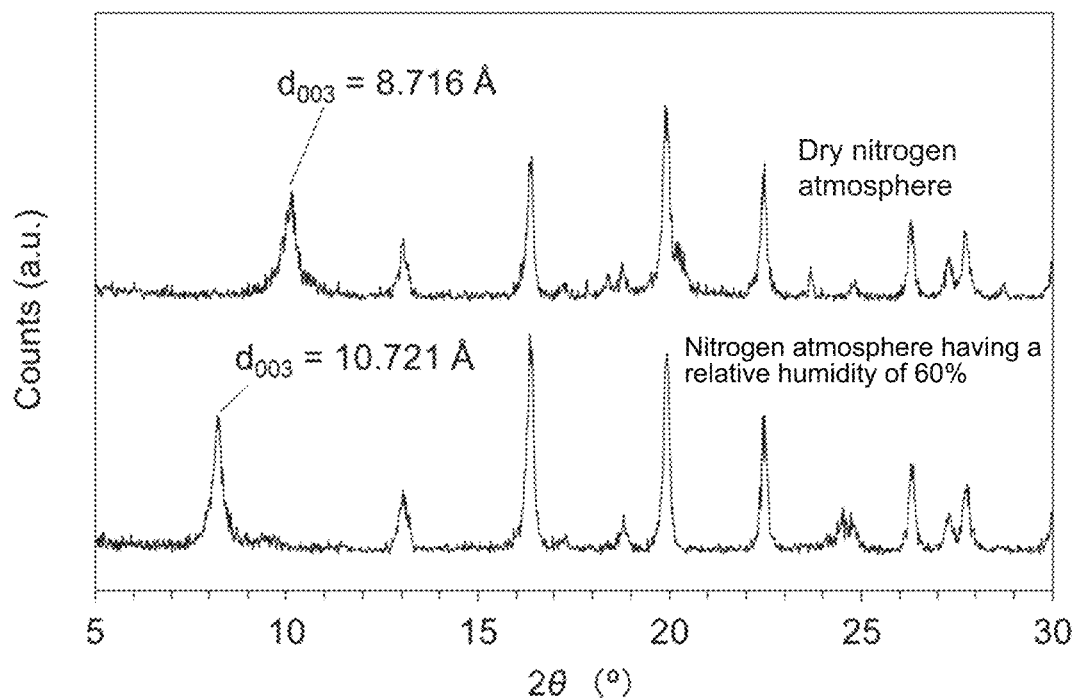
FIG. 23 shows an XRD pattern of a mixture after release experimentation in Example 10.

The nitrite ion-containing LDH was taken out of the obtained package, and a nitrogenous gas releasing apparatus was assembled. Referring here to the nitrogenous gas releasing apparatus used in Example 10, the apparatus used in Example 9 and shown in FIG. 19 was modified such that the plastic syringe 1920 was loaded up with a mixture of 100 mg of a nitrite ion-containing LDH powdery sample synthesized from Cl$^-$MgAl-LDH2 with 1.0 g of powdery iron (II) sulfate heptahydrate to measure the concentration of nitrogen monoxide in released gases with the use of the electrochemical nitrogen monoxide sensor 1310. The results are shown in FIG. 22. Further, the mixture state after release experimentation was visually checked up and its X-ray diffraction (XRD) pattern was measured using a powder X-ray diffraction device (made by RIGAKU, Model No. RINT-2200V). The obtained XRD pattern is shown in FIG. 23.

FIG. 22 shows time-dependent concentration change of nitrogen monoxide released off in Example 10.

FIG. 22 also shows time-dependent concentration change of nitrogen monoxide released off in Example 9 (FIG. 21). According to FIG. 22, the use of the nitrite ion-containing LDH (Example 10) synthesized from Cl$^-$MgAl-LDH2 rendered the releasing concentration of nitrogen monoxide smoother and the sustained releasing time longer as compared with the use of the nitrite ion-containing LDH (Example 9) synthesized from Cl$^-$MgAl-LDH3, showing that the sustained releasing concentration and time of nitrogen monoxide can be controlled by regulation of the nitrite ion/nitrate ion-containing LDH composition (for instance, "Q", "R", "Z", "x", "d", "g", j or the like in the aforesaid formula (1)).

Although not indicated in FIG. 22, the mixture before release experimentation showed a pale blue color, but it turned brown after use (release experimentation), as in Example 9. This also suggests that the divalent iron ion functions as a reducing agent.

FIG. 23 shows XRD patterns of the mixture after release experimentation in Example 10.

FIG. 23 shows XRD patterns of mixtures of nitrite ion-containing LDH powders with iron (II) sulfate heptahydrate after release experimentation, as measured under dry nitrogen and a nitrogenous atmosphere having a relative humidity of 60%, respectively. The basal plane spacing (spacing $d_{003}$ of (003) plane), as calculated out with this result in mind, was 8.72 Å under dry nitrogen, and 10.72 Å under a nitrogen atmosphere having a relative humidity of 60%. These values were very close to ones, 8.58 Å under a dry nitrogen atmosphere, and 10.94 Å under a nitrogen atmosphere having a relative humidity of 60%, that have been reported as the basal plane spacing and relative humidity responsibility of LDH (Mg:Al=2:1) having sulfate ions between layers in Non-Patent Publication 4.

This result means that between the nitrite ion-containing LDH and iron (II) sulfate heptahydrate, solid phase-solid phase anion exchange reaction takes place, resulting in release of nitrite ions from the nitrite ion-containing LDH to the outside and introduction of sulfate ions between LDH layers, and lends support to the nitrogenous gas sustained release mechanism based on solid phase-solid phase anion exchange reaction.

Example 11

In Example 11, the mixture of nitrite ion-containing LDH obtained in Example 1 with iron (II) sulfate heptahydrate was used to produce medical respiratory equipment.

Figure 24:
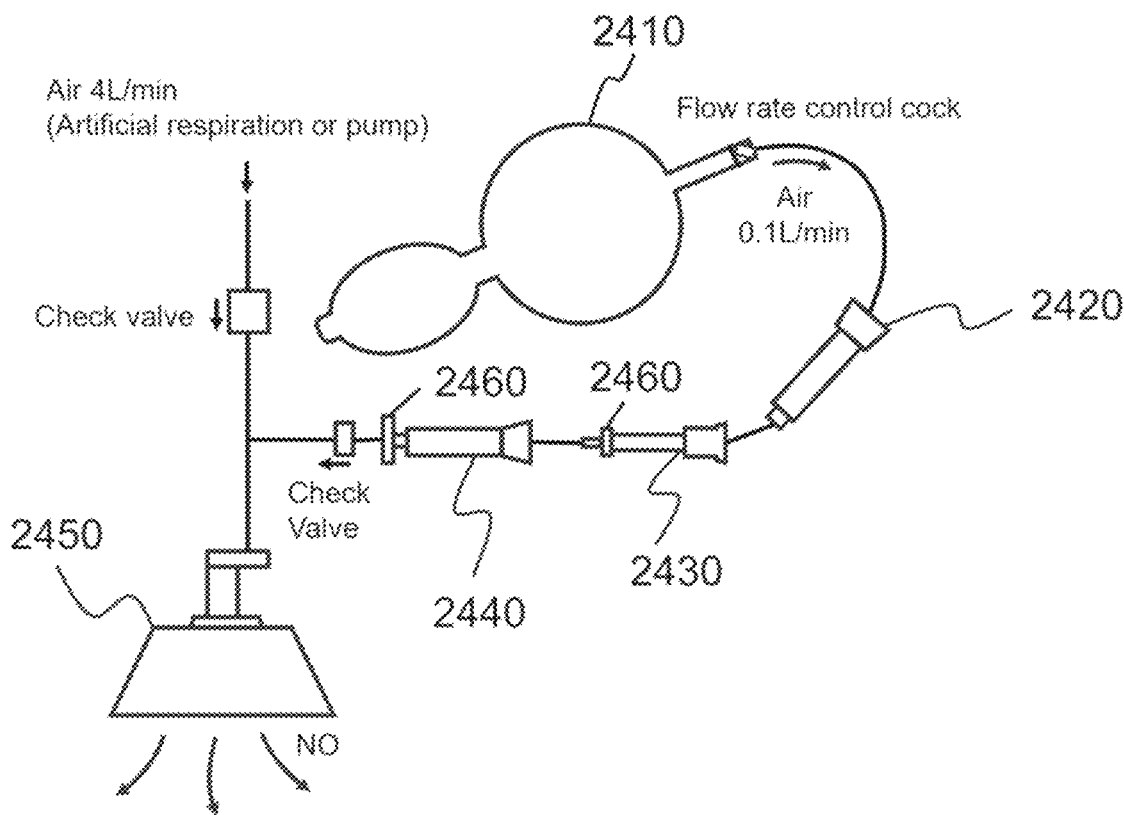
FIG. 24 shows medical respiratory equipment in Example 11.

FIG. 24 shows medical respiratory equipment according to Example 11.

The respiratory equipment comprises a hand pump 2410 including a flow rate control cock, a humidifier 2420, a nitrogenous gas sustained releaser 2430 according to the invention, an adsorbent 2440, and a ventilator 2450. Filters 2460 were set before and after the adsorbent 2440 to prevent entrance of powders, and some check valves were optionally set for prevention of backflows.

As in Example 9, a 30-mL plastic syringe loaded up with water wetted gauze was used as the humidifier 2420, and the mixture of nitrite ion-containing LDH (100 mg) obtained in Example 1 with iron (II) sulfate heptahydrate (1.0 g) was used as the nitrogenous gas sustained releaser 2430. As in Example 9, a 12-mL plastic syringe loaded up with 4 grams of magnesium hydroxide was used as the adsorbent 2440. The filter 2460 used here had a pore diameter of 0.45 μm.

An air (0.1 L/min.) was fed from the hand pump 2410 into the humidifier 2420, the humidified air was fed into the nitrogenous gas sustained releaser 2430 to sustainably release off the nitrogenous gases, and nitrogen monoxide coming through the adsorbent 2440 was mixed with air and then fed into the ventilator 2450. The concentration of nitrogen monoxide fed from the ventilator 2450 was in a range of 5 ppm to 20 ppm as measured by an electrochemical nitrogen monoxide sensor. It has thus be understood that with this respiratory equipment, it is possible to feed nitrogen monoxide having the concentration required in medical levels by manual operation alone without recourse to any power source such as a battery whatsoever at all.

If the nitrogenous gas sustained releasing agent or releaser according to the invention is used, it is then possible to provide medical respiratory equipment usable as a nitrogen monoxide feeding means that is storable at room temperature and portable as well. By increasing the amount of a mixture of powdery nitrite ion-containing LDH with iron (II) sulfate heptahydrate or increasing the number of syringes each containing a mixture of powdery nitrite ion-containing LDH with iron (II) sulfate heptahydrate, it is possible not only to feed nitrogen monoxide in higher concentrations but also to feed nitrogen monoxide in medical level concentrations (5 to 20 ppm) to ventilators even under a flow rate of 4 L/min. or higher. If a syringe or its equivalent containing a mixture of powdery nitrite ion-containing LDH with iron (II) sulfate heptahydrate is periodically replaced in a manual or mechanical way, it is then possible to feed nitrogen monoxide over a longer period of time.

Example 12

In Example 12, nitrate ion-containing LDH was synthesized out of the carbonate type LDH ($CO_3^{2-}$-MgAl-LDH3) used in Example 1 according to the process described in Non-Patent Publication 5.

One hundred (100) mg of $CO_3^{2-}$-MgAl-LDH3 were weighed and placed together with 40 mL of methanol in a three-neck flask to prepare a suspension. While this suspension was stirred by a magnetic stirrer under a nitrogen flow (500 mL/min), 10 mL of methanol having 132.5 mg of ammonium nitrate dissolved therein were added dropwise to the suspension for a 1-hour reaction at room temperature with stirring. Then, filtration, washing and drying were carried out under the same conditions as was the case with the Cl type LDH obtained in Example 1 to obtain a white powdery sample.

The Fourier transform infrared absorption (FTIR) spectra and XRD patterns of the obtained white powdery sample conformed to those already on report (for instance, Non-Patent Publication 5). From this the obtained white powdery sample has been judged to be nitrate ion-containing LDH that is here referred to as $NO_3^-$-MgAl-LDH3.

Figure 25:
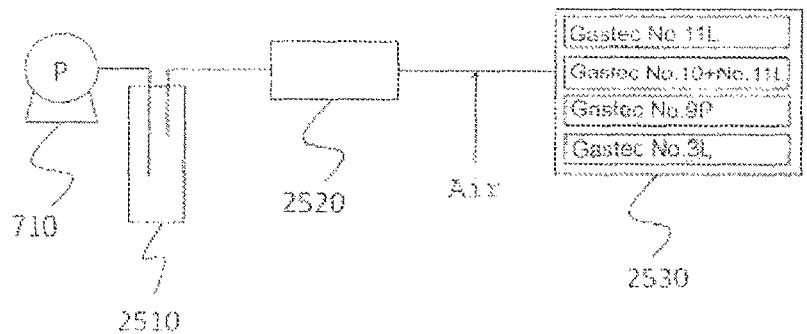
FIG. 25 is a schematic view illustrating an apparatus and experimental system used in Example 12.

The thus obtained nitrate ion-containing LDH was used to assemble the nitrogenous gas releasing apparatus shown in FIG. 25 to carry out nitrogenous gas release experimentation.

FIG. 25 is a schematic view illustrative of the apparatus and experimental system used in Example 12.

The apparatus shown in FIG. 25 comprises a pump 710, a humidifier 2510 that is a gas washing bottle containing water, and a 2-mL glass Pasteur pipette loaded up with the nitrogenous gas sustained releasing agent, and is designed such that nitrogenous gases are detected by a detector tube 2530. The Pasteur pipette 2520 is loaded up with a nitrogenous gas sustained releaser provided by a mixture comprising $NO_3^-$-MgAl-LDH3 (38.4 mg) powdered by a spatula, powdery iron (II) sulfate heptahydrate (384 mg) and sandy zinc (made by Nakalai Tesque, 3.84 g) with cotton wool put in. It is here noted that sandy zinc used has been washed with 0.1 mol/L of dilute hydrochloric acid to remove surface oxides, washed with pure water and methanol, and then fully dried in vacuo. Sandy zinc showed a silver metallic gloss after washed with hydrochloric acid.

The apparatus was operated as mentioned below. Using the pump 710, the air was fed at a flow rate of 100 mL/min and aerated through the gas washing bottle 2510 while bubbled in water for humidification. The humidified air was aerated through the Pasteur pipette 2520 loaded up with the nitrogenous gas sustained releaser. One hundred (100) mL/min of air passed through the Pasteur pipette 2520 were mixed with 100 mL/min of the air (with a relative humidity of 30%) to regulate the relative humidity in such a way as to come within a proper range of the detector tube 2530 (90% RH or lower). Thereafter, the concentrations of nitrogenous gases contained in the generated gases were measured by the detector tube 2530. The concentrations of nitrogenous gases displayed on the detector tube, because of being half the actual concentration, were doubled for correction. To keep the concentrations of released gases stable, humidified air was fed into the Pasteur pipette 2520 loaded up with the mixture comprising nitrate ion-containing LDH, iron (II) sulfate heptahydrate and sandy zinc at a flow rate of 100 mL/min for about 1 hour, followed by the start of measurement.

Detector tube No. 11L (for $NO+NO_2$) made by Gastec Corporation was used to measure the total amount of nitrogen monoxide+nitrogen dioxide+nitrous acid vapor. The amount of nitrogen monoxide+nitrogen dioxide+nitrous acid vapor was found to be 1.4 ppm as a consequence of carrying out suction for 4 minutes at a flow rate of 50 mL/min using a metering pump designed specifically for detector tubes. It is here noted that correction of doubling the value measured by the detector tube was applied to this value.

Subsequently, detector tube No. 9P (for $NO_2$) made by Gastec Corporation was used to measure the concentration of only nitrogen dioxide in the released gases. The concentration of nitrogen dioxide was found to be 0.06 ppm as a result of using a metering pump designed specifically for the detector tube to carry out suction for 10 minutes at a flow rate of 100 mL/min. It is here noted that correction of doubling the value measured by the detector tube was applied to this value.

Subsequently, detector tube No. 10 (for $NO_2$) made by Gastec Corporation was connected to detector tube No. 11L (for $NO+NO_2$) made by Gastec Corporation to measure the concentration of nitrogen monoxide in the released gases. After nitrogen dioxide and nitrous acid vapor were removed by orthotolidine contained in detector tube No. 10 (for $NO_2$) made by Gastec Corporation, a metering pump designed specifically for detector tubes was used to carry out suction for 4 minutes at a flow rate of 50 mL/min relative to detector tube No. 11L (for $NO+NO_2$) made by Gastec Corporation. As a result, the concentration of nitrogen monoxide was found to be 1.1 ppm. It is here noted that correction of doubling the value measured by the detector tube was applied to this value.

Subsequently, detector tube No. 3L (for ammonia) made by Gastec Corporation was used to measure the concentration of ammonia in the released gases. As a result of using a metering pump designed specifically for detector tubes to carry out suction for 2 minutes at a flow rate of 100 mL/min, there was no reaction observed at all: the concentration of ammonia was judged to be no greater than 0.2 ppm that was the detection limit of the detector tube.

Nitrous oxide ($N_2O$) was extracted from a high pressure cylinder (made by GL Science Inc.), and then mixed with the air in a Tedlar bag into a volume of about 10000 ppm, which was then sampled out using detector tube No. 11L (for $NO+NO_2$) or No. 9P (for $NO_2$). As a result, there was no reaction observed at all in either case: these detector tubes could be considered as being nonreactive with nitrous oxide.

The foregoing results are summed up just below.

Gastec No. 11L ($NO+NO_2+HNO_2$)=1.4 ppm)
Gastec No. 10+No. 11L (NO=1.1 ppm)
Gastec No. 9P ($NO_2$=0.06 ppm)
$HNO_2$=0.24 ppm In the present gas generation method, nitrate ions released from between the LDH layers are reduced by divalent iron ions and/or metal zinc into other nitrogenous gases. Referring here to the oxidation number of a nitrogen atom, it is +5 for nitrate ion, but +4 for nitrogen dioxide, +3 for nitrous acid, +2 for nitrogen monoxide, and +1 for nitrous oxide. From this, these chemical species would be considered as being mingled with one another depending on the degree of reduction of the starting nitrate ions. There would be reason to expect that if types and combinations of nitrate ion-reducing reagents and their applications are appropriately selected, it is then possible to sustainably release off only the desired nitrogenous gas or control the sustained releasing concentration and time.

Example 13

In Example 13, a mixture comprising the nitrate ion-containing LDH, iron (II) sulfate heptahydrate and sandy zinc that was obtained in Example 12, was used. The release experiment operation followed the procedure described in Example 9 using the apparatus shown in FIG. 19, with the exception that release experiment was performed without diluting the released gases with 4 L/min of air. The concentration of nitrogen monoxide in the released gases was measured by an electro-chemical nitrogen monoxide sensor.

Figure 26:
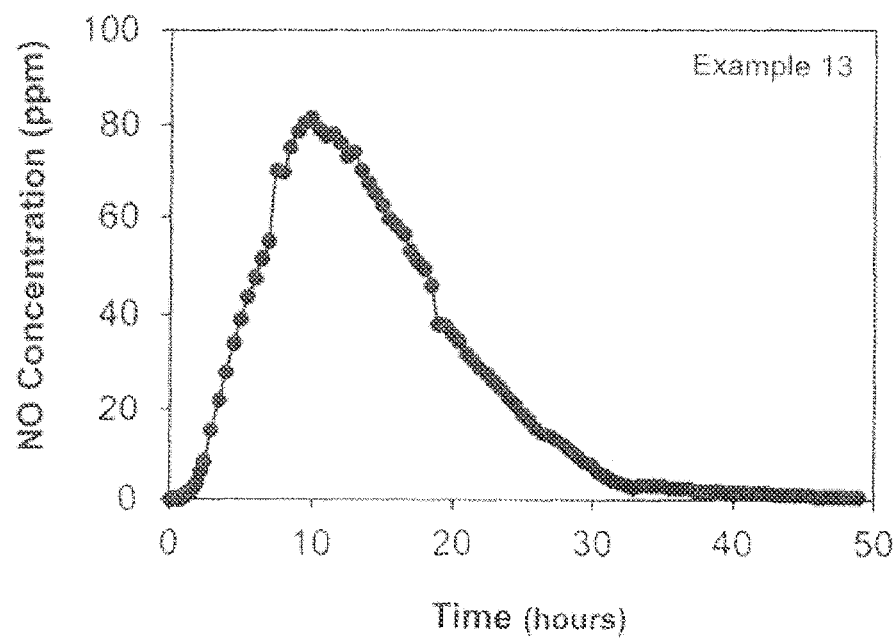
FIG. 26 shows time-dependent concentration change of nitrogen monoxide released off in Example 13.

With the apparatus of FIG. 19, Example 9 was repeated except that the plastic syringe 1920 was loaded up with a mixture comprising 100 mg of a nitrate ion-containing LDH powdery sample, 1.0 mg of powdery iron (II) sulfate heptahydrate and 10.0 g of sandy zinc and the released gases were not diluted with 4 L/min. of air to measure the concentration of nitrogen monoxide by the electro-chemical nitrogen monoxide sensor 1310. The results are shown in FIG. 26. Sandy zinc was pre-treated as in Example 12.

FIG. 26 shows time-dependent concentration change of nitrogen monoxide released off in Example 13.

According to FIG. 26, the concentration of nitrogen monoxide has peaked at about 80 ppm 10 hours after the start of measurement, gone down to about 60 ppm after 15 hours, and down to about 6 ppm after 30 hours, revealing that the nitrate ion-containing LDH/iron (II) sulfate heptahydrate/sandy zinc mixture has improved nitrogen monoxide sustained releasability.

Example 14

Figure 27:
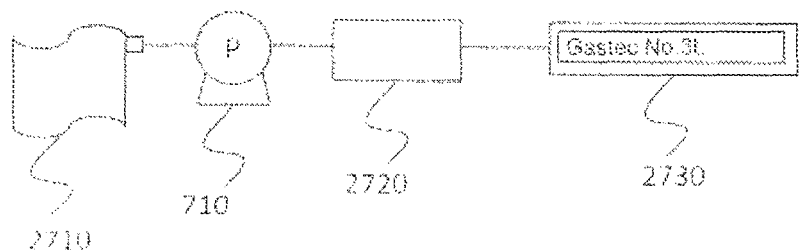
FIG. 27 is a schematic view illustrating an apparatus and experimental system used in Example 14.

In Example 14, the apparatus shown in FIG. 27 was used to perform nitrogenous gas release experimentation with a mixture of the nitrite ion-containing LDH obtained in Example 1 with sandy zinc to measure compositions of the released gases using a detector tube.

FIG. 27 is a schematic view illustrative of the apparatus and experimental system used in Example 14.

The measurement was carried out as mentioned just below. In the apparatus shown in FIG. 27, a pump 710 was used to aerate exhaled air (20° C., a carbon dioxide concentration of 4.0% and a relative humidity of 100%) stored in a 5-L Tedlar bag 2710 through a 2-mL glass Pasteur pipette 2720 for 5 minutes at a flow rate of 100 mL/min. The glass Pasteur pipette 2720 was loaded up with a nitrogenous gas releaser comprising a cotton wool-wrapped mixture comprising 100 mg of a nitrite ion-containing LDH powdery sample and 6.70 g of sandy zinc.

Thereafter, the Tedlar bag 2710 was removed to aerate the air (a relative humidity of 42% to 46%) through the Pasteur pipette 2720 at a flow rate of 100 mL/min to measure the concentration of ammonia contained in an outlet-side gas by a detector tube 2730 (Gastec No. 3L).

As a result, there was no ammonia detected 1 minute and 5 minutes after the start of aeration of the air through the nitrogenous gas sustained releaser. Thereafter, 10 minutes after the start of aeration of the air, 1 ppm of ammonia was detected, and 0.5 ppm, 0.35 ppm and 0.1 ppm of ammonia were detected after 30 minutes, 1 hour, and 1 hour 20 minutes, respectively. Finally, 1 hour 40 minutes after the start of aeration, the concentration of ammonia went down to the detection limitation (0.02 ppm) of the detector tube 2730 or lower. From the aforesaid results, it has been shown that the nitrite ion-containing LDH/zinc mixture is capable of sustainably releasing off ammonia.

Example 15

In Example 15, the apparatus shown in FIG. 28 was used to carry out nitrogenous gas release experimentation with a mixture comprising the nitrite ion-containing LDH obtained in Example 1 with tin (II) chloride dihydrate for measurement of infrared absorption spectra of the released gases.

FIG. 28 is a schematic view illustrative of the apparatus and experimental system used in Example 15.

The apparatus of FIG. 28 comprises a pump 2810 adapted to feed nitrogen and a 30-mL plastic syringe 1910 loaded up with water-wetted gauze for humidification as the atmospheric gas feeding portion, and a 3-mL plastic syringe 2820 as the nitrogenous gas sustained releasing portion. Further, the nitrogenous gas sustained releasing portion is provided in the rear stage with a 30-mL plastic syringe 2830 loaded up with 17.5 grams of molecular sieve 3A 1/16 (made by Kanto Chemical Co., Inc.) as an adsorbent. The plastic syringe 2820 was loaded up with a nitrogenous gas sustained releaser comprising 100 mg of the nitrite ion-containing powdery sample obtained in Example 1 with 1.0 gram of tin (II) chloride dihydrate (made by Nakalai Tesque) with cotton wool put in.

The apparatus was operated as mentioned just below. The pump 2810 was used to feed nitrogen at a flow rate of 100 mL/min and aerate it through the plastic syringe 1910 for humidification. The post-humidification relative humidity was 93%. This humidified nitrogen was aerated through the plastic syringe 2820 for generation of nitrogenous gases, and then through the plastic syringe 2830 for dehumidification. The post-dehumidification gas was aerated through a gas cell 2840 for infrared absorption spectra (made by GL Science Inc. with an optical path length of 10 cm and a window frame of NaCl single crystal) to measure Fourier transform infrared absorption spectra. The results are shown in FIG. 29a.

FIG. 29a shows infrared absorption spectra of the gases released off 2 minutes after the start of measurement. FIG. 29a reveals that the gases released out of the nitrite ion-containing LDH/tin (II) chloride dihydrate mixture contain nitrous oxide, nitrogen monoxide and nitrogen dioxide.

FIG. 29b shows time-dependent concentration change of nitrous oxide in the released gases, and FIG. 29c shows a specific relation between the concentration of nitrous oxide in the released gases and the infrared absorption intensity of 2237 $cm^{-1}$ in the infrared absorption spectra of said gases, said relation defining a nitrous oxide calibration curve.

The calibration curve of the concentration of nitrous oxide was prepared as mentioned just below. A standard gas for nitrous oxide (made by GL Science Inc. with a concentration of 100%) was collected by a syringe, and diluted with dry nitrogen in a 5-L Tedlar bag to prepare nitrous oxide samples having known concentrations (10, 50, 100, 500, and 1000 ppm). About a half volume the gases in the Tedlar bag was aerated through the aforesaid infrared absorption spectrum gas cell, after which an aeration cock of the gas cell was closed to measure Fourier transform infrared absorption spectra. The concentration of nitrous oxide has a favorable linear relation ($R_2$=0.9997) to infrared absorption intensity of 2237 cm$^{-1}$, which relation may be used as a calibration curve.

FIG. 29*b* shows time-dependent concentration change of nitrous oxide calculated using the calibration curve obtained in FIG. 29*c*, indicating that the concentration of nitrous oxide is 1108 ppm two minutes after the start of measurement, and then goes down to 100 ppm and 28 ppm after 10 minutes and 30 minutes, respectively. This result has revealed that the nitrite ion-containing LDH/tin (II) chloride dihydrate mixture is capable of releasing off nitrous oxide in a sustained fashion.

Example 16

Figure 30:
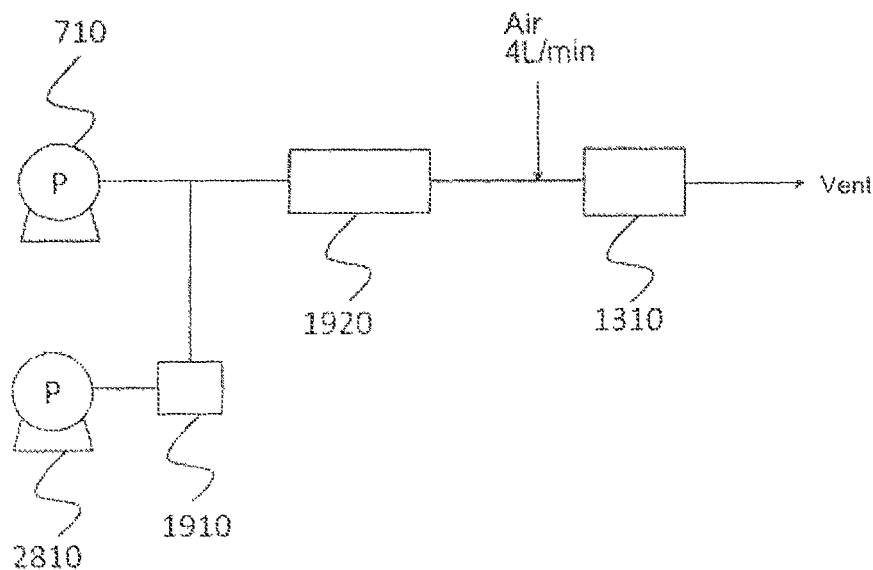
FIG. 30 is a schematic view illustrating an apparatus and experimental system used in Example 16.

In Example 16, the apparatus shown in FIG. 30 was used to perform nitrogenous gas release experimentation with a mixture of the nitrite ion-containing LDH obtained in Example 1 with iron (II) sulfate heptahydrate, thereby measuring compositions of the released gases by an electrochemical nitrogen monoxide sensor.

FIG. 30 is a schematic view illustrative of the apparatus and experimental system used in Example 16.

The apparatus of FIG. 30 comprises a pump 710 adapted to feed the air, a pump 2810 adapted to feed nitrogen, and a 30-mL plastic syringe 1910 connected to the pump 2810 as the atmospheric gas feeding portion. The plastic syringe 1910 is loaded up with water-wetted gauze for humidification. Further, the apparatus of FIG. 30 comprises a 3-mL plastic syringe 1920 as the nitrogenous gas releasing portion. The plastic syringe 1920 is loaded up with the nitrogenous gas sustained releaser comprising a mixture of 50 mg of the nitrite ion-containing LDH powdery sample obtained in Example 1 and 0.5 gram of iron (II) sulfate heptahydrate with cotton wool put in. The plastic syringe 1920 is provided in the rear stage with an electrochemical nitrogen monoxide sensor 1310 adapted to detect nitrogen monoxide gas in the released gases. In FIG. 30, the air from the pump 710 and nitrogen from the pump 2810 are interchangeable.

The apparatus was operated as mentioned just below. First of all, the pump 710 was used to aerate the air having a relative humidity of 38% through the plastic syringe 1920 at a flow rate of 100 mL/min, and diluted with 4.0 L/min. of the air, after which the electro-chemical nitrogen monoxide sensor 1310 was used to measure the concentration of nitrogen monoxide for 3 hours. Thereafter, the pump 710 was switched over to the pump 2810 to feed and aerate nitrogen through the plastic syringe 1910 at a flow rate of 100 mL/min for humidification. The post-humidification relative humidity was 93%. This humidified nitrogen was aerated through the plastic syringe 1920 to measure the concentration of nitrogen monoxide for 3 hours using the electrochemical nitrogen monoxide sensor 1310 as was the case with the aeration of the air. The results are shown in FIG. 31.

Figure 31:
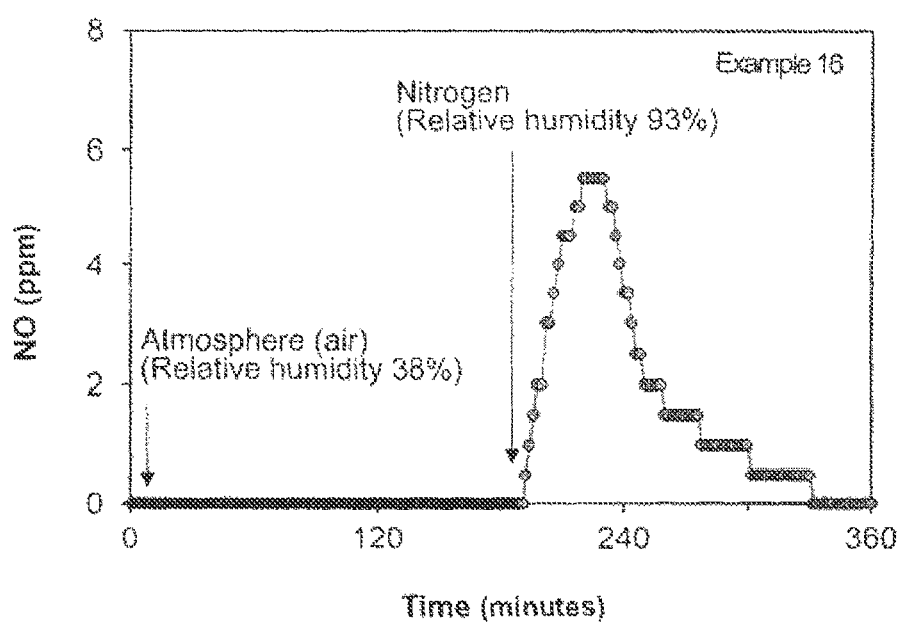
FIG. 31 shows time-dependent concentration change of nitrogen monoxide released off in Example 16.

FIG. 31 shows time-dependent concentration change of nitrogen monoxide in Example 16.

Even with contact of the air with the nitrogenous gas sustained releaser, there was no nitrogen monoxide detected. As nitrogen gas saturated with water vapor was brought in contact with the nitrogenous gas sustained releaser, however, release of nitrogen monoxide was observed from just after contact, revealing that nitrogen monoxide could be sustainably released off.

The sustained release curve shown in FIG. 31 is very close to a sustained release behavior observed when, in FIG. 21 (Example 9), the same amount of the nitrite ion-containing LDH powder/iron (II) sulfate heptahydrate mixture comes in contact with the humidified air, revealing that if gas having a relative humidity of at least 40% or higher is fed to a nitrite ion-containing LDH/reducing agent mixture, it is then possible to release off nitrogen monoxide in a sustained manner.

It is here understood that according to the method described here, nitrogen monoxide can be released off by feeding a gas based on nitrogen gas or rare gas and free of oxygen and/or carbon dioxide so that oxidation of nitrogen monoxide by oxygen can be prevented. For this reason, the released nitrogen monoxide can be stored in a Tedlar bag for a certain period of time, and used after a passage of time from release. Further, if nitrogen gas or rare gas containing nitrogen monoxide and water vapor is brought in contact with molecular sieve 3A, it is then possible to adsorb and eliminate only water molecules having a small molecular diameter thereby purifying nitrogen monoxide. According to a conventional method of forming nitrogen monoxide from atmospheric nitrogen and oxygen by arc discharge, on the other hand, nitrogen monoxide and oxygen coexist in principle, rendering it not easy to store the generated nitrogen monoxide in a stable way.

Example 17

Figure 32:
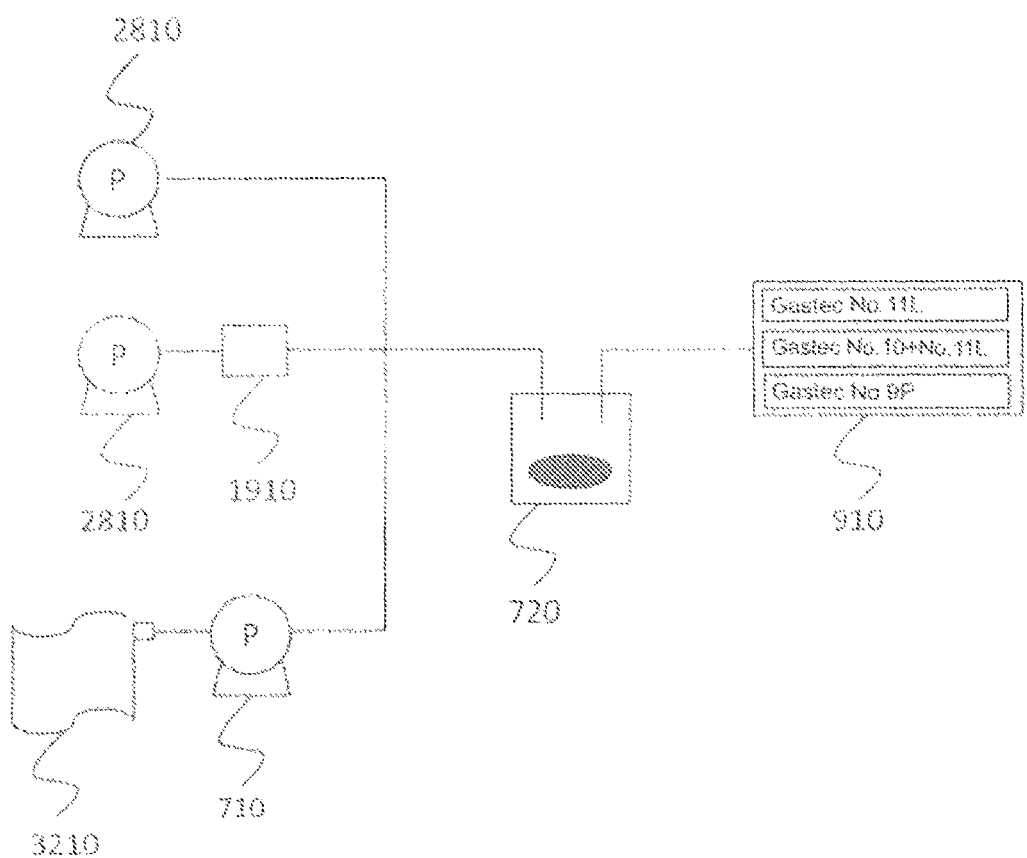
FIG. 32 is a schematic view illustrating an apparatus and experimental system used in Example 17.

In Example 17, the apparatus shown in FIG. 32 was used to aerate dry nitrogen gas, saturated water vapor-containing nitrogen gas, and carbon dioxide-containing dry nitrogen gas through the nitrite ion-containing LDH obtained in Example 1 to carry out nitrogenous gas release experimentation for measurement of compositions of the released gases by a detector tube.

FIG. 32 is a schematic view illustrative of the apparatus and experimental system used in Example 17.

The apparatus of FIG. 32 is assembled from the atmospheric gas feeding portion comprising two pumps 2810 adapted to feed dry nitrogen, a 30-mL plastic syringe 1910 connected to one of the pumps 2810, a Tedlar bag 3210 loaded up with dry nitrogen containing 4.0% of carbon dioxide, and a pump 710 connected to the Tedlar bag 3210 to feed the inside gas to the nitrogenous gas releasing portion. The plastic syringe 1910 is loaded up with water-wetted gauze for humidification. Referring here to the aforesaid atmospheric gas feeding portion, the pump 2810 for feeding dry nitrogen, the plastic syringe 1910 and the pump 710 are respectively connected to a 13.5-mL glass vial bottle forming the nitrogenous gas sustained releasing portion, said glass vial bottle being provided therein with 100 mg of the nitrite ion-containing LDH 720 obtained in Example 1. A detector tube 910 adapted to measure compositions of gases released out of the nitrite ion-containing LDH 720 is provided in the rear stage of the glass vial bottle. In FIG. 32, three gases to be fed to the nitrite ion-containing LDH 720 are dry nitrogen, saturated water vapor-containing nitrogen, and dry nitrogen containing 4.0% of carbon dioxide that are interchangeable or switchable.

The apparatus was operated as mentioned just below. First of all, the 13.5-mL glass vial bottle having 100 mg of nitrite ion-containing LDH 720 was provided. This was placed in a desiccator, and vacuum pump connected to said desiccator was then operated for a 30-minutes or longer drying, thereby fully removing nitrogenous gases generated by contact with the air during storage or weighing of the nitrite ion-containing LDH 720. After drying, the desiccator was nitrogen purged and then opened up for quick connection of the glass vial bottle to the apparatus of FIG. 32. Then, the pump 2810 was operated to feed dry nitrogen into the glass vial bottle at a flow rate of 50 mL/min. Nitrogenous gases contained in the dry nitrogen gas after contact with the nitrite ion-containing LDH 720 were measured by the detector tube 910 for nitrogen monoxide+nitrogen dioxide (Gastec No. 11L), but there was no response obtained.

Subsequently, the gas to be fed to the nitrite ion-containing LDH 720 was switched over to the saturated water vapor-containing nitrogen gas, just after which nitrogenous gases were released off and the detector tube 910 indicated 0.2 ppm. Even after the passage of one or two hours, the detector tube 910 still indicated 0.2 ppm, revealing that as gas having a relative humidity of 40% or higher comes in contact with the nitrite ion-containing LDH, it causes nitrogenous gases to be sustainably released off by gas free of carbon dioxide. It is here noted that as a consequence of measurement by other detector tube according to a similar method as in Example 3, nitrogen dioxide was found to be about 0.02 ppm and nitrogen monoxide was found to be 0.01 ppm or lower. From this, the main component of the aforesaid 0.2 ppm nitrogenous gas has been considered to be nitrous acid vapor, and anions remaining in the LDH layer in place of the generation of nitrous acid vapor have been expected to be hydroxide ions ($OH^-$) derived from water.

Subsequently, once the glass vial bottle was removed out of the apparatus of FIG. 32, the nitrite ion-containing LDH 720 was dried in vacuo in the aforesaid desiccator for 40 minutes. After drying, the desiccator was nitrogen purged and opened up for quick connection of the glass vial bottle to the apparatus shown in FIG. 32 and dry nitrogen was then fed at a flow rate of 50 mL/min. Nitrogenous gases contained in the dry nitrogen gas after contact with the nitrite ion-containing LDH 720 were measured by the detector tube 910 for nitrogen monoxide+nitrogen dioxide (Gastec No. 11L), but there was no response observed.

Subsequently, the gas to be fed to the nitrite ion-containing LDH 720 was changed over to dry nitrogen gas containing 4.0% of carbon dioxide, just after which nitrogenous gases were found to be released off, and the detector tube 910 indicated 4.0 ppm. The dry nitrogen gas containing 4.0% of carbon dioxide was fed from within the Tedlar bag 3210 using the pump 710. The detector tube 910 indicated 4.5 ppm 10 minutes after changeover, 4.5 ppm after 26 minutes, 4.5 ppm after 50 minutes, and 4.5 ppm after 77 minutes. From this, it has been revealed that by contact of gas containing at least carbon dioxide with the nitrite ion-containing LDH, nitrogenous gases can be released off in a sustained manner. Note here that the proton source of generating nitrous acid vapor has been considered to be LDH interlayer water.

From the foregoing results, it has been revealed that by contact of gas containing water vapor and/or carbon dioxide with nitrite ion-containing LDHs, nitrogenous gases can be released off in a sustained manner.

INDUSTRIAL APPLICABILITY

According to the present invention, a solid material capable of sustainably releasing off nitrogenous gases at normal temperature in the air can be obtained in a simpler, safer way than ever before. The obtained nitrogenous gas sustained releasing agent generates nitrogenous gases by coming in contact with the air or exhaled air; so it basically dispenses with operations using external energy such as heating or light irradiation. Because the concentration of nitrogenous gases is substantially proportional to the proportion of nitrite ions/nitrate ions included between LDH layers, control of nitrogenous gases is easily achievable. For this reason, the solid material of the invention is expectably well fit for a nitrogen monoxide gas feed source in medical applications where it is exposed to low concentrations over an extended period of time.

Referring specifically to how to use the inventive solid material, there is the mention of maintenance-free, disposable equipment such as a ventilator or mask adapted to feed nitrogen monoxide into exhaled air in a concentration harmless to the human body for the purpose of treating pulmonary hypertension, etc. At present, costly medical equipment is needed for nitrogen monoxide inhalation; there are some limitations on installations, countries and areas where nitrogen monoxide inhalation is available. According to the invention, however, it is easy to generate nitrogen monoxide having medical concentrations by exposing the nitrogenous gas sustained releasing agent or releaser to air. Thus, it is possible to perform a nitrogen monoxide inhalation method in situations or environments remaining unmanageable in the state of art such as emergency lifesaving of patients having difficulty breathing, in developing countries, at home, and at the time of power failure, contributing more to its spread.

As known in the art, nitrogen monoxide has bioactive effects on vasodilatation and other effects such as anti-oxidative, anti-inflammatory, vasodilatation, and pasteurization effects. According to the present invention, it is possible to apply nitrogen monoxide to a local site of external tissues such as the skin because nitrogen monoxide on the order of ppm can easily be generated by exposure to air of the nitrogenous gas sustained releasing agent or releaser comprising the nitrite ion/nitrate ion-containing LDH. This would show promise as cosmetic medications or wound medications.

The present invention would also show great promise as a nitrogenous gas source that may be used in place of difficult-to-handle, hazardous, high-weight gas bombs not only in medical fields but also in industrial fields or research fields. According to the present invention, a cost of manufacturing may be suppressed because commercially available, inexpensive LDHs and nitrites/nitrates may be used as the starting material at lower costs and dispensing with any special production apparatus. In addition, the nitrogenous gas sustained releasing agent of the invention allows LDH to take hold of its structure even after nitrogenous gas release comes to an end, and is useful as a chemically stable, deliquescence-free, greatly safe agent of releasing off nitrogenous gases in general, and nitrogen monoxide in particular in a sustained manner.

EXPLANATION OF THE REFERENCE NUMERALS

100: Layered double hydroxide (LDH)
110: Layers
120: Anions
200, 310, 720: Nitrite ion-containing LDH
300, 510, 2430: Nitrogenous gas sustained releaser
320: Reducing agent
500: Package
520: Wrapping material 600: Sustained releasing apparatus
610: Atmospheric gas feeding portion
620: Nitrogenous gas sustained releasing portion
630: Impurity gas removal portion
710, 2810: Pump
730, 2460: Filter
740: Aqueous solution having Griess reagent dissolved therein
910, 1930, 2530, 2730: Detector tube
1010, 2710, 3210: Tedlar bag
1110: Pasteur column loaded up with iron (II) sulfate heptahydrate
1210: Plastic syringe loaded up with magnesium hydroxide
1310: Electrochemical nitrogen monoxide sensor
2410: Hand pump
1910, 2420, 2510: Humidifier (plastic syringe or gas washing bottle)
1920, 2820: Plastic syringe loaded up with the nitrogenous gas sustained releaser
2520, 2720: Pasteur pipette loaded up with the nitrogenous gas sustained releaser
2440, 2830: Adsorbent or plastic syringe loaded up with adsorbent
2450: Ventilator
2840: Gas cell

What is claimed is:

1. A nitrogenous gas sustained releaser, comprising a sustained releasing agent of sustainably releasing off nitrogenous gases, which contains a layered double hydroxide having a nitrite ion ($NO_2^-$) included between layers and a solid reducing agent or a solid oxidizing agent,
wherein said nitrogenous gas sustained releaser has the capability of allowing a nitrogenous gas having a concentration of 1/100 or more of the maximum value to be continuously detected over 30 minutes or longer within a fluctuation range of 25% in the nitrogenous gas release experimentation.

2. The nitrogenous gas sustained releaser according to claim 1, wherein said nitrogenous gases are at least one gas selected from the group consisting of nitrogen monoxide gas (NO), nitrous acid vapor ($HNO_2$) and nitrogen dioxide gas ($NO_2$).

3. The nitrogenous gas sustained releaser according to claim 1, wherein said layered double hydroxide is represented by the following general formula (1):

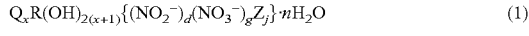

$$Q_x R(OH)_{2(x+1)}\{(NO_2^-)_d(NO_3^-)_g Z_j\} \cdot nH_2O \qquad (1)$$

where Q is a divalent metal ion, R is a trivalent metal ion, Z is an anion other than $NO_2^-$ and $NO_3^-$, each of x, d, g and j is a number that satisfies $1.8 \leq x \leq 4.2$, $0.01 \leq d+g \leq 2.0$ and $0 \leq j \leq 1.0$, and n is a number that changes depending on an environmental humidity.

4. The nitrogenous gas sustained releaser according to claim 3, wherein, in said general formula (1), said Q is at least one selected from the group consisting of $Mg^{2+}$, $Mn^{2+}$, $Fe^{2+}$, $Co^{2+}$, $Ni^{2+}$, $Cu^{2+}$, $Zn^{2+}$ and $Ca^{2+}$, and said R is at least one selected from the group consisting of $Al^{3+}$, $Ga^{3+}$, $Cr^{3+}$, $Mn^{3+}$, $Fe^{3+}$, $Co^{3+}$ and $Ni^{3+}$.

5. The nitrogenous gas sustained releaser according to claim 1, wherein said sustained releasing agent is mixed with said solid reducing agent or said solid oxidizing agent.

6. A nitrogenous gas sustained releasing method using a nitrogenous gas sustained releaser according to claim 1 which is capable of sustainably releasing off nitrogenous gases, and
comprises a gas contact step of bringing a gas containing carbon dioxide and/or water vapor in contact with the nitrogenous gas sustained releaser.

7. The nitrogenous gas sustained releasing method according to claim 6,
further comprising a step of bringing nitrous acid vapor obtained in the gas contact step in contact with a solid reducing agent or solid oxidizing agent.

8. The nitrogenous gas sustained releasing method according to claim 6, wherein a mixture of said sustained releasing agent with a solid reducing agent and/or a solid oxidizing agent is used as said nitrogenous gas sustained releaser, and the method further includes a step of bringing a gas having a relative humidity of 40% or more in contact with said releaser.

9. The nitrogenous gas sustained releasing method according to claim 6, which further include a step of removing impurities in the gas sustainably released out of said nitrogenous gas sustained releaser using an adsorbent.

10. The nitrogenous gas sustained releasing method according to claim 9, wherein said adsorbent contains magnesium hydroxide or calcium hydroxide.

11. A package comprising:
the nitrogenous gas sustained releaser according to claim 1; and
a wrapping material adapted to seal up and contain said nitrogenous gas sustained releaser.

12. The package according to claim 11, wherein an atmosphere filled in said wrapping material is selected from the group consisting of a voidless atmosphere, a vacuum atmosphere, an inert gas atmosphere and a dry atmosphere.

13. The nitrogenous gas sustained releaser according to claim 1, wherein neither said layered double hydroxide, said reducing agent, nor said oxidizing agent are macroscopically present as aqueous suspension or aqueous solution.

14. The nitrogenous gas sustained releaser according to claim 1, wherein said solid reducing agent or said solid oxidizing agent is mixed with said layered double hydroxide in an amount of 10% by mass to 10000% by mass inclusive.

* * * * *